US010435368B2

(12) United States Patent
Peters et al.

(10) Patent No.: US 10,435,368 B2
(45) Date of Patent: Oct. 8, 2019

(54) HIGH HEAT MONOMERS AND METHODS OF USE THEREOF

(71) Applicant: SABIC GLOBAL TECHNOLOGIES B.V., Bergen op Zoom (NL)

(72) Inventors: Edward Norman Peters, Lenox, MA (US); Prakash Sista, Evansville, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 174 days.

(21) Appl. No.: 15/327,433

(22) PCT Filed: Jul. 22, 2015

(86) PCT No.: PCT/US2015/041478
§ 371 (c)(1),
(2) Date: Jan. 19, 2017

(87) PCT Pub. No.: WO2016/014629
PCT Pub. Date: Jan. 28, 2016

(65) Prior Publication Data
US 2017/0166528 A1    Jun. 15, 2017

Related U.S. Application Data

(60) Provisional application No. 62/027,638, filed on Jul. 22, 2014.

(51) Int. Cl.
| | |
|---|---|
| *C07D 209/34* | (2006.01) |
| *C07D 209/36* | (2006.01) |
| *C08K 7/06* | (2006.01) |
| *C08K 7/14* | (2006.01) |
| *C07D 209/46* | (2006.01) |
| *C07C 39/15* | (2006.01) |
| *C07C 39/17* | (2006.01) |
| *C08F 212/12* | (2006.01) |
| *C08F 222/20* | (2006.01) |
| *C08F 222/22* | (2006.01) |

(52) U.S. Cl.
CPC ........... *C07D 209/46* (2013.01); *C07C 39/15* (2013.01); *C07C 39/17* (2013.01); *C07D 209/34* (2013.01); *C07D 209/36* (2013.01); *C08F 212/12* (2013.01); *C08F 222/20* (2013.01); *C08F 222/22* (2013.01); *C08K 7/06* (2013.01); *C08K 7/14* (2013.01); *C07C 2601/14* (2017.05); *C07C 2603/02* (2017.05); *C07C 2603/18* (2017.05); *C07C 2603/68* (2017.05); *C07C 2603/86* (2017.05); *C07C 2603/94* (2017.05)

(58) Field of Classification Search
CPC ... C07D 209/46; C07D 209/34; C07D 209/36
See application file for complete search history.

(56) References Cited

U.S. PATENT DOCUMENTS

| | | | | |
|---|---|---|---|---|
| 8,247,523 | B2 * | 8/2012 | Bhotla | C08G 64/12 528/271 |
| 8,779,162 | B2 * | 7/2014 | Ikeno | C07D 209/34 548/484 |
| 2007/0078198 | A1 * | 4/2007 | Otsuji | C07C 69/54 523/120 |
| 2010/0003523 | A1 * | 1/2010 | Sharygin | B29C 45/14688 428/412 |
| 2011/0151262 | A1 | 6/2011 | Heuer et al. | |
| 2013/0023640 | A1 | 1/2013 | Ikeno et al. | |
| 2016/0060403 | A1 * | 3/2016 | Mahood | C08J 5/18 428/220 |
| 2017/0029562 | A1 * | 2/2017 | Pillai | C08G 64/12 |
| 2017/0158806 | A1 * | 6/2017 | Peters | C07D 405/12 |

FOREIGN PATENT DOCUMENTS

| | | | | |
|---|---|---|---|---|
| EP | 2527324 A1 | | 11/2012 | |
| JP | 10338725 A | * | 12/1998 | ............ C08F 22/105 |
| JP | 11116625 A | * | 4/1999 | |
| JP | 2015232126 A | | 12/2015 | |
| WO | WO-2010067330 A1 | * | 6/2010 | ............ C07D 209/46 |
| WO | WO-2014156778 A1 | * | 10/2014 | ............ C08F 212/32 |
| WO | WO-2014157131 A1 | * | 10/2014 | ............ C08F 290/126 |

OTHER PUBLICATIONS

Machine translation of WO 2014/157131 A1, retrieved May 2019. (Year: 2019).*
Bureeva, S., et al., "Inhibition of classical pathway of complement activation with negative charged derivatives of bishphenol A and bishphenol disulphates", Bioorganic & Medicinal Chemistry 13 (2005) 1045-1052.
International Search Report for PCT/US2015/041478, dated Dec 23, 2015, 9 pages.
Papava, G., et al., "Oxypropylation of bisphenols with phthalide and phthalimidine groups", Chemical Abstracts Services, Columbus, OH (1992) Abstract Only (XP-002743961).
Papava, G., et al., "Synthesis of diols with phthalide and phthalimidine groups", Chemical Abstract Services, Columbus, OH (1985) Abstract Only (XP-002743962).
Salazkin, S.N., et al., "Preparation of cardo bisphenols and some of their derivatives", Chemical Abstract Services, Columbus, OH (1978) Abstract Only (XP-002744964).
Written Opinion of the International Searching Authority for PCT/US2015/041478, dated Dec. 23, 2015, 8 pages.
STN Columbus, CAPLUS, 67653-52-5; retrieved Feb. 24, 2019, 3 pages.

* cited by examiner

*Primary Examiner* — Nicole M. Buie-Hatcher
(74) *Attorney, Agent, or Firm* — Cantor Colburn LLP

(57) ABSTRACT

High heat monomer compounds, methods for preparing compounds, and compositions derived from the compounds are provided. Also provided are materials and articles derived from the compounds.

20 Claims, No Drawings

HIGH HEAT MONOMERS AND METHODS OF USE THEREOF

CROSS-REFERENCE TO RELATED APPLICATIONS

This application is a national stage application of PCT/US2015/041478 filed Jul. 22, 2015, which claims priority to U.S. Provisional Application No. 62/027,638 filed Jul. 22, 2014, both of which are hereby incorporated by reference in their entirety.

BACKGROUND

The present disclosure generally relates to high heat monomers, methods for producing the monomers, curable compositions including the monomers, and articles and materials including the cured compositions.

High performance monomer materials and compositions are used in a wide variety of applications including protective coatings, adhesives, electronic laminates (such as those used in the fabrication of computer circuit boards), flooring and paving applications, glass fiber-reinforced pipes, and automotive parts (including leaf springs, pumps, and electrical components). In their cured form, the materials offer desirable properties including good adhesion to other materials, excellent resistance to corrosion and chemicals, high tensile strength, and good electrical resistance. There exists a need for materials with improved properties.

SUMMARY

In one aspect, disclosed is a compound having formula:

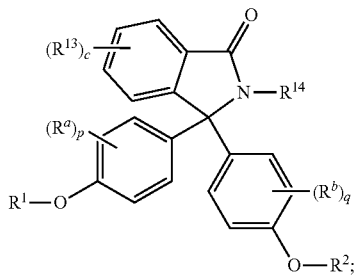

(I)

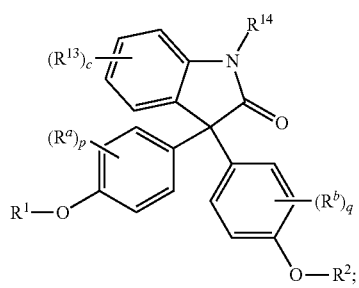

(II)

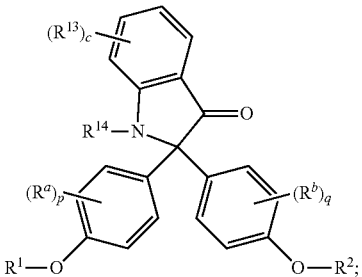

(III)

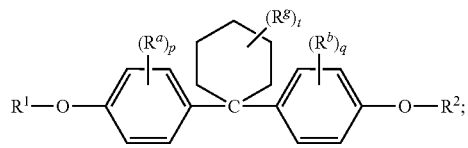

(IV)

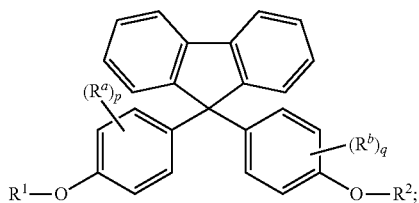

(V)

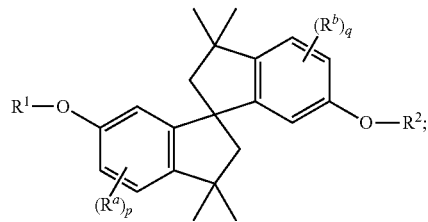

(VI)

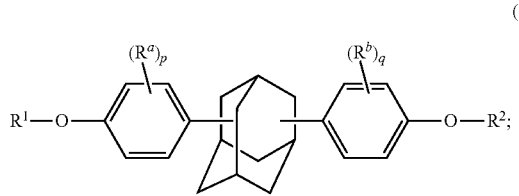

(VII)

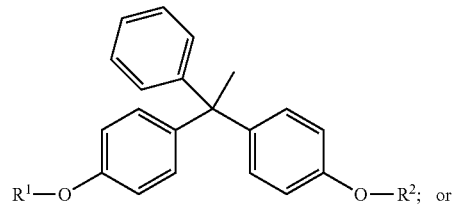

(VIII) or

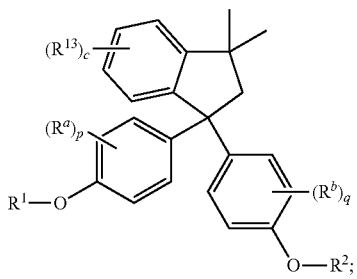

(IX)

wherein $R^1$ and $R^2$ at each occurrence are each independently selected from a reactive functional group; $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five-, or six-membered cycloalkyl group; and t is 0 to 10.

In certain embodiments, $R^1$ and $R^2$ at each occurrence are each independently selected from: cyano; haloalkyl; alkenyl; alkenylalkyl; alkynylalkyl; hydroxyalkyl; acrylatealkyl;

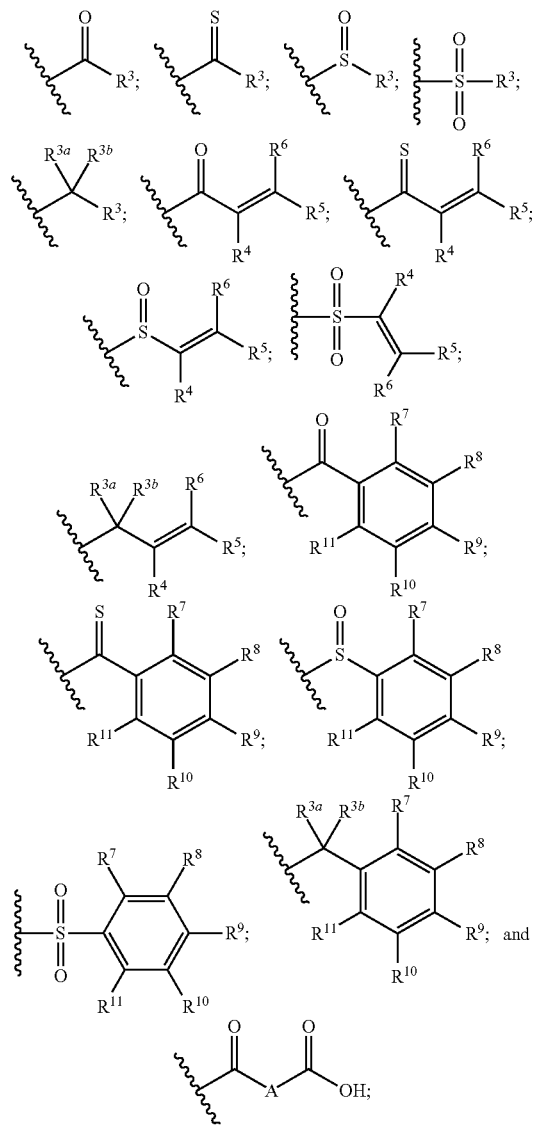

wherein $R^3$, at each occurrence, is independently selected from $C_1$-$C_{12}$ alkyl, heteroaryl, alkoxy, amino, and alkylamino; $R^4$-$R^6$ are each independently selected from hydrogen, $C_1$-$C_{12}$ alkyl, $C_2$-$C_{12}$ alkenyl, $C_6$-$C_{18}$ aryl, $C_7$-$C_{18}$ alkyl-substituted aryl, $C_7$-$C_{18}$ aryl-substituted alkyl, $C_2$-$C_{12}$ alkoxycarbonyl, $C_7$-$C_{18}$ aryloxycarbonyl, $C_8$-$C_{18}$ alkyl-substituted aryloxycarbonyl, $C_8$-$C_{18}$ aryl-substituted alkoxycarbonyl, nitrile, formyl, carboxylate, imidate, and thiocarboxylate; $R^7$-$R^{11}$ are each independently selected from hydrogen, halogen, $C_1$-$C_{12}$ alkyl, $C_2$-$C_{12}$ alkenyl, hydroxy, and amino; $R^{3a}$ and $R^{3b}$ are each independently selected from hydrogen and $C_1$-$C_{12}$ alkyl; and A at each occurrence is independently selected from a saturated or unsaturated $C_2$-$C_{12}$ divalent hydrocarbon group.

In certain embodiments, $R^1$ and $R^2$ are each independently selected from:

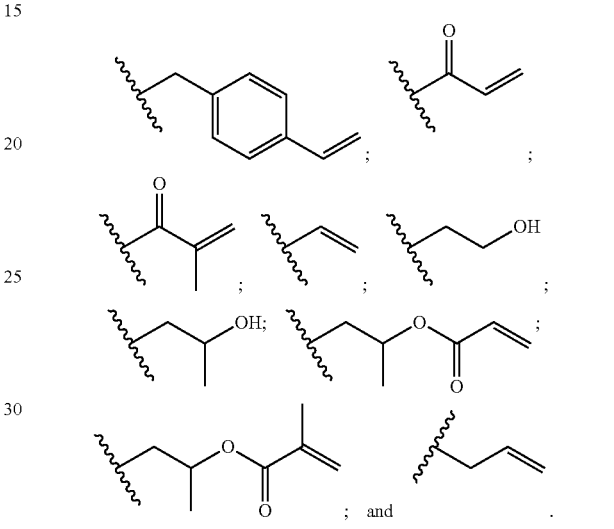

In certain embodiments, the compound can be any of the following:

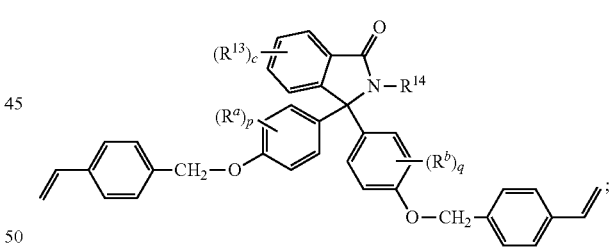
(1)

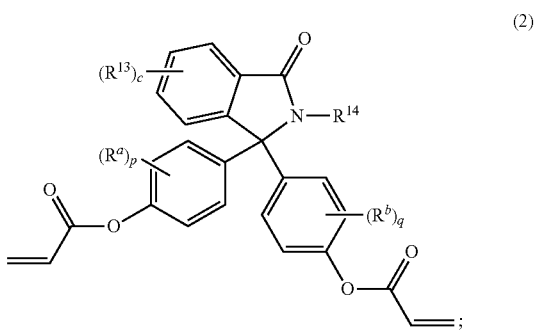
(2)

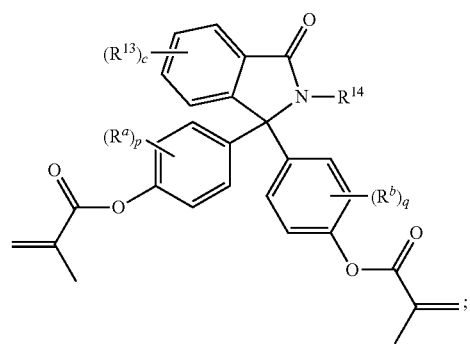
(3)
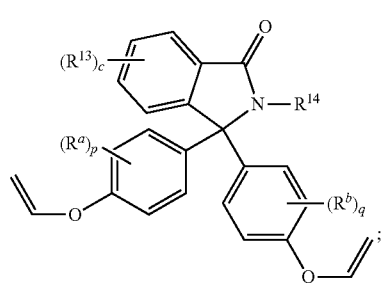
(4)
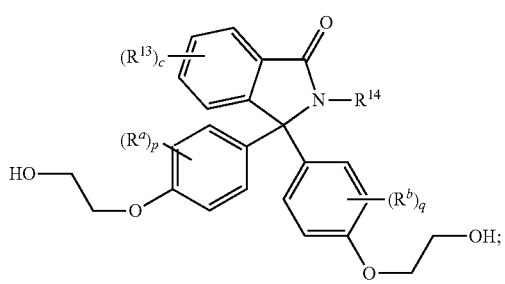
(5)
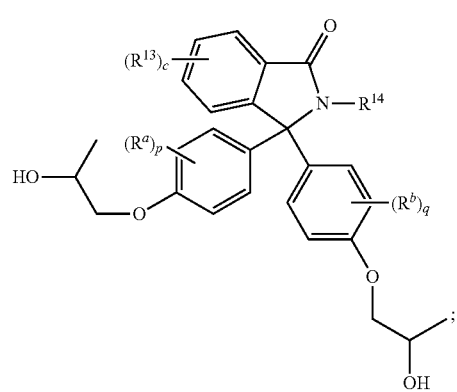
(6)
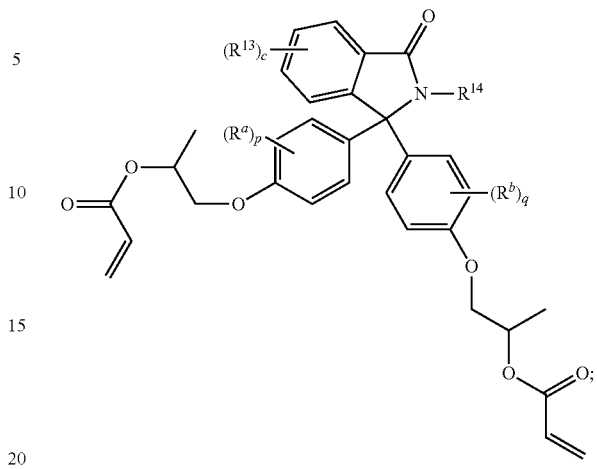
(7)
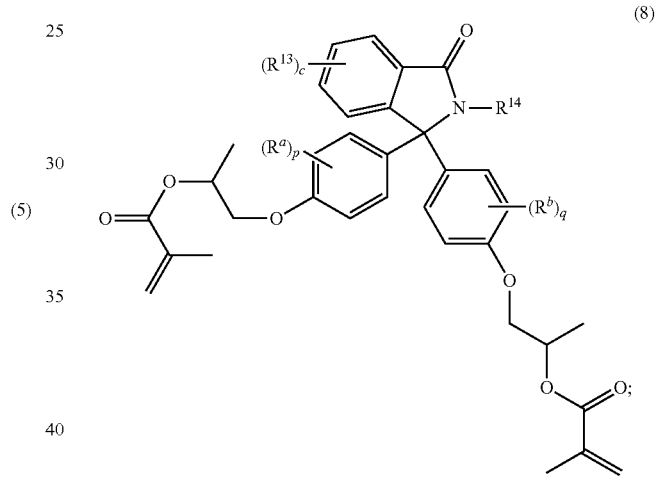
(8)
(9)

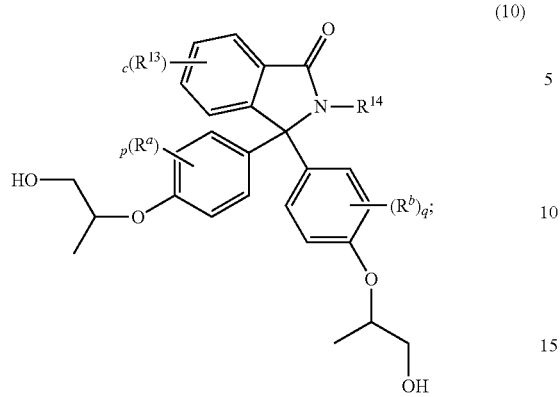

(10)

wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; and $R^{14}$ at each occurrence is independently a $C_1$-$C_6$ alkyl, phenyl, or phenyl substituted with up to five halogens or $C_1$-$C_6$ alkyl groups.

In certain embodiments, the compound has a purity of 80% or greater, as determined by high performance liquid chromatography (HPLC).

In certain embodiments, the compound has a purity of 90% or greater, as determined by high performance liquid chromatography (HPLC).

In certain embodiments, the compound has a purity of 95% or greater, as determined by high performance liquid chromatography (HPLC).

In certain embodiments, the compound has a purity of 97% or greater, as determined by high performance liquid chromatography (HPLC).

In certain embodiments, the compound has a purity of 98% or greater, as determined by high performance liquid chromatography (HPLC).

In certain embodiments, the compound has a purity of 99% or greater, as determined by high performance liquid chromatography (HPLC).

In certain embodiments, the compound can be any of the following:

(1-a)

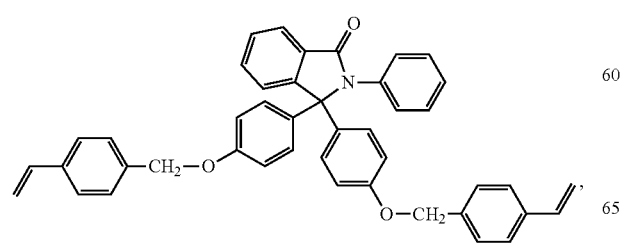

(2-a)

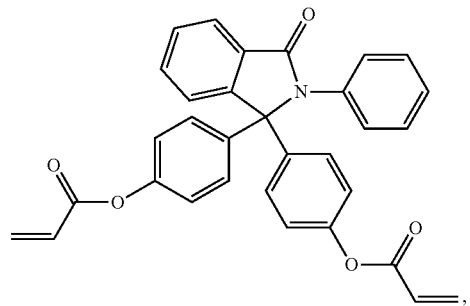

(3-a)

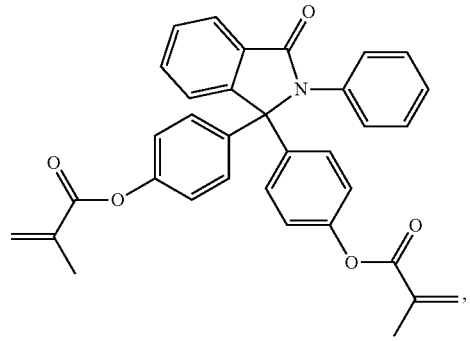

(4-a)

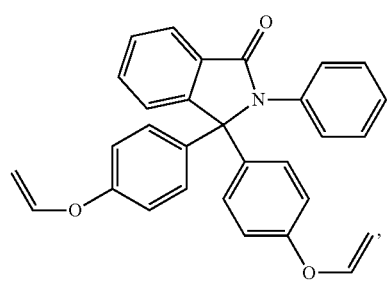

(5-a)

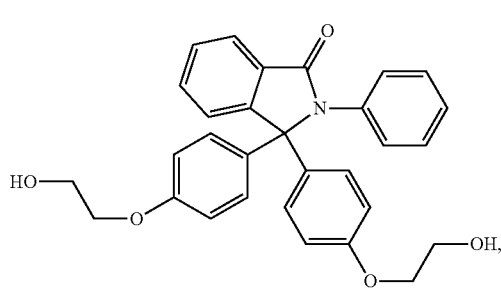

(6-a)

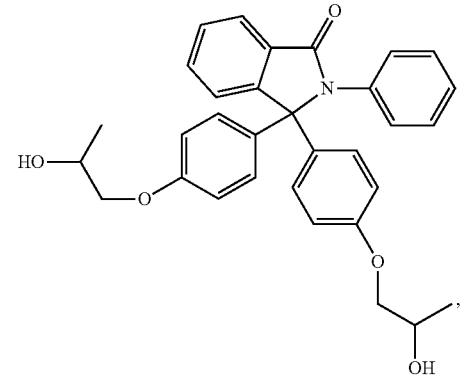

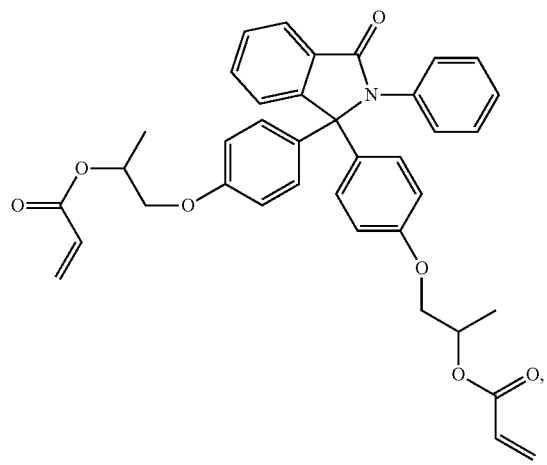

(7-a)

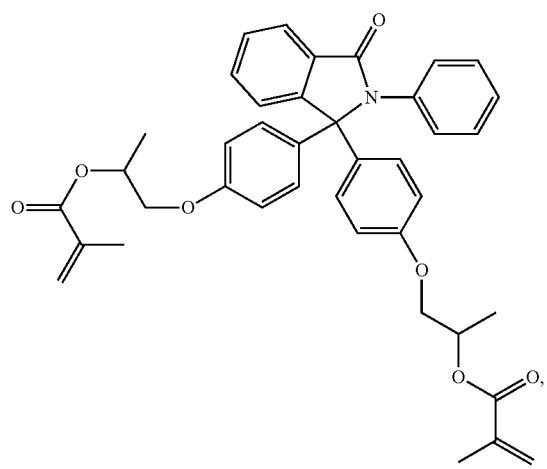

(8-a)

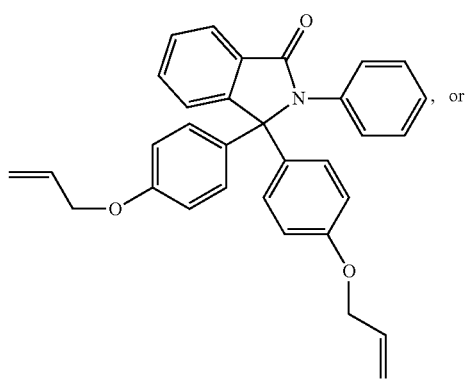

(9-a), or

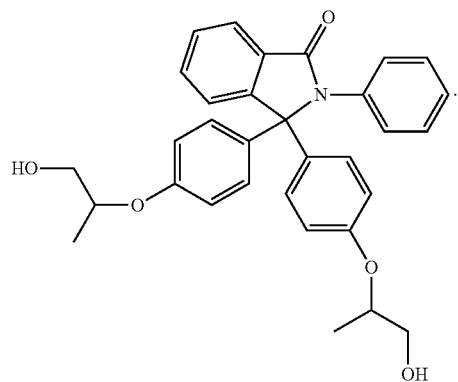

(10-a)

In certain embodiments, the compound is derived from a compound of formula (1'):

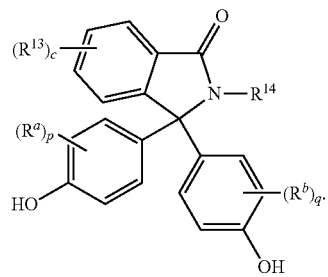

(1')

In certain embodiments, the compound is derived from a compound of formula (1'-a):

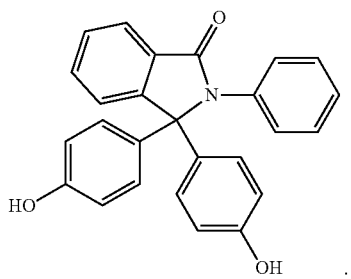

(1'-a)

In certain embodiments, the compound of formula (1'-a) comprises less than 50 ppm of amino phenol impurities, less than 500 ppm of phenolphthalein, or 3 ppm or less of metal impurities.

In another aspect, disclosed is a curable composition comprising (i) a compound according to any one of formulae (I), (II), (III), (IV), (V), (VI), (VII), (VIII), (IX), (1), (2), (3), (4), (5), (6), (7), (8), (9), (10), (1-a), (2-a), (3-a), (4-a), (5-a), (6-a), (7-a), (8-a), (9-a), (10-a), (1'), and (1'-a); (ii) a curing promoter; (iii) a polymerization inhibitor, and (iii) optionally an auxiliary co-monomer.

In certain embodiments, the auxiliary co-monomer is selected from maleimide resins, benzoxazine resins, vinylbenzyl ether resins, alkene- or alkyne-containing monomers, arylcyclobutene resins, perfluorovinyl ether resins, oligomers and polymers with curable vinyl functionality, and combinations thereof.

In certain embodiments, the curing promoter is an organic peroxide.

In certain embodiments, the organic peroxide is selected from cumene hydroperoxide, 2,5-dimethylhexane-2,5-dihydroperoxide, 2,5-dimethylhexane-2,5-dihydroperoxide, α,α-bis(t-butylperoxy-m-isopropyl)benzene, dicumyl peroxide, di(trimethylsilyl)peroxide, trimethylsilyl triphenylsilyl peroxide, 2,5-dimethyl-2,5-di(t-butylperoxy) hexane (DHBP), 2,5-dimethyl-2,5-di(t-butylperoxy)-hex-3-yne (DYBP), di-t-butylperoxide (DTBP), t-butylcumyl peroxide, dicumyl peroxide (DCP), di(t-butylperoxyisophthalate, t-butylperoxybenzoate, 2,2-bis(t-butylperoxy)butane, 2,2-bis(t-butylperoxy)octane, 2,5-dimethyl-2,5-di(benzoylperoxy)hexane, di(trimethylsilyl) peroxide, trimethylsilylphenyltriphenylsilyl peroxide, α,α'-bis(t-butylperoxy-m-isopropyl)benzene, 1,3-di(2-tert-butylperoxy isopropyl) benzene (DIPP), benzoyl peroxide (BPO), 3,3',5,5'-tetramethyl-1,4-diphenoxyquinone, chloranil, 2,4,6-tri-t-butylphenoxyl, t-butylperoxyisopropyl monocarbonate, azobisisobutyronitrile, and combinations thereof.

In another aspect, disclosed is a cured composition comprising the product obtained by curing the curable composition.

In certain embodiments, the cured composition exhibits a single glass transition temperature.

In certain embodiments, the cured composition exhibits a single Tg of greater than or equal to 175° C. In certain embodiments, the cured composition exhibits a single Tg of greater than or equal to 200° C. In certain embodiments, the cured composition exhibits a single Tg of greater than or equal to 225° C. In certain embodiments, the cured composition exhibits a single Tg of greater than or equal to 250° C.

In another aspect, disclosed is an article comprising the cured composition.

In certain embodiments, the article is selected from acid bath containers; neutralization tanks; aircraft components; bridge beams; bridge deckings; electrolytic cells; exhaust stacks; scrubbers; sporting equipment; stair cases; walkways; automobile exterior panels; floor pans; air scoops; pipes; natural gas pipes; ducts; industrial fans; fan housings; blowers; industrial mixers; boat hulls; boat decks; marine terminal fenders; tiles; building panels; business machine housings; trays; concrete modifiers; dishwasher parts; refrigerator parts; electrical encapsulants; electrical panels; tanks; electrorefining tanks; water softener tanks; fuel tanks; filament-wound tanks; filamount-wound tank linings; furniture; garage doors; gratings; protective body gear; luggage; outdoor motor vehicles; pressure tanks; printed circuit boards; optical waveguides; radomes; railings; railroad parts; hopper car covers; car doors; truck bed liners; satellite dishes; signs; solar energy panels; telephone switchgear housings; tractor parts; transformer covers; truck parts; insulation for rotating machines; commutators; core insulation and cords and lacing tape; drive shaft couplings; propeller blades; missile components; rocket motor cases; wing sections; sucker rods; fuselage sections; wing skins; wing flairings; engine narcelles; cargo doors; tennis racquets; golf club shafts; fishing rods; skis; ski poles; bicycle parts; transverse leaf springs; pumps; automotive smog pumps; electrical components; embedding; tooling; electrical cable joints; wire windings; densely packed multi-element assemblies; sealing of electromechanical devices; battery cases; resistors; fuses; thermal cut-off devices; coatings for printed wiring boards; casting items; capacitors; transformers; crankcase heaters; small molded electronic parts; coils; semiconductors; chemical processing parts; pulp and paper machine parts; power generation parts; wastewater treatment parts; scrubbing towers; pultruded parts for structural applications; structural members; gratings; safety rails; swimming pools; swimming pool slides; hot-tubs; saunas; drive shafts for under the hood applications; dry toner resins for copying machines; marine tooling; marine composites; heat shields; submarine hulls; prototype generation parts; laminated trim; drilling fixtures; bonding jigs; inspection fixtures; industrial metal forming dies; aircraft stretch block and hammer forms; vacuum molding tools; flooring; flooring for production and assembly areas; flooring for clean rooms; flooring for machine shops; flooring for control rooms; flooring for laboratories; flooring for parking garages; flooring for freezers; flooring for coolers; flooring for outdoor loading docks; electrically conductive compositions for antistatic applications; decorative flooring; expansion joints for bridges; injectable mortars for patch and repair of cracks in structural concrete; grouting for tile; machinery rails; metal dowels; bolts and posts; repair material for oil and fuel storage tanks; sport equipment; media equipment; grinding wheels; sanding wheels; mechanical rollers; conveyor belts; military equipment; space equipment; aerospace components; automotive components; mass transportation components; printed circuit boards; electrical components; optical components; optoelectrical components; computer components; watercraft exterior components; watercraft interior components; gas storage tanks; and wind turbines.

In certain embodiments, the article is selected from aerospace components, automotive components, mass transportation components, printed circuit boards, electrical components, optical components, optoelectrical components, computer components, watercraft exterior components, and watercraft interior components.

In certain embodiments, the article is produced by resin transfer molding; sheet molding; bulk molding; pultrusion; injection molding; reaction injection molding (RIM); atmospheric pressure molding (APM); casting; centrifugal casting; static casting; open mold casting; lamination; contact molding; cylindrical contact molding; compression molding; vacuum assisted resin transfer molding; chemically assisted resin transfer molding; matched tool molding; autoclave curing; thermal curing in air; vacuum bagging; Seeman's Composite Resin Infusion Manufacturing Processing (SCRIMP); open molding; filament winding; cylindrical filament winding; or a combination thereof.

In another aspect, disclosed is a material comprising the cured composition, wherein the material is a composite, a coating, an adhesive, an encapsulant, or a sealant.

In certain embodiments, the material comprises one or more additional components, each independently selected from flame retardants, fillers, reinforcing fibers, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and combinations thereof.

In certain embodiments, the filler is selected from: alumina, silica, boron nitride aluminum nitride, silicon nitride, magnesia, magnesium silicate, glass fibers, glass mat, silica powder, fumed silica, spherical silica, thiourea, $Al_2O_3$, talc, kaolin, clay, antimony trioxide, glass bubbles, hollow glass microsphere, aramid fibers, and quartz.

In certain embodiments, the composite is a glass fiber based composite, a carbon fiber based composite, or a combination thereof.

In certain embodiments, the material is produced by a resin transfer molding process.

The compounds, compositions, methods, and processes are further described herein.

DETAILED DESCRIPTION

The present disclosure relates to high heat, high purity compounds, methods for preparing the compounds, and curable compositions including the compounds. The disclosure also relates to materials and articles derived from the compounds and curable compositions. The disclosed compounds can be used to produce composites with good thermal and mechanical performance (e.g., high glass transition temperatures (Tg) and ductility), and can be particularly suited for transportation and aerospace applications.

Thermal performance of thermosets has previously been accomplished by increasing the crosslink density of the composite network via multi-functional resins having, for example, three or four reactive functional groups per molecule. Curing these multi-functional resins (e.g., with aromatic amine) results in a thermoset matrix with a very high crosslink density. The highly crosslinked nature of the matrix can, however, lead to an inherent brittleness. The disclosed compounds, by comparison, can provide a thermoset matrix with suitable heat resistance and ductility, without the high crosslink density that leads to brittleness.

The disclosed resins can also provide the advantage of having low viscosities. The low viscosity resins can be used for production of parts via resin transfer molding processes. For example, the resins can be used to obtain a short fill time into a mold containing a glass preform without moving the glass preform. The mold can be isothermal and once the resin enters into the mold it can heat up and start to cure, with a concomitant increase in viscosity. The low viscosity resins can also be used for production of electronic moldings to encapsulate microchips, for example.

The low viscosity of the resins can be at least partially attributed to the high purity of the resins.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" can refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which can also include, in combination, additional elements not listed.

"Acrylatealkyl" as used herein can mean an acrylate appended to the parent molecular moiety through an alkyl, as defined herein. The acrylate can be substituted or unsubstituted. Representative examples of acrylatealkyl include, but are not limited to, $H_2C=CH_2-C(O)O-CH_2-$ and $H_2C=CH(CH_3)-C(O)O-CH_2-$.

"Alkenylalkyl" as used herein can mean an alkene appended to the parent molecular moiety through an alkyl, as defined herein.

"Alkyl" as used herein can mean a linear, branched, or cyclic hydrocarbyl group, such as a methyl group, ethyl group, n-propyl group, isopropyl group, n-butyl group, isobutyl group, tert-butyl group, n-pentyl group, isopentyl group, n-hexyl group, isohexyl group, cyclopentyl group, cyclohexyl group, and the like.

"Alkynylalkyl" as used herein can mean an alkyne appended to the parent molecular moiety through an alkyl, as defined herein.

"Aryl" as used herein can mean a substituted or unsubstituted aryl radical containing from 6 to 36 ring carbon atoms. Examples of aryl include, but are not limited to, a phenyl group, a bicyclic hydrocarbon fused ring system, or a tricyclic hydrocarbon fused ring system wherein one or more of the rings are a phenyl group.

"Arylalkyl" as used herein can mean an aryl, as defined herein, appended to the parent molecular moiety through an alkyl, as defined herein.

"Copolymer" as used herein can mean a polymer derived from two or more structural unit or monomeric species, as opposed to a homopolymer, which is derived from only one structural unit or monomer.

"$C_3$-$C_6$ cycloalkyl" as used herein can mean cyclopropyl, cyclobutyl, cyclopentyl or cyclohexyl.

"Glass Transition Temperature" or "Tg" as used herein can mean the maximum temperature that a polymer or material will have one or more useful properties. These properties include impact resistance, stiffness, strength, and shape retention. The Tg can be measured using a differential scanning calorimetry method and expressed in degrees Celsius.

"Halo" as used herein can be a substituent to which the prefix is attached is substituted with one or more independently selected halogen radicals. For example, "$C_1$-$C_6$ haloalkyl" means a $C_1$-$C_6$ alkyl substituent wherein one or more hydrogen atoms are replaced with independently selected halogen radicals. Non-limiting examples of $C_1$-$C_6$ haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals can be identical or different (unless otherwise stated).

"Halogen" or "halogen atom" as used herein can mean a fluorine, chlorine, bromine or iodine atom.

"Heteroaryl" as used herein can mean any aromatic heterocyclic ring which can comprise an optionally benzocondensed 5 or 6 membered heterocycle with from 1 to 3 heteroatoms selected among N, O or S. Non limiting examples of heteroaryl groups can include pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isooxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

"Hindered phenol stabilizer" as used herein can mean 3,5-di-tert-butyl-4-hydroxyhydrocinnamic acid, octadecyl ester.

"Hydrocarbyl" as used herein refers to a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; arylalkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like.

"Hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

"PETS release agent" as used herein can mean pentaerythritol tetrastearate, mold release.

"Phosphite stabilizer" as used herein can mean tris-(2,4-di-tert-butylphenyl) phosphite.

"Straight or branched $C_1$-$C_3$ alkyl" or "straight or branched $C_1$-$C_3$ alkoxy" as used herein can mean methyl, ethyl, n-propyl, isopropyl, methoxy, ethoxy, n-propoxy and isopropoxy.

Unless otherwise indicated, each of the foregoing groups can be unsubstituted or substituted, provided that the substitution does not significantly adversely affect synthesis, stability, or use of the compound.

The terms "structural unit" and "monomer" are interchangeable as used herein.

"Thermal stability" as used herein refers to resistance of a polymer to molecular weight degradation under thermal conditions. Thus, a polymer with poor thermal stability can show significant molecular weight degradation under thermal conditions, such as during extrusion, molding, thermoforming, hot-pressing, and like conditions. Molecular weight degradation can also be manifest through color formation and/or in the degradation of other properties such as weatherability, gloss, mechanical properties, and/or thermal properties. Molecular weight degradation can also cause significant variation in processing conditions such as melt viscosity changes.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Disclosed are compounds (also referred to herein as monomers) useful for preparation of thermoset or thermoplastic compositions. The monomers can be used to impart heat resistance to materials and articles derived from compositions comprising the monomers.

The compounds can have a purity of greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, greater than or equal to 99.1%, greater than or equal to 99.2%, greater than or equal to 99.3%, greater than or equal to 99.4%, greater than or equal to 99.5%, greater than or equal to 99.6%, greater than or equal to 99.7%, greater than or equal to 99.8%, or greater than or equal to 99.9%, as determined by high performance liquid chromatography (HPLC).

The compounds can have a metal impurity content of 3 ppm or less, 2 ppm or less, 1 ppm or less, 500 ppb or less, 400 ppb or less, 300 ppb or less, 200 ppb or less, or 100 ppb or less. The metal impurities can be iron, calcium, zinc, aluminum, or a combination thereof. The compounds can have an unknown impurities content of 0.1 wt % or less. The compounds can have a color APHA value of 40 or less, 35 or less, 30 or less, 25 or less, 20 or less, 19 or less, 18 or less, 17 or less, 16 or less, or 15 or less, as measured using test method ASTM D1209.

The disclosed compounds can have formula (I)-(IX):

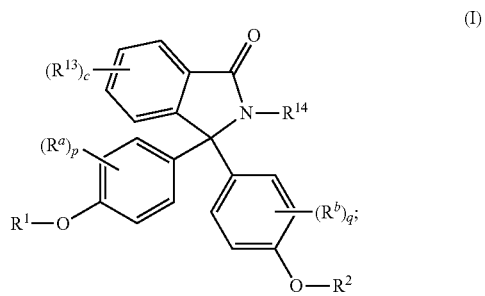

(I)

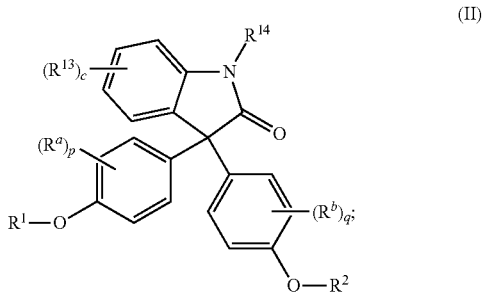

(II)

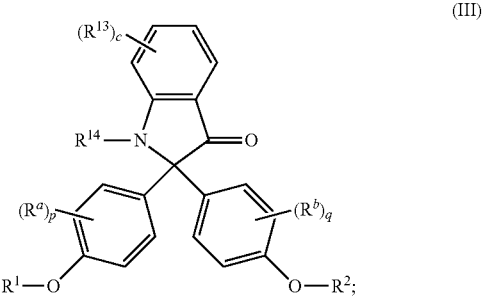

(III)

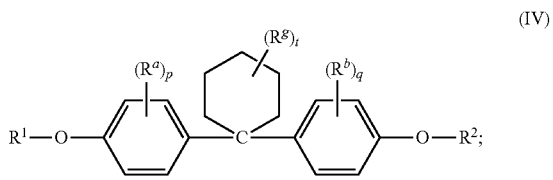

(IV)

-continued

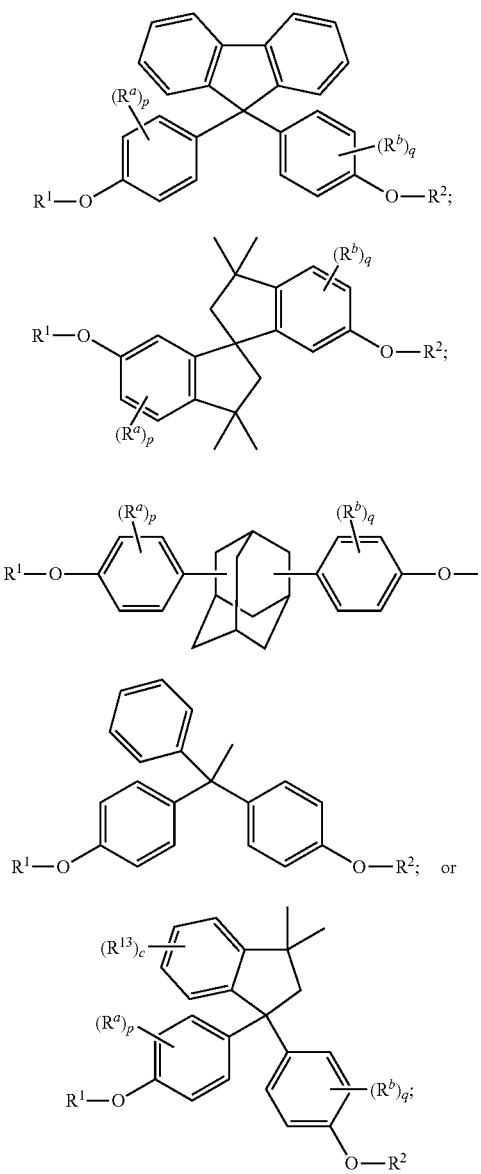

(V)

(VI)

(VII)

(VIII)

(IX)

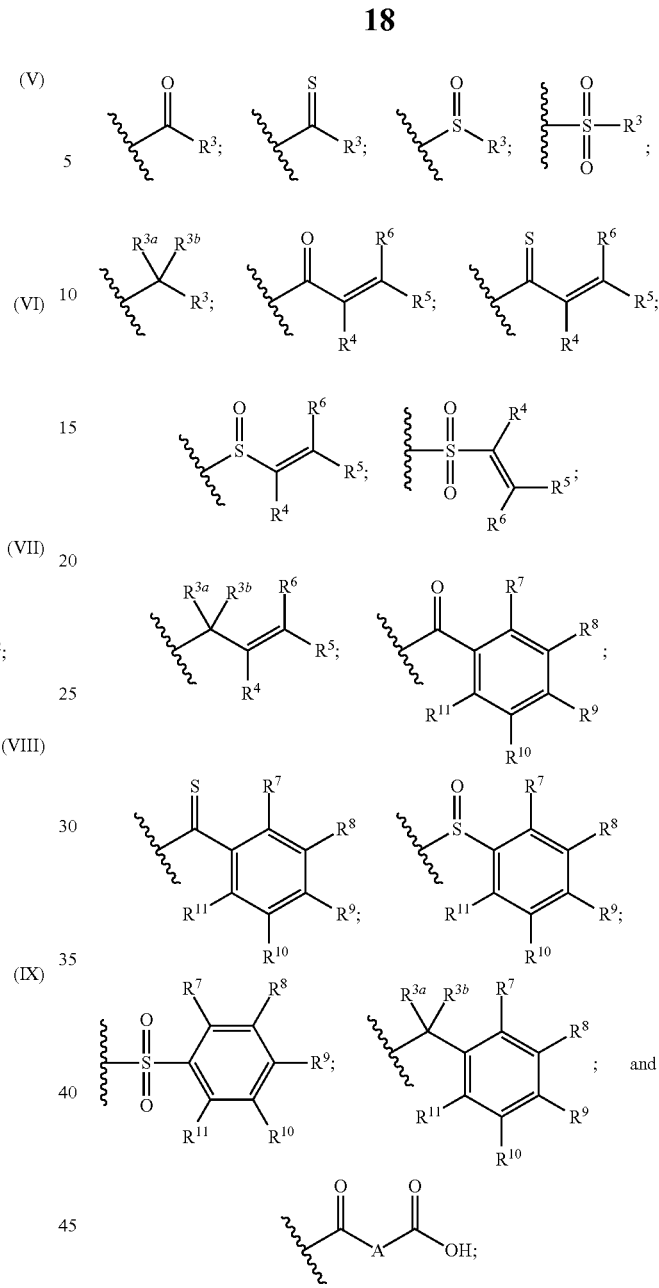

wherein $R^1$ and $R^2$ at each occurrence are each independently selected from a reactive functional group; $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

In certain embodiments, $R^1$ and $R^2$ at each occurrence are each independently selected from: cyano; haloalkyl (e.g., halo-$C_1$-$C_{12}$-alkyl); alkenyl (e.g., $C_2$-$C_{12}$ alkenyl); alkenylalkyl (e.g., $C_1$-$C_{12}$-alkyl-$C_2$-$C_{12}$ alkenyl); alkynylalkyl (e.g., $C_1$-$C_{12}$-alkyl-$C_2$-$C_{12}$ alkynyl); hydroxyalkyl (e.g., —$C_1$-$C_{12}$-alkyl-OH); acrylatealkyl (e.g., —$C_1$-$C_{12}$-alkyl-O-acroyl);

wherein $R^3$, at each occurrence, is independently selected from $C_1$-$C_{12}$ alkyl, heteroaryl, alkoxy (e.g., $C_1$-$C_{12}$ alkoxy), amino, and alkylamino (e.g., $C_1$-$C_{12}$ alkylamino); $R^4$-$R^6$ are each independently selected from hydrogen, $C_1$-$C_{12}$ alkyl, $C_2$-$C_{12}$ alkenyl, $C_6$-$C_{18}$ aryl, $C_7$-$C_{18}$ alkyl-substituted aryl, $C_7$-$C_{18}$ aryl-substituted alkyl, $C_2$-$C_{12}$ alkoxycarbonyl, $C_7$-$C_{18}$ aryloxycarbonyl, $C_8$-$C_{18}$ alkyl-substituted aryloxycarbonyl, $C_8$-$C_{18}$ aryl-substituted alkoxycarbonyl, nitrile, formyl, carboxylate, imidate, and thiocarboxylate; $R^7$-$R^{11}$ are each independently selected from hydrogen, halogen, $C_1$-$C_{12}$ alkyl, $C_2$-$C_{12}$ alkenyl, hydroxy, and amino; $R^{3a}$ and $R^{3b}$ are each independently selected from hydrogen and $C_1$-$C_{12}$ alkyl; and A at each occurrence is independently selected from a saturated or unsaturated $C_2$-$C_{12}$ divalent hydrocarbon group.

In certain embodiments, $R^1$ and $R^2$ are each independently selected from:

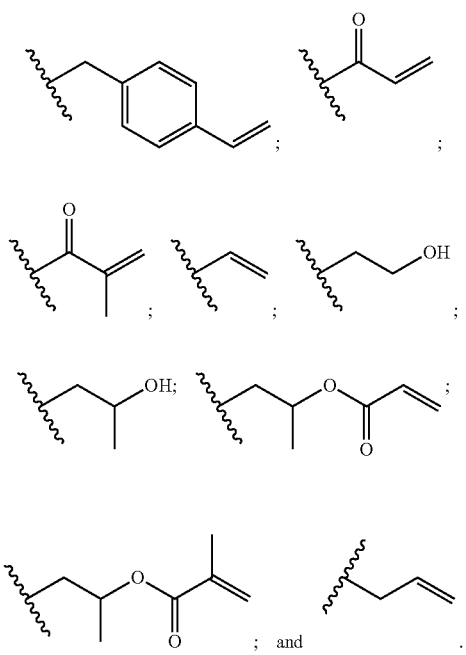

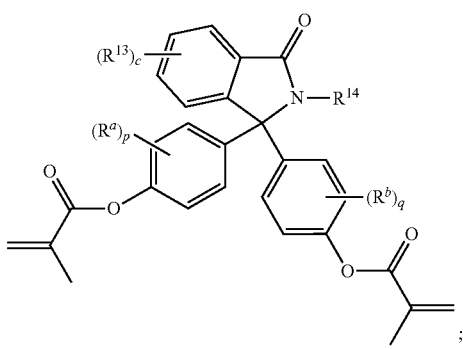

In certain embodiments, the disclosed compounds are substantially free of oligomer impurities. The compounds can have an oligomer impurity content of less than or equal to 3%, less than or equal to 2%, less than or equal to 1%, less than or equal to 0.5%, less than or equal to 0.4%, less than or equal to 0.3%, less than or equal to 0.2%, or less than or equal to 0.1%, as determined by high performance liquid chromatography.

The compounds can have formula (1)-(9), or a combination thereof,

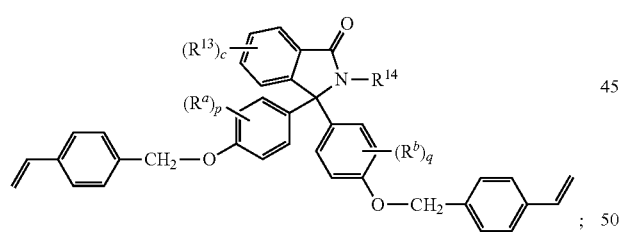

(1)

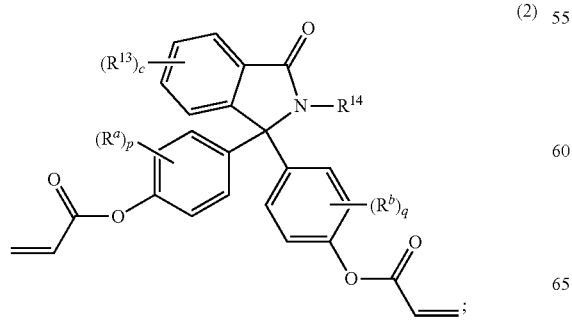

(2)

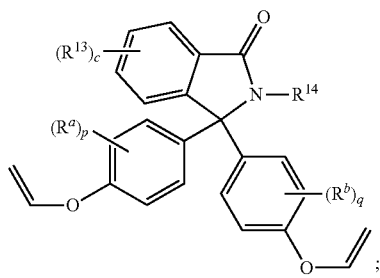

(3)

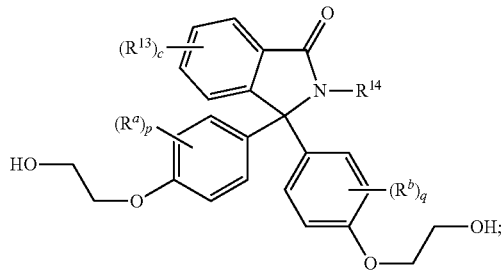

(4)

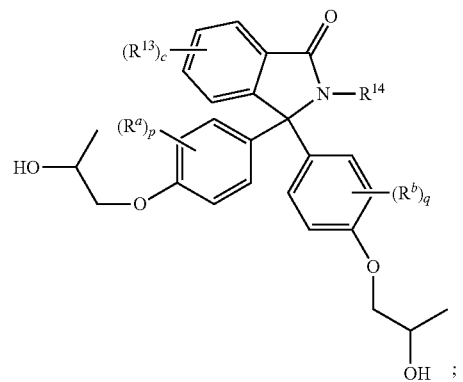

(5)

(6)

-continued

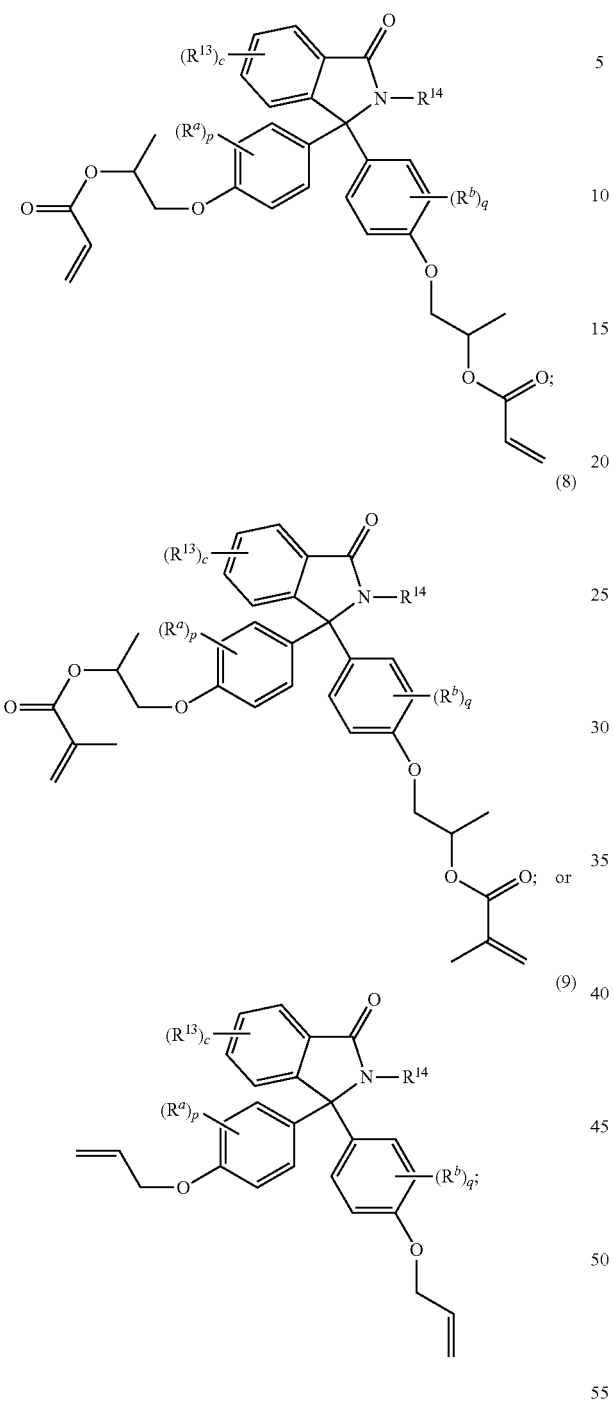

wherein R$^a$ and R$^b$ at each occurrence are each independently halogen, C$_1$-C$_{12}$ alkyl, C$_2$-C$_{12}$ alkenyl, C$_3$-C$_8$ cycloalkyl, or C$_1$-C$_{12}$ alkoxy; p and q at each occurrence are each independently 0 to 4; R$^{13}$ at each occurrence is independently a halogen or a C$_1$-C$_6$ alkyl group; c at each occurrence is independently 0 to 4; and R$^{14}$ at each occurrence is independently a C$_1$-C$_6$ alkyl, phenyl, or phenyl substituted with up to five halogens or C$_1$-C$_6$ alkyl groups.

The compounds can have formula (1-a), (2-a), (3-a), (4-a), (4-b), (4-c), (5-a), (6-a), (7-a), (8-a), (9-a), (10-a) or a combination thereof,

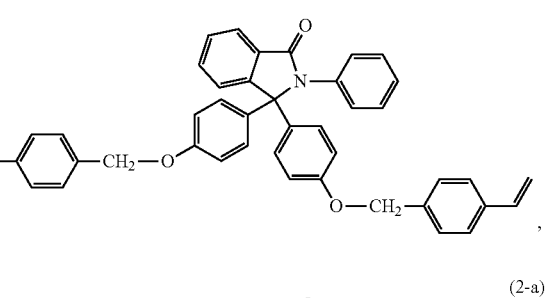

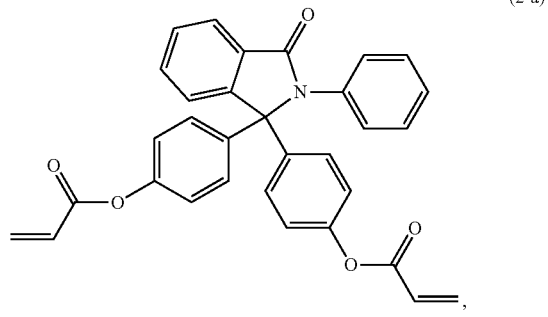

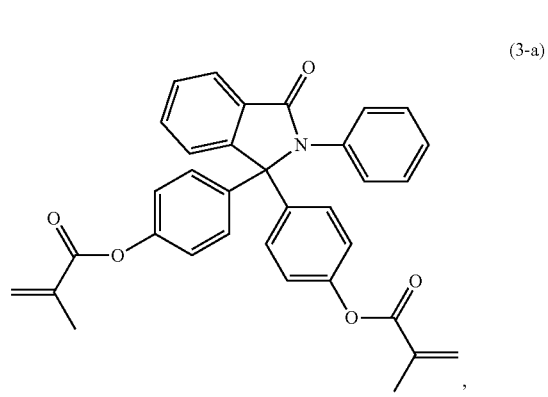

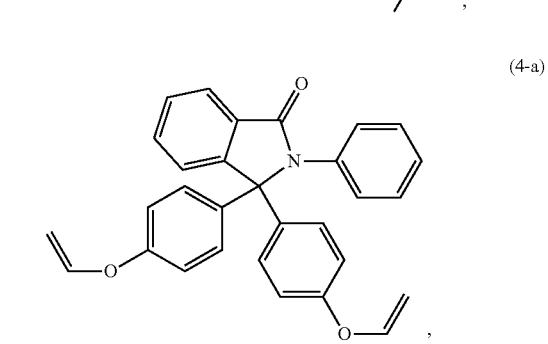

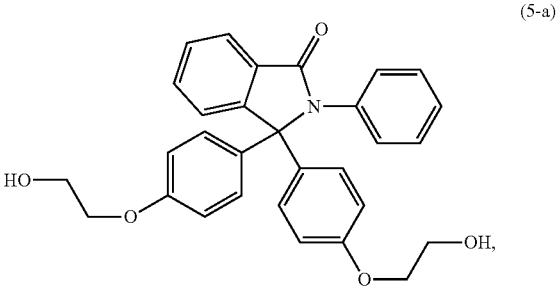

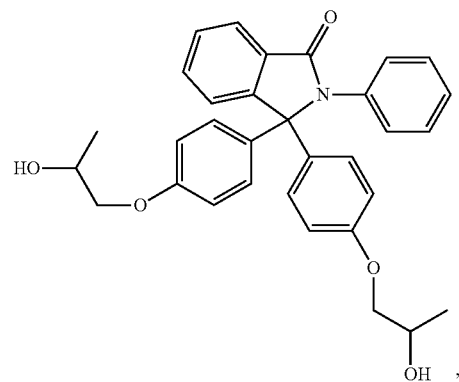
(6-a)
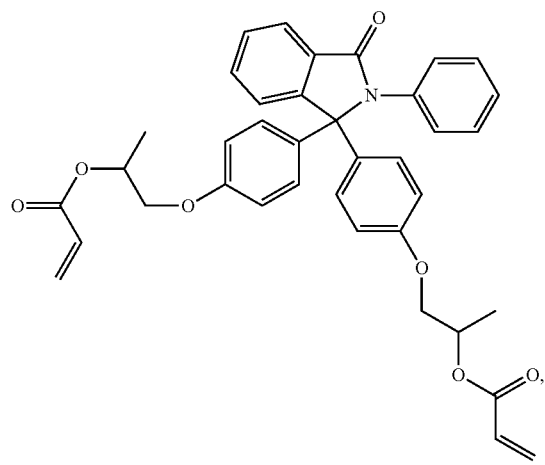
(7-a)
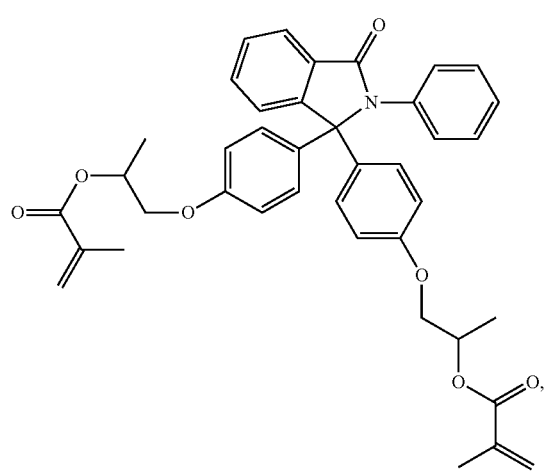
(8-a)
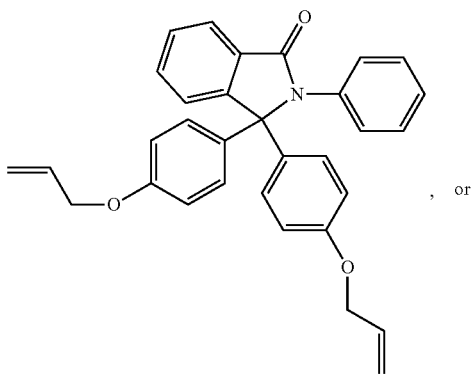
(9-a)
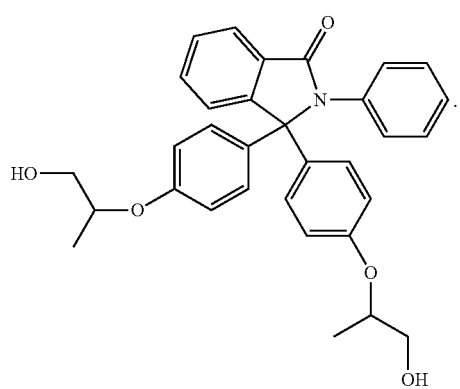
(10-a)
The compounds can be derived from a corresponding bisphenol. The compounds can be derived from a bisphenol of formula (1')-(9'), or a combination thereof,
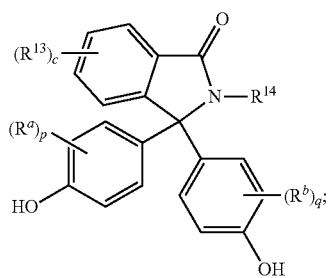
(1')
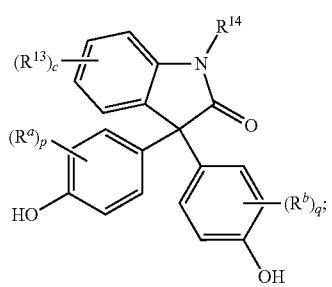
(2')

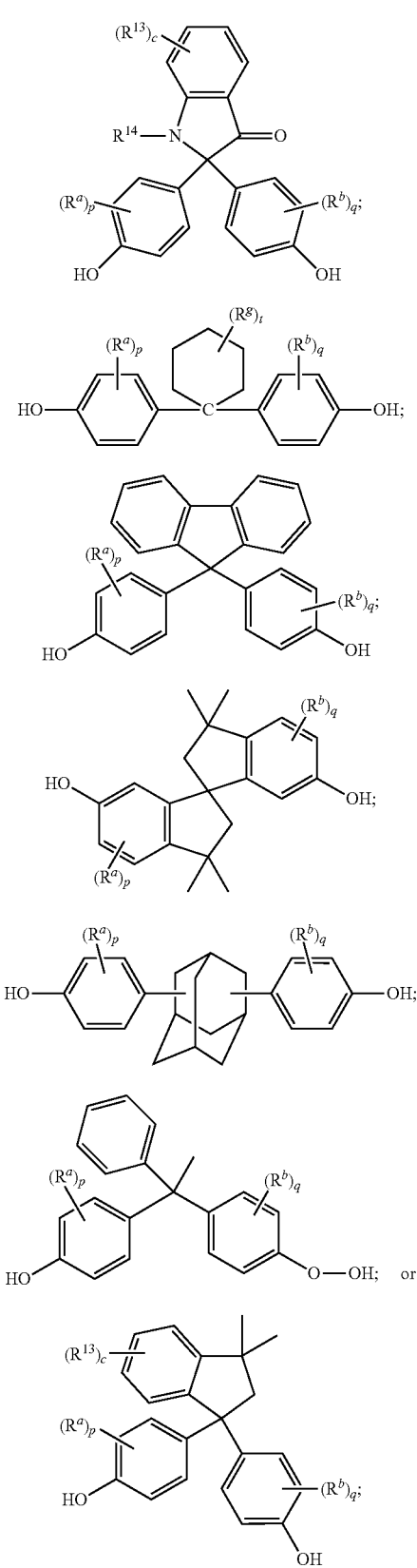

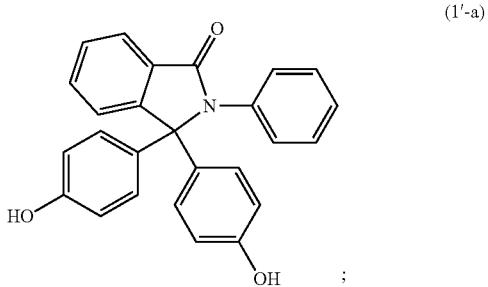 [SMILES: O=C1c2ccccc2C(c2ccc(O)cc2)(c2ccc(O)cc2)N1c1ccccc1]

cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; $R^{14}$ at each occurrence is independently a $C_1$-$C_6$ alkyl, phenyl, or phenyl substituted with up to five halogens or $C_1$-$C_6$ alkyl groups; $R^g$ at each occurrence is independently $C_1$-$C_{12}$ alkyl or halogen, or two $R^g$ groups together with the carbon atoms to which they are attached form a four-, five, or six-membered cycloalkyl group; and t is 0 to 10.

The compounds can be derived from a bisphenol of formula (1'-a), (2'-a), (3'-a), (4'-a), (4'-b), (4'-c), (5'-a), (6'-a), (7'-a), (8'-a), (9'-a), or a combination thereof,

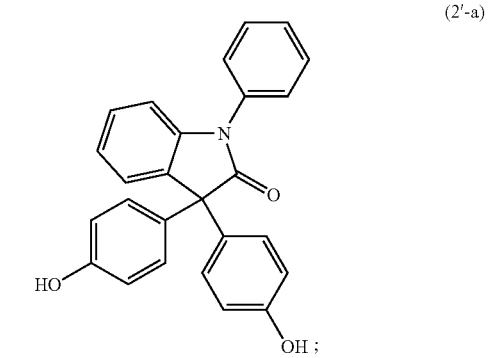

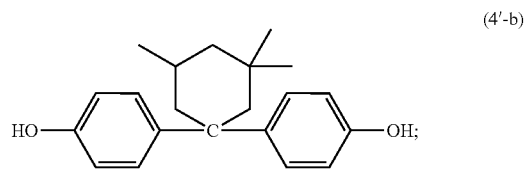

wherein $R^a$ and $R^b$ at each occurrence are each independently halogen, $C_1$-$C_{12}$ alkyl, $C_2$-$C_{12}$ alkenyl, $C_3$-$C_8$

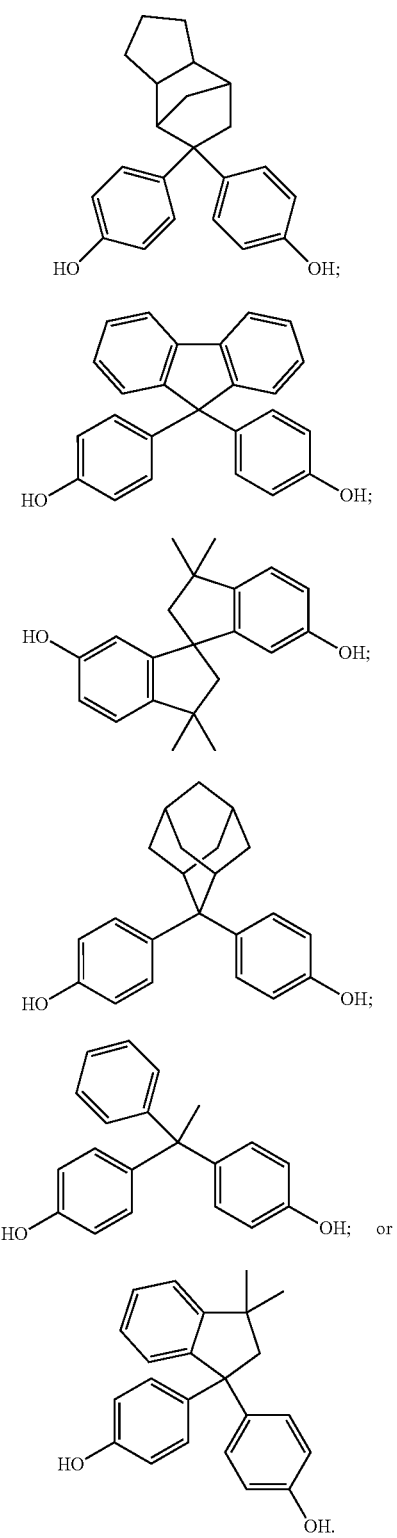

The bisphenols can have a purity of 97% or greater, 98% or greater, 99% or greater, 99.5% or greater, 99.8% or greater, 99.90% or greater, or 99.95% or greater. The bisphenols can have an aminophenol impurity content of 200 ppm or less, 150 ppm or less, 100 ppm or less, 90 ppm or less, 80 ppm or less, 70 ppm or less, 60 ppm or less, 50 ppm or less, 40 ppm or less, 30 ppm or less, 20 ppm or less, or 10 ppm or less. The amino phenol impurity can be 2-phenyl-3-(4-aminophenyl)-3-(4-hydroxyphenyl)phthalimidine. The bisphenols can have a phenolphthalein impurity content of 1,000 ppm or less, 750 ppm or less, 500 ppm or less, 400 ppm or less, 300 ppm or less, 200 ppm or less, 100 ppm or less, 50 ppm or less. The bisphenols can have a metal impurity content of 3 ppm or less, 2 ppm or less, 1 ppm or less, 500 ppb or less, 400 ppb or less, 300 ppb or less, 200 ppb or less, or 100 ppb or less. The metal impurities can be iron, calcium, zinc, aluminum, or a combination thereof. The bisphenols can have an unknown impurities content of 0.1 wt % or less. The bisphenols can have a color APHA value of 40 or less, 35 or less, 30 or less, 25 or less, 20 or less, 19 or less, 18 or less, 17 or less, 16 or less, or 15 or less, as measured using test method ASTM D1209.

The disclosed compounds can be prepared from a corresponding bisphenol compound [e.g., a bisphenol of formula (1')-(9')]. The bisphenol can be provided in a mixture with a source of the $R^1$ and $R^2$ groups.

The isolated product can be obtained in a yield of 80% or greater, 85% or greater, or 90% or greater.

The purity of the isolated product can be greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, greater than or equal to 99.1%, greater than or equal to 99.2%, greater than or equal to 99.3%, greater than or equal to 99.4%, greater than or equal to 99.5%, greater than or equal to 99.6%, greater than or equal to 99.7%, greater than or equal to 99.8%, or greater than or equal to 99.9%, as determined by high performance liquid chromatography (HPLC). The isolated product can be substantially free of oligomeric impurities.

Also disclosed are compositions including the disclosed high heat compounds. The compositions can be curable (thermoset) compositions. The compositions can be thermoplastic compositions.

The disclosed compounds can blended with one or more additional components to provide the compositions. For example, the compositions can further include curing promoters, auxiliary co-monomers, flame retardants, fillers, reinforcing fibers, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and a combination thereof. The compositions can include one or more homopolymer and copolymer components (e.g., polycarbonates, polysiloxanes, polyphenylene ethers, polysiloxane-polycarbonate copolymers, polyester-polycarbonate copolymers).

The compositions (e.g., curable compositions) can include the disclosed high heat compounds in an amount of 1 wt % to 99.9 wt %, 3 wt % to 50 wt %, 5 wt % to 40 wt %, or 10 wt % to 30 wt %, based on total weight of the curable composition.

The curable compositions, when cured, can have a Tg of greater than or equal to 145° C., greater than or equal to 150° C., greater than or equal to 155° C., greater than or equal to 160° C., greater than or equal to 165° C., greater than or equal to 170° C., greater than or equal to 175° C., greater than or equal to 180° C., greater than or equal to 185° C., greater than or equal to 190° C., greater than or equal to 200°

C., greater than or equal to 210° C., greater than or equal to 220° C., greater than or equal to 230° C., greater than or equal to 240° C., greater than or equal to 250° C., greater than or equal to 260° C., greater than or equal to 270° C., greater than or equal to 280° C., greater than or equal to 290° C., or greater than or equal to 300° C., as measured using a differential scanning calorimetry method. Differential scanning calorimetry (DSC) can be conducted with a heating rate of 10° C./minute or 20° C./minute. The cured composition can exhibit a single Tg, as opposed to two or more Tgs, indicating that the monomer is covalently bound to the resin matrix of the cured composition. In other words, the compound may not exist as a separate phase within the resin matrix. Depending on the type and relative amounts of components and curing promoters, the glass transition can range from 100° C. to 300° C., or 150° C. to 200° C., for example.

The cured compositions can exhibit good impact strength. In some embodiments, the cured composition exhibits an unnotched Izod impact strength of at least 400 joules per meter, specifically 400 to 600 joules per meter, more specifically 450 to 550 joules per meter, and still more specifically 480 to 520 joules per meter, as measured at 23° C. with a hammer energy of 2 foot-pounds in accordance with ASTM D 4812.

The cured compositions can exhibit good ductility. The cured compositions can exhibit good fracture toughness, unnotched Izod impact strength, and good tensile elongation.

The cured compositions can exhibit increased char formation on pyrolysis.

The cured compositions can exhibit low moisture absorption.

The cured compositions can exhibit decreased shrinkage upon curing.

The cured compositions can exhibit decreased dielectric properties.

The cured compositions can exhibit a dielectric constant of 2.8 to 3.2, specifically 2.9 to 3.1, and more specifically, 3.00 to 3.06, as measured at 1,000 megahertz in accordance with IPC-TM-650 2.5.5.9.

The cured compositions can exhibit a loss tangent of 0.011 to 0.017, specifically 0.012 to 0.016, and more specifically 0.013 to 0.015, as measured at 1,000 megahertz in accordance with IPC-TM-650 2.5.5.9.

The cured compositions can exhibit a water absorption of less than or equal to 5 weight percent (wt %), specifically less than or equal to 4 wt, more specifically less than or equal to 3 wt %, and still more specifically less than or equal to 2 wt %, measured after immersion in deionized water at 80° C. for 250 hours.

The cured composition can preferably exhibit a coefficient of thermal expansion (CTE) below its Tg of not greater than 30 micrometer/meter-° C. (µm/m-° C.), preferably not greater than 25 µm/m-° C., more preferably not greater than 20 µm/m-° C.

The cured compositions can exhibit a number of additional advantageous properties simultaneously.

Curing promoters or agents are used as reaction initiators. Curing promoters can be included for the purpose of enhancing the advantageous effect of the cross-linking vinyl components. Although the presence of vinyl monomers and unsaturated components alone can advance curing at high temperature, it is desirable to add the curing catalyst or reaction initiator as it is sometimes difficult to keep high temperature until the curing is completed depending on the process conditions.

The "reaction initiator" is not particularly limited if it can accelerate curing of the vinyl monomer and auxiliary vinyl co-monomer compositions at a suitable temperature and within a suitable period, and increase the characteristics such as heat resistance or the like of cured composition. The curing agent for the unsaturated portion of the thermosets would include any compound capable of producing radicals at elevated temperatures or at room temperature. Such curing catalysts would include both peroxy and non-peroxy based radical initiators. The use of cross linking agents and initiators is well known in the art and described in detail in U.S. Pat. No. 6,352,782B2 and U.S. Pat. No. 5,352,745. Suffice it to say that the initiator plays a significant part in the effectiveness of the cross linking agent.

Examples of useful peroxy initiators include cumene hydroperoxide, 2,5-dimethylhexane-2,5-dihydroperoxide, 2,5-dimethylhexane-2,5-dihydroperoxide, α,α-bis(t-butylperoxy-m-isopropyl)benzene, dicumyl peroxide, di(trimethylsilyl)peroxide, trimethylsilyl triphenylsilyl peroxide, 2,5-dimethyl-2,5-di(t-butylperoxy) hexane (DHBP, also refers to Perhexa 25B), 2,5-dimethyl-2,5-di(t-butylperoxy)-hex-3-yne (DYBP, also refers to Perhexyne 25B, made by a Japanese firm Nippon Yushi K. K.), di-t-butylperoxide (DTBP), t-butylcumyl peroxide, dicumyl peroxide (DCP), di(t-butylperoxy isophthalate), t-butylperoxybenzoate, 2,2-bis(t-butylperoxy)butane, 2,2-bis(t-butylperoxy) octane, 2,5-dimethyl-2,5-di(benzoylperoxy)hexane, di(trimethylsilyl) peroxide, trimethylsilylphenyltriphenylsilyl peroxide, α,α'-bis(t-butylperoxy-m-isopropyl)benzene, 1,3-di(2-tert-butylperoxy isopropyl)benzene (DIPP), benzoyl peroxide (BPO), 3,3',5,5'-tetramethyl-1,4-diphenoxyquinone, chloranil, 2,4,6-tri-t-butylphenoxyl, t-butylperoxyisopropylmonocarbonate, and azobisisobutyronitrile.

In certain embodiments, the curing reaction can further accelerated by further adding a metal carboxylate salt. Among them, α,α'-bis(t-butylperoxy-m-isopropyl)benzene is particularly preferable as the reaction initiator. It is because the compound has a relatively high reaction initiation temperature, thus not initiating curing when the curing is not required, for example, during prepreg drying, and not impairing the storage stability of the vinyl monomer compositions; a low volatility, preventing vaporization during prepreg drying and storage; and thus an excellent stability.

The curing initiator can further include any compound capable of initiating anionic polymerization of the unsaturated components. Such anionic polymerization initiators include, for example, alkali metal amides such as sodium amide ($NaNH_2$) and lithium diethyl amide ($LiN(C_2H_5)_2$), alkali metal and ammonium salts of C1-C10 alkoxides, alkali metal hydroxides, ammonium hydroxides, alkali metal cyanides, organometallic compounds such as the alkyl lithium compound n-butyl lithium, Grignard reagents such as phenyl magnesium bromide, and the like, and a combination thereof. Especially, the curing initiator can comprise 2,5-bis-(t-butyl peroxy)-2,5-dimethyl-3-hexane or dicumyl peroxide. The curing initiator can promote curing at a temperature in a range of 0° C. to 200° C.

In some example, a high molecular weight polyperoxide material is used as an initiator.

The high molecular weight polyperoxide has a molecular weight in excess of 1,000 and preferably in excess of 3,000. A particularly useful polyperoxide initiator, a polyperoxide functionalized polystyrene with the decomposition products thereof:

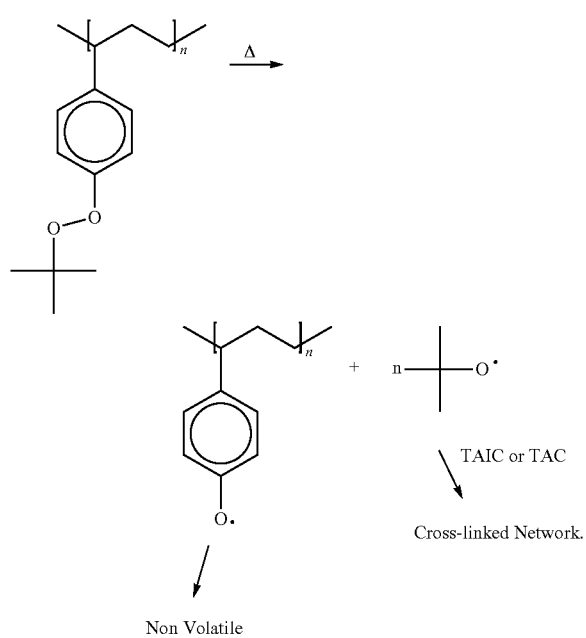

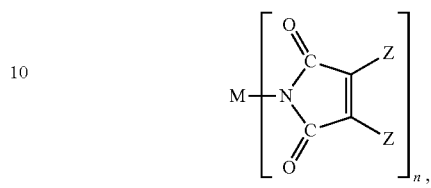

Non Volatile

The particular peroxidized polystyrene has a molecular weight in excess of 1,000 and preferably in excess of 3,000.

The following figure depicts a general structure of a peroxide functionalized polymer that can be used. A polymer can be functionalized to incorporate peroxide groups in pendant side chains or at the end groups:

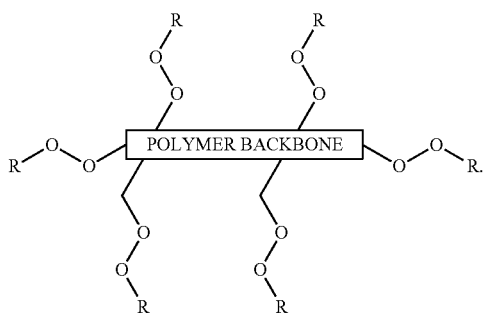

A generalized polymer structure that has been functionalized with peroxide groups is as follows:

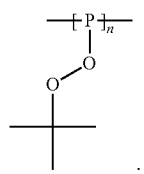

These particular polymers could be polystyrene, as indicated above, or polyethylene, polypropylene, polybutylene, and polymethacrylate. As shown above, these polyfunctionalized structures will break at the oxygen-oxygen bond and provide the active radical moiety, such as t-butoxide, to initiate polymerization, and the remaining inert moiety which has a molecular weight greater than 1,000.

Typical non-peroxy initiators include compounds such as 2,3-dimethyl-2,3-diphenylbutane, 2,3-trimethylsilyloxy-2,3-diphenylbutane, and a combination thereof.

The auxiliary co-monomer can be a maleimide resin. Suitable maleimides include those having the structure

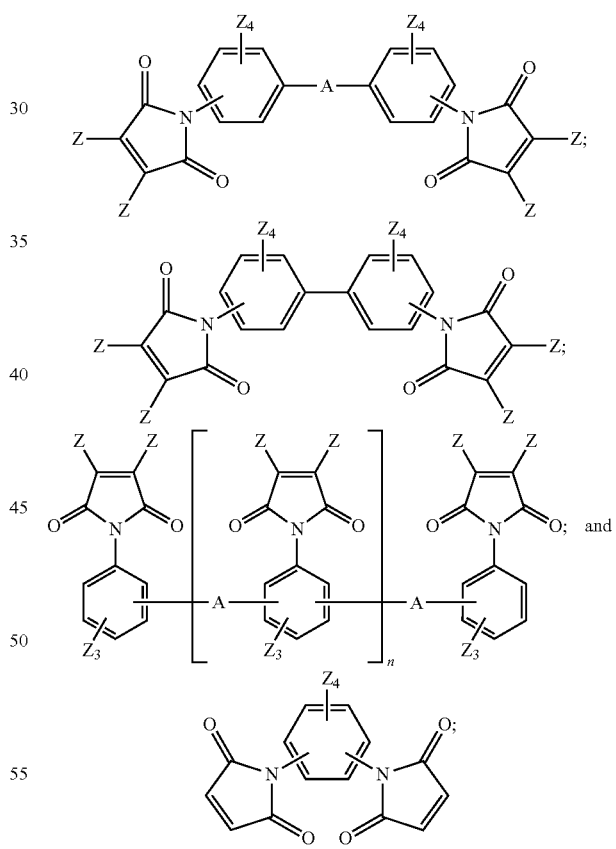

wherein M is a radical and having a valence n and containing 2 to 40 carbon atoms and
optionally one or more heteroatoms; each occurrence of Z is independently hydrogen, halogen, or C1-C18 hydrocarbyl; and n is 1 to 10, specifically 2 or 3 or 4. M can be, for example, aliphatic, cycloaliphatic, aromatic, or heterocyclic.

Suitable maleimides include those represented by the structures wherein each occurrence of Z is independently hydrogen, C1-C18 hydrocarbyl, or halogen; A is C1-C18 hydrocarbylene, oxy, sulfone, sulfinyl, carboxylate, carbonyl, carbonamide, or sulfide; and n is 0 to 10.

Specific examples of maleimide resins include 1,2-bis-maleimidoethane, 1,6-bismaleimidohexane, 1,3-bismaleimidobenzene, 1,4-bismaleimidobenzene, 2,4-bismaleimidotoluene, 4,4'-bismaleimidodiphenylmethane, 4,4'- bismaleimidodiphenylether, 3,3'-bismaleimidodiphenylsulfone, 4,4'-bismaleimidodiphenylsulfone, 4,4'-bismaleimidodicyclohexylmethane, 3,5-bis(4-maleimidophenyl)pyridine, 2,6-bismaleimidopyridine, 1,3-bis(maleimidomethyl)cyclohexane, 1,3-bis(maleimidomethyl)benzene, 1,1-bis(4-maleimidophenyl)cyclohexane, 1,3-bis(dichloromaleimido)benzene, 4,4'-bis(citraconimido)diphenylmethane, 2,2-bis(4-maleimidophenyl)propane, 1-phenyl-1,1-bis(4-maleimidophenyl)ethane, α,α-bis(4-maleimidophenyl)toluene, 3,5-bismaleimido-1,2,4-triazole, N,N'-ethylenebismaleimide, N,N'-hexamethylenebismaleimide, N,N'-m-phenylenebismaleimide, N,N'-p-phenylenebismaleimide, N,N'-4,4'-diphenylmethanebismaleimide, N,N'-4,4'-diphenyletherbismaleimide, N,N'-4,4'-diphenylsufonebismaleimide, N,N'-4,4'-dicyclohexylmethanebismaleimide, N,N'-α,α'-4,4'-dimethylenecyclohexanebismaleimide, N,N'-m-methaxylenebismaleimide, N,N'-4,4'-diphenylcyclohexanebismaleimide, and N,N'-methylenebis(3-chloro-p-phenylene)bismaleimide, as well as the maleimide resins disclosed in U.S. Pat. Nos. 3,562,223, 4,211,860 and 4,211,861.

The maleimide resin can be prepared by methods known in the art, such as contacting 0.1 to 0.8 mole of the chain-extending agent with each mole of the bisimide in an organic solvent at a temperature of 40 to 200° C. for a time of 5 minutes to 5 hours. The maleimide resin can be, for example, a hydrazide-modified bismaleimide as described in U.S. Pat. Nos. 4,211,860 and 4,211,861. Suitable N,N'-unsaturated bismaleimide resins are commercially available from Technochemie GmbH as Compimide resins. The maleimide resin can be a combination of maleimide resins tailored to meet specific processing requirements.

The auxiliary co-monomer can be a benzoxazine resin. Suitable benzoxazine resins include those having the structure:

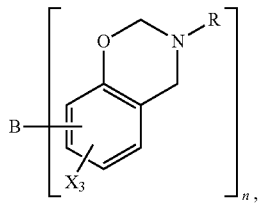

wherein B is a linear or branched hydrocarbon group having 1 to 80 carbon atoms, specifically 1 to 10 carbon atoms (in some embodiments, B is an alkyl group, a cycloalkyl group, carbonyl, sulfonyl, sulfinyl, sulfide, oxy, alkylphosphonyl, arylphosphonyl, isoalkylidene, cycloalkylidene, arylalkylidene, diarylmethylidene, methylidene dialkylsilanyl, arylalkylsilanyl, or diarylsilanyl); n is 1 to 20, specifically 1, 2, 3, or 4, more specifically 2; and X is hydrogen, C1-C18 hydrocarbyl optionally substituted with one or more fluorine atoms, or C1-C40 hydrocarbyl amine (including polyamines). Depending on whether phenolic or phenoxy repeat units are desired in the polybenzoxazine, it can be desirable that at least one non-hydrogen X substituent be ortho, meta, or para to the oxygen atom of the benzoxazine.

As is well known, benzoxazine monomers are made from the reaction of aldehydes, phenols, and primary amines with or without solvent. U.S. Pat. No. 5,543,516 describes a solventless method of forming benzoxazine monomers. An article by Ning and Ishida in Journal of Polymer Science, Chemistry Edition, vol. 32, page 1121 (1994) describes a procedure using a solvent. The procedure using solvent is generally common to the literature of benzoxazine monomers. Suitable phenolic compounds include phenols and polyphenols. The use of polyphenols with two or more hydroxyl groups reactive in forming benzoxazines can result in branched and/or crosslinked products. The groups connecting the phenolic groups into a phenol can be branch points or connecting groups in the polybenzoxazine.

Phenols suitable for use in the preparation of benzoxazine monomers include phenol, cresol, resorcinol, catechol, hydroquinone, 2-allylphenol, 3-allylphenol, 4-allylphenol, 2,6-dihydroxynaphthalene, 2,7-dihydrooxynapthalene, 2-(diphenylphosphoryl)hydroquinone, 2,2'-biphenol, 4,4-biphenol, 4,4'-isopropylidenediphenol (bisphenol A), 4,4'-isopropylidenebis(2-methylphenol), 4,4'-isopropylidenebis(2-allylphenol), 4,4'(1,3-phenylenediisopropylidene)bisphenol (bisphenol M), 4,4'-isopropylidenebis(3-phenylphenol) 4,4'-(1,4-phenylenediisoproylidene)bisphenol (bisphenol P), 4,4'-ethylidenediphenol (bisphenol E), 4,4'-oxydiphenol, 4,4'-thiodiphenol, 4,4'-sulfonyldiphenol, 4,4'-sulfinyldiphenol, 4,4'-hexafluoroisoproylidenebisphenol (Bisphenol AF), 4,4'-(1-phenylethylidene)bisphenol (Bisphenol AP), bis(4-hydroxyphenyl)-2,2-dichloroethylene (Bisphenol C), bis(4-hydroxyphenyl)methane (Bisphenol-F), 4,4'-(cyclopentylidene)diphenol, 4,4'-(cyclohexylidene) diphenol (Bisphenol Z), 4,4'-(cyclododecylidene)diphenol 4,4'-(bicyclo[2.2.1]heptylidene)diphenol, 4,4'-(9H-fluorene-9,9-diyl)diphenol, isopropylidenebis(2-allylphenol), 3,3-bis(4-hydroxyphenyl)isobenzofuran-1(3H)-one, 1-(4-hydroxyphenyl)-3,3-dimethyl-2,3-dihydro-1H-inden-5-ol, 3,3,3',3'-tetramethyl-2,2',3,3'-tetrahydro-1,1'-spirobi[indene]-5,6'-diol (spirobiindane), dihydroxybenzophenone (bisphenol K), tris(4-hydroxyphenyl)methane, tris(4-hydroxyphenyl)ethane, tris(4-hydroxyphenyl)propane, tris(4-hydroxyphenyl)butane, tris(3-methyl-4-hydroxyphenyl)methane, tetrakis(4-hydroxyphenyl)ethane dicyclopentadienylbis(2,6-dimethyl phenol), dicyclopentadienyl bis(ortho-cresol), and dicyclopentadienyl bisphenol.

The aldehyde used to form the benzoxazine can be any aldehyde. In some embodiments, the aldehyde has 1 to 10 carbon atoms. In some embodiments, the aldehyde is formaldehyde. The amine used to form the benzoxazine can be an aromatic amine, an aliphatic amine, an alkyl substituted aromatic, or an aromatic substituted alkyl amine. The amine can also be a polyamine, although the use of polyamines will, under some circumstances, yield polyfunctional benzoxazine monomers. Polyfunctional benzoxazine monomers are more likely to result in branched and/or crosslinked polybenzoxazines than monofunctional benzoxazines, which would be anticipated to yield thermoplastic polybenzoxazines.

The amines generally have 1 to 40 carbon atoms unless they include aromatic rings, and then they can have 6 to 40 carbon atoms. The amine of a di- or polyfunctional amine can also serve as a branch point to connect one polybenzoxazine to another. Thermal polymerization has been the preferred method for polymerizing benzoxazine monomers. The temperature to induce thermal polymerization is typically varied from 150 to 300° C. The polymerization is typically performed in bulk, but can also be performed in solution. Catalysts, such as carboxylic acids, have been known to slightly lower the polymerization temperature or accelerate the polymerization rate at the same temperature.

Cationic polymerization initiators have been found to result in polymerization of benzoxazine monomers at temperatures as low as cryogenic temperatures. Preferred temperatures are −100 to 250° C., specifically −60 to 150° C. for ease of handling the reactants and products. Some of the cationic initiators, for example PCl5, form repeating units from the benzoxazine monomers that include a salt of the amine. These repeating units have better solubility in polar solvents, such as water, than similar repeating units without the amine salt. The initiators can be used either in the benzoxazine melt or in the presence of solvent, allowing the solvent content to be from 0 to nearly 100%. Many solvents can be used in cationic polymerizations, and their selection is known by those skilled in the art of cationic polymerization.

The polymers from the cationically initiated polymerization of benzoxazine are useful as molded articles with good thermal stability and/or flame resistance, such as molded circuit boards, flame resistant laminates, or other molded articles, and is a source of precursor to high temperature resistant chars. The common uses for high temperature resistant chars include aircraft brake discs, equipment for sintering reactions, and heat shields or heat shielding material. The polymers that include repeating units having amine salts can be used in applications for partially or fully water soluble polymers such as viscosity control agents.

Generally, cationic initiators can polymerize benzoxazine monomers or oligomers. Suitable cationic initiators include $H_2SO_4$, $HClO_4$, $BF_3$, $AlCl_3$, t-BuCl/$Et_2AlCl$, $Cl_2/BCl_3$, $AlBr_3$, $AlBr_3$, $TiCl_4$, $I_2$, $SnCl_4$, $WCl_6$, $AlEt_2Cl$, $PF_5$, $VCl_4$, $AlEtCl_2$, and $BF_3Et_2O$. In some embodiments, the polymerization initiator is PCl5, $PCl_3$, $POCl_3$, $TiCl_5$, $SbCl_5$, $(C_6H_5)_3C+(SbCl_6)$—, or metallophorphyrin compounds such as aluminum phthalocyanine chloride, which are all known to result in similar polymers from cationically initiated polymerization of unsaturated monomers. Suitable cationic initiators further include ethyl tosylate, methyl triflate, and triflic acid. Typically, each initiator initiates a polymer with from 3 to 3,000 repeat units, so the amount of initiator needed on a mole percent basis relative to the monomer is small. However, additional initiator can be needed to compensate for loss due to adventitious moisture and other reactants that deactivate cations. In some embodiments, 0.001 to 50 mole percent initiator based upon the monomer, specifically 0.01 to 10 mole percent initiator, is used for these cationically initiated polymerizations.

The auxiliary co-monomer can be a vinylbenzyl ether resin. Suitable vinylbenzyl ether resins include those having the structure

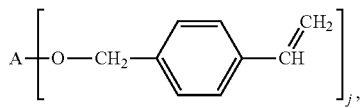

wherein A is an organic or inorganic radical of valence j, and j is from 1 to 100, specifically 1, 2, 3, 4, 5, 6, 7, or 8, more specifically 2, 3, or 4.

Vinylbenzyl ether resins can be most readily prepared from condensation of a phenol with a vinyl benzyl halide, such as vinylbenzyl chloride to produce a vinylbenzyl ether. Bisphenol-A and trisphenols and polyphenols are generally used to produce poly(vinylbenzyl ethers) that can be used to produce crosslinked thermosetting resins.

Suitable vinyl benzyl ethers include those produced from reaction of vinylbenzyl chloride or vinylbenzyl bromide with resorcinol, catechol, hydroquinone, 2,6-dihydroxy naphthalene, 2,7-dihydroxynapthalene, 2-(diphenylphosphoryl)hydroquinone, bis(2,6-dimethylphenol)2,2'-biphenol, 4,4-biphenol, 2,2',6,6'-tetramethylbiphenol, 2,2',3,3',6,6'-hexamethylbiphenol, 3,3',5,5'-tetrabromo-2,2'6,6'-tetramethylbiphenol, 3,3'-dibromo-2,2',6,6'-tetramethylbiphenol, 2,2',6,6'-tetramethyl-3,3'5-dibromobiphenol, 4,4'-isopropylidenediphenol (bisphenol A), 4,4'-isopropylidenebis(2,6-dibromophenol) (tetrabromobisphenol A), 4,4'-isopropylidenebis(2,6-dimethylphenol) (teramethylbisphenol A), 4,4'-isopropylidenebis(2-methylphenol), 4,4'-isopropylidenebis(2-allylphenol), 4,4'(1,3-phenylenediisopropylidene)bisphenol (bisphenol M), 4,4'-isopropylidenebis(3-phenylphenol), 4,4'-(1,4-phenylenediisoproylidene)bisphenol (bisphenol P), 4,4'-ethylidenediphenol (bisphenol E), 4,4'oxydiphenol, 4,4'thiodiphenol, 4,4'thiobis(2,6-dimethylphenol), 4,4'-sulfonyldiphenol, 4,4'-sulfonylbis(2,6-dimethylphenol) 4,4'-sulfinyldiphenol, 4,4'-hexafluoroisoproylidene)bisphenol (Bisphenol AF), 4,4'-(1-phenylethylidene)bisphenol (Bisphenol AP), bis(4-hydroxyphenyl)-2,2-dichloroethylene (Bisphenol C), bis(4-hydroxyphenyl)methane (Bisphenol-F), bis(2,6-dimethyl-4-hydroxyphenyl)methane, 4,4'-(cyclopentylidene)diphenol, 4,4'-(cyclohexylidene)diphenol (Bisphenol Z), 4,4'-(cyclododecylidene)diphenol 4,4'-(bicyclo [2.2.1]heptylidene)diphenol, 4,4'-(9H-fluorene-9,9-diyl)diphenol, 3,3-bis(4-hydroxyphenyl)isobenzofuran-1(3H)-one, 1-(4-hydroxyphenyl)-3,3-dimethyl-2,3-dihydro-1H-inden-5-ol, 1-(4-hydroxy-3,5-dimethylphenyl)-1,3,3,4,6-pentamethyl-2,3-dihydro-1H-inden-5-ol, 3,3,3',3'-tetramethyl-2,2', 3,3'-tetrahydro-1,1'-spirobi[indene]-5,6'-diol (Spirobiindane), dihydroxybenzophenone (bisphenol K), tris(4-hydroxyphenyl)methane, tris(4-hydroxyphenyl)ethane, tris(4-hydroxyphenyl)propane, tris(4-hydroxyphenyl)butane, tris (3-methyl-4-hydroxyphenyl)methane, tris(3,5-dimethyl-4-hydroxyphenyl)methane, tetrakis(4-hydroxyphenyl)ethane, tetrakis(3,5-dimethyl-4-hydroxyphenyl)ethane, bis(4-hydroxyphenyl)phenylphosphine oxide, dicyclopentadienylbis (2,6-dimethyl phenol), dicyclopentadienyl bis(ortho-cresol), and dicyclopentadienyl bisphenol.

The auxiliary co-monomer can be an alkene containing monomer or an alkyne-containing monomer such as acrylate containing compound, styrenic resin or alkenyl aromatic monomer, allylic monomer etc. Suitable alkene- and alkyne-containing monomers include those described in U.S. Pat. No. 6,627,704.

One class of alkene-containing monomers is the acrylate-containing compounds having the structure

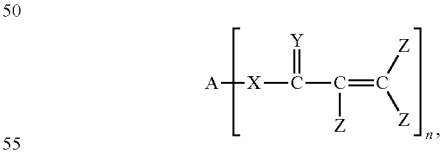

wherein A is an organic or inorganic radical of valence n; X is nitrogen or oxygen; Y is oxygen or sulfur; and each occurrence of Z is independently chosen from hydrogen, halogen, and C1-C24 hydrocarbyl.

Suitable alkene-containing monomers include acrylate and methacrylate-functionalized materials capable of undergoing free radical polymerization. They can be monomers and/or oligomers such as (meth)acrylates, (meth)acrylamides, N-vinylpyrrolidone and vinylazlactones as disclosed in U.S. Pat. No. 4,304,705. Such monomers include mono-, di-, and polyacrylates and methacrylates, such as methyl acrylate, methyl methacrylate, ethyl acrylate, isopropyl methacrylate, isooctyl acrylate, isobornyl acrylate, isobornyl methacrylate, acrylic acid, n-hexyl acrylate, tetrahydrofurfuryl acrylate, N-vinylcaprolactam, N-vinylpyrrolidone, acrylonitrile, stearyl acrylate, allyl acrylate, glycerol diacrylate, glycerol triacrylate, ethylene glycol diacrylate, diethylene glycol diacrylate, triethylene glycol dimethacrylate, 1,6-hexanediol diacrylate, 1,3-propanediol diacrylate, 1,3-propanediol dimethacrylate, trimethylolpropane triacrylate, 1,2,4-butanetriol trimethacrylate, 2-phenoxyethyl acrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-methoxyphenyldimethylmethane, 2,2-bis[1-(3-acryloxy-2-hydroxy)] propoxyphenylpropane, tris(hydroxyethyl)isocyanurate trimethacrylate; the bis-acrylates and bis-methacrylates of polyethylene glycols of number average molecular weight 200-500 atomic mass units, and bis-acrylates and bis-methacrylates of polybutadienes of number average molecular weight 1000-10,000 atomic mass units, copolymerizable combinations of acrylated monomers such as those disclosed in U.S. Pat. No. 4,652,274; and acrylated oligomers such as those disclosed in U.S. Pat. No. 4,642,126.

It can be desirable to crosslink the alkene- or alkyne-containing monomer. Particularly useful as crosslinker compounds are acrylates such as allyl acrylate, glycerol diacrylate, glycerol triacrylate, ethylene glycol diacrylate, diethylene glycol diacrylate, triethylene glycol dimethacrylate, 1,6-hexanediol diacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldi-methylmethane, 2,2-bis[1-(3-acryloxy-2-hydroxy)]propoxyphenylpropane, tris(hydroxyethyl)isocyanurate trimethacrylate; and the bis-acrylates and bis-methacrylates of polyethylene glycols of average molecular weight 200-500 atomic mass units.

In some examples, the use of a tri- to penta-functional (meth)acrylate compound in an amount of 3 to 20 mass % with respect to the total amount of functionalized PPE resin composition is preferred. As the tri- to penta-functional methacrylate compound, trimethylolpropane trimethacrylate (TMPT) or the like can be used, while trimethylolpropane triacrylate or the like can be used as the tri- to penta-functional acrylate compound. Addition of these crosslinking curing agents further increases the heat resistance of the laminated sheets finally obtained. While (meth)acrylate compounds having functional groups fewer or more than 3 to 5 can be used, the use of tri- to pentafunctional (meth)acrylate compounds increases the heat resistance of the resulting laminated sheet to the larger extent. Even when a tri- to penta-functional (meth)acrylate compound is used, the use of this compound in an amount of less than 3 mass % with respect to the total amount of the functionalized PPE resin composition may not provide the final laminated sheets with sufficient heat resistance, while the use in an amount of more than 20 mass % can reduce the dielectric characteristics and humidity resistance of the final laminated sheets.

Also included among alkene- or alkyne-containing monomers are styrenic resins or alkenyl aromatic monomers. The alkenyl aromatic monomer can have the structure:

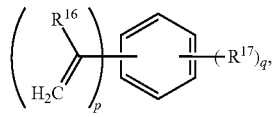

wherein each $R^{16}$ is independently hydrogen, C1-C12 alkyl, C2-C12 alkenyl, C2-C12 alkynyl, C6-C18 aryl; each $R^{17}$ is independently halogen, C1-C12 alkyl, C1-C12 alkoxy, C6-C18 aryl; p is 1 to 4; and q is 0 to 5. When p=1, the alkenyl aromatic monomer is termed a monofunctional alkenyl aromatic monomer; when p=2-4, the alkenyl aromatic monomer is termed a polyfunctional alkenyl aromatic monomer.

Suitable alkenyl aromatic monomers include styrene, alpha-methylstyrene, alpha-ethylstyrene, alpha-isopropylstyrene, alpha-tertiary-butylstyrene, alpha-phenylstyrene, and the like; halogenated styrenes such as chlorostyrene, dichlorostyrene, trichlorostyrene, bromostyrene, dibromostyrene, tribromostyrene, fluorostyrene, difluorostyrene, trifluorostyrene, tetrafluorostyrene, pentafluorostyrene, and the like; halogenated alkylstyrenes such as chloromethylstyrene, and the like; alkoxystyrenes such as methoxystyrene, ethoxystyrene, and the like; polyfunctional alkenyl aromatic monomers such as 1,3-divinylbenzene, 1,4-divinylbenzene, trivinylbenzene, 1,3-diisopropenylbenzene, 1,4-diisopropenylbenzene, and the like; and combinations comprising at least one of the foregoing alkenyl aromatic monomers. In the foregoing substituted styrenes for which no substituent position is specified, the substituents can occupy any free position on the aromatic ring.

Preferred alkenyl aromatic monomers include styrene, alpha-methylstyrene, 2-methylstyrene, 3-methylstyrene, 4-methylstyrene, 2-t-butylstyrene, 3-t-butylstyrene, 4-t-butylstyrene, 1,3-divinylbenzene, 1,4-divinylbenzene, 1,3-diisopropenylbenzene, 1,4-diisopropenylbenzene, and the like, and combinations comprising at least one of the foregoing alkenyl aromatic monomers. Preferred alkenyl aromatic monomers further include styrenes having from 1 to 5 halogen substituents on the aromatic ring, and combinations comprising at least one such halogenated styrene.

The composition can comprise the alkenyl aromatic monomer in an amount of at least 30 parts, preferably at least 40 parts, more preferably at least 50 parts, per 100 parts total of the capped poly(arylene ether), the alkenyl aromatic monomer, and the acryloyl monomer. The composition can comprise the alkenyl aromatic monomer in an amount of up to 98 parts, preferably up to 80 parts, more preferably up to 70 parts, per 100 parts total of the capped poly (arylene ether), the alkenyl aromatic monomer, and the acryloyl monomer.

The alkene or alkyne containing monomers could be allylic monomers. The olefinically unsaturated monomer can comprise an allylic monomer. An allylic monomer is an organic compound comprising at least one, preferably at least two, more preferably at least three allyl (—$CH_2$—CH=$CH_2$) groups. Suitable allylic monomers include, for example, diallyl phthalate, diallyl isophthalate, triallyl mellitate, triallyl mesate, triallyl benzenes, trialkenyl cyanurate, trialkenyl isocyanurate, a combination thereof, and partial polymerization products prepared therefrom.

In particular, trialkenyl isocyanurates or trialkenyl cyanurates that are excellent in compatibility are favorable. Representative examples of trialkenyl isocyanurates or trialkenyl cyanurates are triallylisocyanurate, trimethallylisocyanurate, trimethallylcyanurate, triallylcyanurate, triallylisocyanurate (TAIC), and triallylcyanurate (TAC), or a combination thereof are preferred.

It is because these two crosslinking curing agents give laminated sheets having a lower dielectric constant and excellent in heat resistance and reliability. Further, as the TAIC or TAC, either its monomer (hereinafter referred to as m-TAIC or m-TAC) or prepolymer (hereinafter referred to as p-TAIC or p-TAC) can be used or both can be used in combination.

The auxiliary co-monomer can be an arylcyclobutene resin. Suitable arylcyclobutenes include those derived from compounds of the general structure:

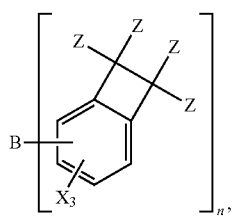

wherein B is an organic or inorganic radical of valence n (including carbonyl, sulfonyl, sulfinyl, sulfide, oxy, alkylphosphonyl, arylphosphonyl, isoalkylidene, cycloalkylidene, arylalkylidene, diarylmethylidene, methylidene dialkylsilanyl, arylalkylsilanyl, diarylsilanyl, and C6-C20 phenolic compounds); each occurrence of X is independently hydroxy or C1-C24 hydrocarbyl (including linear and branched alkyl and cycloalkyl); each occurrence of Z is independently hydrogen, halogen, or C1-C12 hydrocarbyl; and n is 1 to 1000, specifically 1 to 8, more specifically 2 or 3 or 4. Other useful arylcyclobutenes and methods of arylcyclobutene synthesis can be found in U.S. Pat. Nos. 4,743,399, 4,540,763, 4,642,329, 4,661,193, 4,724,260, and 5,391,650.

The auxiliary co-monomer can be a perfluorovinyl ether resin. Useful perfluorovinyl ethers include those having the structure:

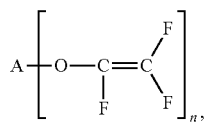

wherein A is a divalent organic or inorganic radical of valence n; and n is 1 to 1000, specifically 1 to 8, more specifically 2 or 3 or 4.

Perfluorovinyl ethers are typically synthesized from phenols and bromotetrafluoroethane followed by zinc catalyzed reductive elimination producing ZnFBr and the desired perfluorovinylether. By this route bis, tris, and other polyphenols can produce bis-, tris and poly(perfluorovinylether)s.

Phenols useful in their synthesis include resorcinol, catechol, hydroquinone, 2,6-dihydroxy naphthalene, 2,7-dihydroxynapthalene, 2-(diphenylphosphoryl)hydroquinone, bis (2,6-dimethylphenol) 2,2'-biphenol, 4,4-biphenol, 2,2',6,6'-tetramethylbiphenol, 2,2',3,3',6,6'-hexamethylbiphenol, 3,3',5,5'-tetrabromo-2,2'6,6'-tetramethylbiphenol, 3,3'-dibromo-2,2',6,6'-tetramethylbiphenol, 2,2',6,6'-tetramethyl-3,3'5'-dibromobiphenol, 4,4'-isopropylidenediphenol (bisphenol A), 4,4'-isopropylidenebis(2,6-dibromophenol) (tetrabromobisphenol A), 4,4'-isopropylidenebis(2,6-dimethylphenol) (teramethylbisphenol A), 4,4'-isopropylidenebis(2-methylphenol), 4,4'-isopropylidenebis(2-allylphenol), 4,4'-(1,3-phenylenediisopropylidene)bisphenol (bisphenol M), 4,4'-isopropylidenebis(3-phenylphenol) 4,4'-(1,4-phenylenediisoproylidene)bisphenol (bisphenol P), 4,4'-ethylidenediphenol (bisphenol E), 4,4'-oxydiphenol, 4,4'-thiodiphenol, 4,4'-thiobis(2,6-dimethylphenol), 4,4'-sulfonyldiphenol, 4,4'-sulfonylbis(2,6-dimethylphenol) 4,4'-sulfinyldiphenol, 4,4'-hexafluoroisoproylidenebisphenol (Bisphenol AF), 4,4'(1-phenylethylidene)bisphenol (Bisphenol AP), bis(4-hydroxyphenyl)-2,2-dichloroethylene (Bisphenol C), bis(4-hydroxyphenyl)methane (Bisphenol-F), bis (2,6-dimethyl-4-hydroxyphenyl)methane, 4,4'-(cyclopentylidene)diphenol, 4,4'-(cyclohexylidene)diphenol (Bisphenol Z), 4,4'-(cyclododecylidene)diphenol 4,4'-(bicyclo[2.2.1]heptylidene)diphenol, 4,4'-(9H-fluorene-9,9-diyl)diphenol, 3,3-bis(4-hydroxyphenyl)isobenzofuran-1(3H)-one, 1-(4-hydroxyphenyl)-3,3-dimethyl-2,3-dihydro-1H-inden-5-ol, 1-(4-hydroxy-3,5-dimethylphenyl)-1,3,3,4,6-pentamethyl-2,3-dihydro-1H-inden-5-ol, 3,3,3',3'-tetramethyl-2,2', 3,3'-tetrahydro-1,1'spirobi[indene]-5,6'-diol (spirobiindane), dihydroxybenzophenone (bisphenol K), tris(4-hydroxyphenyl)methane, tris(4-hydroxyphenyl)ethane, tris(4-hydroxyphenyl)propane, tris(4-hydroxyphenyl)butane, tris(3-methyl-4-hydroxyphenyl)methane, tris(3,5-dimethyl-4-hydroxyphenyl)methane, tetrakis(4-hydroxyphenyl)ethane, tetrakis(3,5-dimethyl-4-hydroxyphenyl)ethane, bis(4-hydroxyphenyl)phenylphosphine oxide, dicyclopentadienylbis (2,6-dimethyl phenol), dicyclopentadienyl bis(2-methylphenol), and dicyclopentadienyl bisphenol.

The auxiliary co-monomer can be an oligomer or polymer with curable vinyl or curable unsaturated functionality. Such materials include oligomers and polymers having crosslinkable unsaturated bonding, such as curable or unsaturated rubbers, unsaturated polyesters or vinyl ester resins, polyester/epoxy copolymer resins, unsaturated esterimide resins, and curable silicone resins.

Curable rubbers include styrene butadiene rubber (SBR), butadiene rubber (BR), and nitrile butadiene rubber (NBR) having unsaturated bonding based on butadiene; natural rubber (NR), isoprene rubber (IR), chloroprene rubber (CR), butyl rubber (IIR), and halogenated butyl rubber having unsaturated bonding based on isoprene; ethylene-α-olefin copolymer elastomers having unsaturated bonding based on dicyclopentadiene (DCPD), ethylidene norbornene (ENB), or 1,4-dihexadiene (1,4-HD) (namely, ethylene-α-olefin copolymers obtained by copolymerizing ethylene, an α-olefin, and a diene, such as ethylene-propylene-diene terpolymer (EPDM) and ethylene-butenediene terpolymer (EBDM)).

In some examples, an ethylene-butene-diene terpolymer (EBDM) is used. Examples also include hydrogenated nitrile rubber, fluorocarbon rubbers such as vinylidenefluoride-hexafluoropropene copolymer and vinylidenefluoride-pentafluoropropene copolymer, epichlorohydrin homopolymer (CO), copolymer rubber (ECO) prepared from epichlorohydrin and ethylene oxide, epichlorohydrin allyl glycidyl copolymer, propylene oxide allyl glycidyl ether copolymer, propylene oxide epichlorohydrin allyl glycidyl ether terpolymer, acrylic rubber (ACM), urethane rubber (U), silicone rubber (Q), chlorosulfonated polyethylene rubber (CSM), polysulfide rubber (T) and ethylene acrylic rubber.

Further examples of curable rubbers include various liquid rubbers, for example various types of liquid butadiene rubbers, and the liquid atactic butadiene rubber that is butadiene polymer with 1,2-vinyl connection prepared by anionic living polymerization. It is also possible to use liquid styrene butadiene rubber, liquid nitrile butadiene rubber (CTBN, VTBN, ATBN, by Ube Industries, Ltd.), liquid chloroprene rubber, liquid polyisoprene, dicyclopentadiene type hydrocarbon polymer, and polynorbornene (as sold by Elf Atochem).

Additional examples of curable rubber include polybutadiene resins. Generally, polybutadienes containing high levels of 1,2 addition, are desirable for thermosetting matrices. Also included are the functionalized polybutadienes and poly(butadiene-styrene) random copolymers sold by Ricon Resins, Inc. under the trade names RICON, RICACRYL, and RICOBOND resins. These include polybutadienes containing both low vinyl content such as RICON 130, 131, 134, 142, and polybutadienes containing high vinyl content such as RICON 150, 152, 153, 154, 156, 157, and P30D; also random copolymers of styrene and butadiene including RICON 100, 181, 184, and maleic anhydride grafted polybutadienes and the alcohol condensates derived therefrom such as RICON 130MA8, RICON MA13, RICON 130MA20, RICON 131MAS, RICON 131MA10, RICON MA17, RICON MA20, RICON 184MA6 and RICON 156MA17; also included are polybutadienes which can be used to improve adhesion including RICOBOND 1031, RICOBOND 1731, RICOBOND 2031, RICACRYL 3500, RICOBOND 1756, and RICACRYL 3500; also are included the polybutadienes RICON 104 (25% polybutadiene in heptane), RICON 257 (35% polybutadiene in styrene), and RICON 257 (35% polybutadiene in styrene); also are included are (meth)acrylic functionalized polybutadienes such as polybutadiene diacrylates and polybutadiene dimethacrylates. These materials are sold under the trade names RICACRYL 3100, RICACRYL 3500, and RICACRYL 3801. Also are included are powder dispersions of functional polybutadiene derivatives including, for example, RICON 150D, 152D, 153D, 154D, P30D, RICOBOND 1731 HS, and RICOBOND 1756 HS. Further butadiene resins include poly(butadiene-isoprene) block and random copolymers, such as those with number average molecular weights of 3,000 to 50,000 atomic mass units and polybutadiene homopolymers having number average molecular weights of 3,000 to 50,000 atomic mass units. Also included are polybutadiene, polyisoprene, and polybutadiene-isoprene copolymers functionalized with maleic anhydride, 2-hydroxyethylmaleic acid, or hydroxylated functionality.

Unsaturated polyesters or vinyl ester resins are generally obtained by reaction of at least one polyhydric alcohol with at least one polybasic acid comprising an unsaturated polybasic acid. These include unsaturated polyester resins or vinyl ester resin based on maleic anhydride, maleic acid, fumaric acid, itaconic acid and citraconic acid, chloromaleic acid, dimeric methacrylic acid, nadic acid, tetrahydrophthalic acid, endo-methylenetetrahydrophthalic acid, hexachloro-endo-methylenetetrahydrophthalic acid, halogenated phthalic acids, as well as unsaturated epoxy acrylate resin based on acryloyl group, methacryloyl group and allyl group, urethane acrylate resin, polyether acrylate resin, polyalcohol acrylate resin, alkyd acrylate resin, polyester acrylate resin, spiroacetal acrylate resin, diallyl phthalate resin, diallyl tetrabromophthalate resin, diethyleneglycol bisallylcarbonate resin, and polyethylene polythiol resin.

Often, polyfunctional saturated and aromatic acids are employed in conjunction with the polybasic unsaturated acids to reduce the density of the ethylenic unsaturation and provide the desired chemical and mechanical properties. Examples of saturated and aromatic polybasic acids include succinic acid, adipic acid, sebacic acid, azelaic acid, dodecanedioic acid, eicoic acid, phthalic acid, isophthalic acid, terephthalic acid, as well as their esters and anhydrides. Preferred aromatic polybasic acids include phthalic acid, isophthalic acid, and their esters and anhydrides.

Examples of polyhydric alcohols include ethylene glycol, propylene glycol, diethylene glycol, dipropylene glycol, 1,2-butanediol, 1,3-butanediol, 1,4-butanediol, neopentyl glycol, glycerol, triethylene glycol, pentanediol, hexylene glycol, hydrogenated bisphenol A, bisphenol A-alkylene oxide adducts, tetrabromobisphenol A-alkylene oxide adducts, and the like. Preferred polyhydric alcohols include propylene glycol. Unsaturated polyesters are commercially available, often as compositions further comprising an alkenyl aromatic monomer, and include, for example, the unsaturated polyester resins obtained from Ashland as Ashland Q6585, and from Alpha Owens Corning as AOC-XV2346.

Polyester/epoxy copolymer resins comprise both ester and epoxy functionality. Representative polyester/epoxy copolymer resins include those described in U.S. Pat. No. 6,127,490. In this reference, the polyester/epoxy copolymer resin is prepared by first reacting maleic acid with dicyclopentadiene to produce a ten-carbon double ring ester, promoting esterification by the addition of a hydroxyl-containing compound such as an alcohol or glycol, and then reacting the resulting intermediate with a polyfunctional epoxy compound such as bisphenol A diglycidyl ether. Other suitable polyester/epoxy copolymer resins are described in U.S. Pat. No. 4,703,338. Combinations of polyester/epoxy resins with alkenyl aromatic compounds such as styrene or vinyl toluene can also be used.

The curable compound can comprise an unsaturated esterimide resin. In general the preparation of polyesterimides involves polycondensation between an aromatic carboxylic anhydride containing at least one additional carboxylic group and at least one $\alpha,\beta$-ethylenically unsaturated dicarboxylic acid with a diamine and a diol and/or ethanolamine. The resultant compound contains a five-membered cyclic imide ring and $\alpha,\beta$-ethylenically unsaturated dicarboxylic acid ester. The preparation of polyesterimides is described, for example, in U.S. Pat. No. 4,273,917, and "Synthesis and Characterization of Novel Polyesterimides" J.-Y. Shieh, P.-H. Hsu, C.-S. Wang, J. Applied Polym. Sci., Vol. 94, pages 730-738 (2004). Thermosetting unsaturated polyesterimides are commercially available in vinyl toluene or styrene, such as von-Roll Isola's Damisol 3309 and Altana Chemie's Dobeckan 2025.

The curable compound can comprise a curable silicone resin. Curable silicone resins are polysiloxanes comprising polymerizable functionality. For example, a curable silicone can comprise a polydialkylsiloxane with terminal silyl hydride functionality and a polydialkylsiloxane with terminal vinyl silane functionality that enables polymerization via a catalyzed hydrosilylation reaction. Such compositions are described in U.S. Pat. Nos. 4,029,629 and 4,041,010, 4,061, 609, and 4,329,273.

Many applications dictate that materials meet various standards for flame retardancy. To achieve the required properties, flame retardants can be included in the curable composition.

Suitable flame retardants include bromine-containing flame retardants, chlorine-containing flame retardants, phosphorus-containing flame retardants, nitrogen-containing flame retardants, oxides of antimony, aluminum hydroxide, magnesium hydroxide, or a combination thereof.

Representative examples of bromine-containing fire retardants include organic compounds containing bromine, such as tetrabromobisphenol-A, tribromophenol, poly(2,6-dibromo-1,4-phenylene ether), a brominated polystyrene, 1,3,5-tris(2,4,6-tribromophenoxy)triazine, brominated cyclododecane, brominated bisphenol-A diglycidyl ether and bromodiphenyl ether. Among the bromine-containing fire retardants described above, the bromodiphenyl ether is most preferred and represented by the following formula:

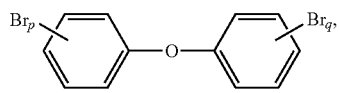

wherein each of p and q independently represents an integer of from 1 to 5 with the proviso that (p+q) equal to 4 (or more than 4) to 10 (or less than 10). Suitable examples of bromodiphenyl ethers can include tetrabromodiphenyl ether, hexabromodiphenyl ether, octabromodiphenyl ether and decabromodiphenyl ether. These bromodiphenyl ethers can be used individually or in combination.

If brominated flame retardants are used, it is preferred that the bromine content of the brominated flame retardant be greater than 45%, advantageously greater than 60%, and preferably greater than 70%. The high bromine content of the flame retardant allows one to obtain UL-94 flammability and at the same time maintaining high PPE content and optimal dielectric properties.

Further, a fire retardant having at least two ethylenically unsaturated double bonds can also be used. The use of such a fire retardant having crosslinking properties is advantageous from the viewpoint of the chemical resistance of a final cured PPE resin composition. Preferred examples of fire retardants having crosslinking properties include tetrabromobisphenol-A diallyl ether, tetrabromobisphenol-A diacrylate, tetrabromobisphenol-A dimethacrylate, tetrabromobisphenol-A di-2-acryloxyethyl ether, and tetrabromobisphenol-A di(2-methacryloxyethyl) ether.

Typical examples of the brominated flame retardant also include, but not limited thereto, ethylene bis-tetrabromophthalimide, ethylene bis-pentabromobenzene, 2,4,6-tribromophenol acrylate, tribromophenol ethoxyacrylate, bisphenol A diethoxylate dimethacrylate, tribromostyrene, pentabromobenzyl monoacrylate, N-tribromophenyl maleimide, hexabromobenzene and brominated polystyrene. Aromatic organic brominated compounds are preferable and examples are decabromodiphenylethane ($C_8H_4Br_{10}$); 4,4-dibromobiphenyl ($C_6H_4Br_2$); and ethylene bistetrabromophthalimide. A representative example of the bromine-containing flame retardant is N1,N1-diallyl-2[-2,6-dibromo-4-(2-{3,5-dibromo-4-[(diallylcarbamoyl)methoxy]phenyl}-1,1-dimethylethyl)phenoxy]acetamide.

Chlorine-containing fire retardants include organic compounds containing chlorine, such as chlorinated polyethylene and chlorinated paraffin.

Suitable flame retardants include phosphorus salts having the formula:

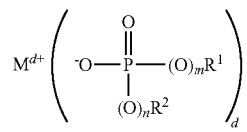

wherein $M^{d+}$ is a metal ion or an onium ion; d is 1, 2, 3, or 4 according to the identity of M and its oxidation state; each occurrence of $R^1$ and $R^2$ is independently C1-C18 hydrocarbyl; and each occurrence of m and n is independently 0 or 1. As described herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. The hydrocarbyl residue, when so stated however, can contain heteroatoms over and above the carbon and hydrogen members of the substituent residue. Thus, when specifically noted as containing such heteroatoms, the hydrocarbyl or hydrocarbylene residue can also contain carbonyl groups, amino groups, hydroxyl groups, or the like, or it can contain heteroatoms within the backbone of the hydrocarbyl residue. In some cases, Md+ is an onium ion. Suitable onium ions include, for example, ammonium cation (NH4+), mono-(C1-C12)-hydrocarbylammonium cations, di-(C1-C12)-hydrocarbylammonium cations, tri-(C1-C12)-hydrocarbylammonium cations, tetra-(C1-C12)-hydrocarbylammonium cations, phosphonium cation (PH4+), mono-(C1-C12)-hydrocarbylphosphonium cations, di-(C1-C12)-hydrocarbylphosphonium cations, tri-(C1-C12)-hydrocarbylphosphonium cations, tetra-(C1-C12)-hydrocarbylphosphonium cations, sulfonium cation (SH3+), mono-(C1-C12)-hydrocarbylsulfonium cations, di-(C1-C12)-hydrocarbyl sulfonium cations, tri-(C1-C12)-hydrocarbyl sulfonium cations, and the like, and a combination thereof. In some other cases, Md+ is a metal ion. Suitable metal ions include, for example, ions of magnesium, calcium, aluminum, antimony, tin, germanium, titanium, zinc, iron, zirconium, cerium, bismuth, strontium, manganese, lithium, sodium, potassium, and the like, and a combination thereof.

Exemplary organophosphate ester flame retardants include, but are not limited to, phosphate esters comprising phenyl groups, substituted phenyl groups, or a combination of phenyl groups and substituted phenyl groups, bis-aryl phosphate esters based upon resorcinol such as, for example, resorcinol bis-diphenylphosphate, as well as those based upon bis-phenols such as, for example, bis-phenol A bis-diphenylphosphate.

In certain embodiments, the flame retardant materials composition comprises a metal dialkyl phosphinate. As used herein, the term "metal dialkyl phosphinate" refers to a salt comprising at least one metal cation and at least one dialkyl phosphinate anion. The metal dialkyl phosphinate can have formula:

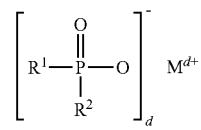

wherein $R^1$ and $R^2$ are each independently C1-C6 alkyl; M is calcium, magnesium, aluminum, or zinc; and d is 2 or 3. Examples of R1 and R2 include methyl, ethyl, n-propyl, isopropyl, n-butyl, tert-butyl, n-pentyl, and phenyl. In some other cases, $R^1$ and $R^2$ are ethyl, M is aluminum, and d is 3 (that is, the metal dialkyl phosphinate is aluminum tris(diethyl phosphinate)).

In certain embodiments, the organophosphate ester includes a bis-aryl phosphate of formula:

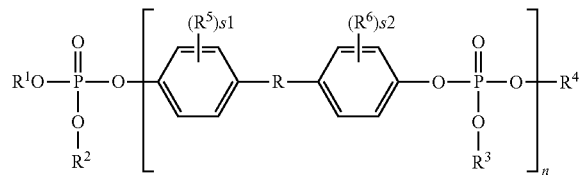

wherein R, $R^5$ and $R^6$ are independently at each occurrence an alkyl group having 1 to 5 carbons and $R^1$-$R^4$ are independently an alkyl, aryl, arylalkyl or alkylaryl group having 1 to 10 carbons; n is an integer equal to 1 to 25; and s1 and s2 are independently an integer equal to 0 to 2. In some embodiments $OR^1$, $OR^2$, $OR^3$ and $OR^4$ are independently derived from phenol, a monoalkylphenol, a dialkylphenol or a trialkylphenol. It is well known that the bis-aryl phosphate is derived from a bisphenol. Exemplary bisphenols include 2,2-bis(4-hydroxyphenyl)propane (so-called bisphenol A), 2,2-bis(4-hydroxy-3-methylphenyl)propane, bis(4-hydroxyphenyl)methane, bis(4-hydroxy-3,5-dimethylphenyl)methane and 1,1-bis(4-hydroxyphenyl)ethane. In one example, the bisphenol comprises bisphenol A.

In certain embodiments, the composition comprises a nitrogen-containing flame retardant comprising a nitrogen-containing heterocyclic base and a phosphate or pyrophosphate or polyphosphate acid. In some example, the nitrogen-containing flame retardant has the formula:

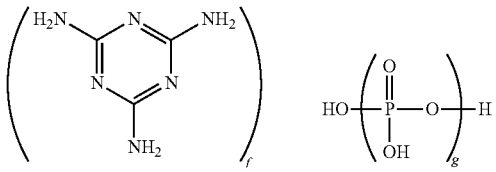

wherein g is 1 to 10,000 and the ratio of f to g is 0.5:1 to 1.7:1, specifically 0.7:1 to 1.3:1, more specifically 0.9:1 to 1.1:1. This formula includes species in which one or more protons are transferred from the polyphosphate group to the melamine group(s). When g is 1, the nitrogen-containing flame retardant is melamine phosphate (CAS Reg. No. 20208-95-1). When g is 2, the nitrogen-containing flame retardant is melamine pyrophosphate (CAS Reg. No. 15541 60-3). When g is, on average, greater than 2, the nitrogen-containing flame retardant is melamine polyphosphate (CAS Reg. No. 56386-64-2). In some other examples, the nitrogen containing flame retardant is melamine pyrophosphate, melamine polyphosphate, or a combination thereof. When the nitrogen-containing flame retardant is melamine polyphosphate, g has an average value of greater than 2 to 10,000, specifically 5 to 1,000, more specifically 10 to 500. When the nitrogen containing flame retardant is melamine polyphosphate, g has an average value of greater than 2 to 500.

Methods for preparing melamine phosphate, melamine pyrophosphate, and melamine polyphosphate are known in the art, and all are commercially available. For example, melamine polyphosphates can be prepared by reacting polyphosphoric acid and melamine, as described, for example, in U.S. Pat. No. 6,025,419 to Kasowski et al., or by heating melamine pyrophosphate under nitrogen at 290° C. to constant weight, as described in International Patent Application No. WO98/08898 A1 to Jacobson et al.

The composition can include a phosphine compound selected from trihydrocarbylphosphines, trihydrocarbylphosphine oxides, and a combination thereof. The phosphine compound can be a trihydrocarbylphosphine. The trihydrocarbylphosphine can have formula $PR^3R^4R^5$ wherein $R^3$-$R^5$ at each occurrence are independently C1-C12 hydrocarbyl, with the proviso that the trihydrocarbylphosphine has at least six carbon atoms. In the context of the trihydrocarbylphosphine and the trihydrocarbylphosphine oxide discussed below, the hydrocarbyl substituent can include, in addition to carbon and hydrogen, a hydroxy substituent (e.g., the hydrocarbyl substituent can be 4-hydroxyphenyl), or an ether oxygen (e.g., the hydrocarbyl substituent can be 4-phenoxyphenyl). Suitable trihydrocarbylphosphines include, for example, triphenylphosphine, allyldiphenylphosphine, diallylphenylphosphine, triallylphosphine, bis(1-naphthyl)(4-hydroxyphenyl)phosphine, bis(4-hydroxyphenyl)(1-naphthyl)phosphine, tris(4-hydroxyphenyl)phosphine, tris(1-naphthyl)phosphine, tris(2-naphthyl)phosphine, bis(4-phenoxyphenyl)(4-hydroxyphenyl)phosphine, bis(4-hydroxyphenyl)(4-phenoxyphenyl)phosphine, tris(4-phenoxyphenyl)phosphine, bis(2,4,5-trimethylphenyl)(4-hydroxyphenyl)phosphine, bis(4-hydroxyphenyl)(2,4,5-trimethylphenyl)phosphine, tris(2,4,5-trimethylphenyl)phosphine, bis(tert-butyl)(4-hydroxyphenyl)phosphine, bis(4-hydroxy-phenyl)(tert-butyl)phosphine, tris(tert-butyl)phosphine, and the like, and a combination thereof.

The phosphine compound can be a trihydrocarbylphosphine oxide. The trihydrocarbylphosphine oxide can have can have formula $O=PR^3R^4R^5$ wherein $R^3$-$R^5$ are each independently C1-C12 hydrocarbyl, with the proviso that the trihydrocarbylphosphine oxide has at least six carbon atoms. Suitable trihydrocarbylphosphine oxides include, for example, triphenylphosphine oxide, allyldiphenylphosphine oxide, diallylphenylphosphine oxide, triallylphosphine oxide, bis(1-naphthyl)(4-hydroxyphenyl)phosphine oxide, bis(4-hydroxyphenyl)(1-naphthyl)phosphine oxide, tris(4-hydroxyphenyl)phosphine oxide, tris(1-naphthyl)phosphine oxide, tris(2-naphthyl)phosphine oxide, bis(4-phenoxyphenyl)(4-hydroxyphenyl)phosphine oxide, bis(4-hydroxyphenyl)(4-phenoxyphenyl)phosphine oxide, tris(4-phenoxyphenyl)phosphine oxide, bis(2,4,5-trimethylphenyl)(4-hydroxyphenyl)phosphine oxide, bis(4-hydroxyphenyl)(2,4,5-trimethylphenyl)phosphine oxide, tris(2,4,5-trimethylphenyl)phosphine oxide, bis(tert-butyl)(4-hydroxyphenyl)phosphine oxide, bis(4-hydroxy-phenyl)(tert-butyl)phosphine oxide, tris(tert-butyl)phosphine oxide, and the like, and a combination thereof.

The composition can comprise 5 to 95 parts by weight (pbw) of the phosphorus salt, based on 100 pbw total of the phosphorus salt and the phosphine compound. Within this range, the phosphorus salt amount can be at least 10 pbw, or at least 20 pbw. Also within this range, the phosphorus salt amount can be up to 90 wt %, or up to 80 wt %.

In certain embodiments, the composition can comprise metal hydroxides. Suitable metal hydroxides include all those capable of providing fire retardance, as well as a combination thereof. The metal hydroxide can be chosen to have substantially no decomposition during processing of the fire additive composition and/or flame retardant thermoplastic composition. Substantially no decomposition is defined herein as amounts of decomposition that do not prevent the flame retardant additive composition from providing the desired level of fire retardance. Exemplary metal hydroxides include, but are not limited to, magnesium hydroxide (for example, CAS No. 1309-42-8), aluminum hydroxide (for example, CAS No. 21645-51-2), cobalt hydroxide (for example, CAS No. 21041-93-0) and combinations of two or more of the foregoing. In some cases, the metal hydroxide has an average particle size less than or equal to 10 micrometers and/or a purity greater than or equal to 90 wt %. In some example it is desirable for the metal hydroxide to contain substantially no water, i.e. a weight loss of less than 1 wt % upon drying at 120° C. for 1 hour. In some example the metal hydroxide can be coated, for example, with stearic acid or other fatty acid.

Exemplary flame retardant materials include aluminum tris(diethylphosphinate) by itself or in conjunction with a phosphine oxide selected from triphenylphosphine oxide, allyldiphenylphosphine oxide, and a combination thereof. Suitable trihydrocarbylphosphine oxides include, for example, triphenylphosphine oxide, allyldiphenylphosphine oxide, diallylphenylphosphine oxide, triallylphosphine oxide, bis(1-naphthyl)(4-hydroxyphenyl)phosphine oxide, bis(4-hydroxyphenyl)(1-naphthyl)phosphine oxide, tris(4-hydroxyphenyl)phosphine oxide, tris(1-naphthyl)phosphine oxide, tris(2-naphthyl)phosphine oxide, bis(4-phenoxyphenyl)(4-hydroxyphenyl)phosphine oxide, bis(4-hydroxyphenyl)(4-phenoxyphenyl)phosphine oxide, tris(4-phenoxyphenyl)phosphine oxide, bis(2,4,5-trimethylphenyl)(4-hydroxyphenyl)phosphine oxide, bis(4-hydroxyphenyl)(2,4,5-trimethylphenyl)phosphine oxide, tris(2,4,5-trimethylphenyl)phosphine oxide, bis(tert-butyl)(4-hydroxyphenyl)phosphine oxide, bis(4-hydroxy-phenyl)(tert-butyl)phosphine oxide, tris(tert-butyl)phosphine oxide, 9,10-dihydro-9-oxa-10-phosphaphenanthrene-10-oxide, 9,10-dihydro-9-oxa-10-(2,5-dioxotetrahydro-3-furanylmethyl)-10-phosphaphenanthrene-10-oxide and the like, and a combination thereof.

Suitable green FR components are various types, which include Al(OH)3, Mg(OH)2, phosphorus & nitrogen containing compounds and also phosphorus based phenanthrene-10-oxide. Specific examples are a phosphorus compound, which does not contain a halogen atom in the molecule i.e. 9,10-dihydro-9-oxa-10-phosphaphenanthrene-10-oxide, 9,10-dihydro-9-oxa-10-(2,5-dioxotetrahydro-3-furanylmethyl)-10-phosphaphenanthrene-10-oxide etc. It could also be Boron nitride (for epoxy with rubber), phosphorus containing polyester polyol, condensed type phosphoric ester compound, guanidine sulfamate, guanidine phosphate and guanylurea phosphate, phosphazene based compounds, and tris(2-hydroxyphenyl)-phosphine oxide. Commercial phosphoric ester and phosphazene compound can be also used as added type of phosphorus compounds. Phosphoric ester can be an aromatic condensed phosphoric-acid ester, triphenyl phosphate, Cresyl, and di-2,6-xylenyl phosphate can be used. Among phosphoric ester, as aromatic condensed-phosphoric-acid ester, a 1,3-phenylene-bis(dixylenyl phosphate), a 1,3-phenylene-bis(diphenyl phosphate), etc can be used. As a phosphazene compound, phenoxy phosphazene oligomer, phenoxy tolyloxy phosphazene oligomer, methoxy phenoxy phosphazene oligomer, etc can be used. In the above-mentioned phosphorus compounds, phenoxy phosphazene oligomer and methoxy phenoxy phosphazene oligomer are preferred with respect to the solubility and hydrolysis resistance over a solvent.

In certain embodiments, the composition comprises a flame retardant selected from the group consists of an organophosphate ester, a metal dialkyl phosphinate, a nitrogen-containing flame retardant, metal hydroxides and a combination thereof. There is no particular restriction on the types of flame retardants that can be used except that the flame retardant is suitably stable at the temperatures employed during electronic materials applications processes. Exemplary flame retardants include melamine (CAS No. 108-78-1), melamine cyanurate (CAS No. 37640-57-6), melamine phosphate (CAS No. 20208-95-1), melamine pyrophosphate (CAS No. 15541-60-3), melamine polyphosphate (CAS #218768-84-4), melam, melem, melon, zinc borate (CAS No. 1332-07-6), boron phosphate, red phosphorus (CAS No. 7723-14-0), organophosphate esters, monoammonium phosphate (CAS No. 7722-76-1), diammonium phosphate (CAS No. 7783-28-0), alkyl phosphonates (CAS No. 78-38-6 and 78-40-0), metal dialkyl phosphinate, ammonium polyphosphates (CAS No. 68333-79-9), low melting glasses and combinations of two or more of the foregoing flame retardants. In some examples, the organophosphate ester is selected from tris(alkylphenyl) phosphate (for example, CAS No. 89492-23-9 or CAS No. 78-33-1), resorcinol bis-diphenylphosphate (for example, CAS No. 57583-54-7), bis-phenol A bisdiphenylphosphate (for example, CAS No. 181028-79-5), triphenyl phosphate (for example, CAS No. 115-86-6), tris(isopropylphenyl) phosphate (for example, CAS No. 68937-41-7) and combinations of two or more of the foregoing organophosphate esters.

Some other flame retardants include decabromodiphenylethane, decabromodiphenylether (AFR1021, manufactured and sold by Asahi Glass Co., Ltd., Japan); brominated epoxy compounds, non-reactive organic brominated compound e.g: Saytex8010, SR-245 & pentabromo-diphenyl ether, triphenylphosphine, Sb2O3 (PATOX-M, manufactured and sold by NIHON SEIKO CO., LTD., Japan) as auxiliary FR. As phosphorus compounds, "KD-302S" by Chemiprokasei Kaisha Ltd, that is phenoxy tolyloxy phosphazene, and the product "PX-200" made from Daihachi Chemicals Industry Ltd., which is aromatic phosphoric ester. Moreover as Mg(OH)2 (magnesium hydroxide), the product having mean particle diameter of 0.9 micrometer was used. "CL303", which is aluminum hydroxide, (mean particle diameter of 3 micrometers) made by Sumitomo Chemical Co., Ltd.

The curable composition can include an inorganic filler. Suitable inorganic fillers include, for example, alumina, silica (including fused silica and crystalline silica), boron nitride (including spherical boron nitride), aluminum nitride, silicon nitride, magnesia, magnesium silicate, glass fibers, glass mat, and a combination thereof. Suitable glass fibers include those based on E, A, C, ECR, R, S, D, and NE glasses, as well as quartz. The glass fiber can have a diameter of 2 to 30 micrometers, specifically 5 to 25 micrometers, more specifically 5 to 15 micrometers. The length of the glass fibers before compounding can be 2 to 7 millimeters, specifically 1.5 to 5 millimeters. Alternatively, longer glass fibers or continuous glass fibers can be used. The glass fiber can, optionally, include an adhesion promoter to improve its compatibility with the poly(arylene ether), the auxiliary co-monomer, or both. Adhesion promoters include chromium complexes, silanes, titanates, zircon-aluminates, propylene maleic anhydride copolymers, reactive cellulose esters and the like. Suitable glass fiber is commercially available from suppliers including, for example, Owens Corning, Nippon Electric Glass, PPG, and Johns Manville.

Suitable fillers include fused silica powder, fumed silica, spherical silica, thiourea, Al2O3, talc, kaolin, clay (aluminum silicate), antimony trioxide, glass fibers (chopped, milled and cloth), glass bubbles, hollow glass microsphere, aramid fibers, and quartz. It is preferable that the inorganic filler is at least one selected from SiO2, Al2O3, MgO, SiO2, BN, AlN and Si3N4. With this configuration, a suitable thermal expansion coefficient and a thermal conductivity required for the semiconductor package can be obtained. When Al2O3, BN and AlN are employed, a module with high thermal conductivity can be obtained. When MgO is employed, a favorable thermal conductivity can be obtained and a thermal expansion coefficient can be increased. When SiO2 (especially, amorphous SiO2) is employed, a lightweight module having a small thermal expansion coefficient and a small dielectric constant can be obtained. Inorganic powder Titanium dioxide system ceramics, barium titanate series ceramics, Lead titanate system ceramics, strontium titanate system ceramics, titanic acid calcium series ceramics, It is characterized by being titanic acid bismuth system ceramics, titanic acid magnesium system ceramics, and at least one sort of ceramics selected from groups which consist of lead zirconate system ceramics.

Exemplary fillers include an inorganic insulating filler (trade name: baked talc, average particle diameter 0.4 µm, supplied by Nippon Talc K.K.); Al2O3 90 wt % (produced by Showa Denko K.K., 'AS-40', spherical form 12 µm); Aluminum hydroxide (Sumitomo Chemical inorganic filler), Glassiness balloon (Toshiba Ballotini "HSC-110"), Magnesium hydroxide (made by Kyowa Chemical Industry); Silica powder object used the trade name by an ADOMA textile company "ADOMA fine SO-25R" (mean particle diameter of 0.6 micrometer); Silica powder object used the trade name by an ADOMA textile company "ADOMA fine SO-25R" (mean particle diameter of 0.6 micrometer); Titanium dioxide used lot number TR-840 by Fuji Titanium Industry Co., Ltd.; a titanium dioxide with a mean particle diameter of 0.3 micrometer [Fuji Titanium Industry Co., Ltd. make and trade name TR-840].

When an inorganic filler is utilized, the curable composition can comprise 2 to 900 pbw of inorganic filler, based on 100 pbw total of the disclosed high heat, high purity compound, the curing promoter, and the auxiliary co-monomer. In some embodiments, the curable composition comprises 100 to 900 pbw inorganic filler, specifically 200 to 800 pbw inorganic filler, and more specifically 300 to 700 pbw inorganic filler, based on 100 pbw total high heat, high purity compound, curing promoter, and auxiliary co-monomer. In some embodiments, the curable composition comprises less than 50 pbw inorganic filler, or less than 30 pbw inorganic filler, or less than 10 pbw inorganic filler, based of 100 pbw total of the disclosed compound, the curing promoter, and the auxiliary co-monomer. In some embodiments, the curable composition can be substantially free of inorganic filler (that is, the composition can comprises less than 0.1 wt % of added inorganic filler, based 100 pbw of the disclosed compound, the curing promoter, and the auxiliary co-monomer).

The curable composition can include inorganic filler and fiber treating agents. Exemplary treating agents include: γ-glycidoxypropyltrimethoxysilane [a powder obtained by treating 360.50 parts (78.08% by weight) of a fused silica powder with 2.13 parts (0.46% by weight) of γ-glycidoxypropyltrimethoxysilane], and γ-aminopropyltrimethoxysilane. A coupling agent can be 0.3 wt % (produced by AJINOMOTO CO., INC, agent '46B'). As a silane coupling agent used for a surface treatment, gamma-aminopropyl trimethoxysilane, gamma-aminopropyl triethoxysilane, gamma-(2-aminoethyl) aminopropyl trimethoxysilane, etc. are mentioned, for example. These can be used independently or can be used together.

There is no limitation in particular the amount of the silane coupling agent used at the time of carrying out a surface treatment, and it is 0.5 to 5.0 weight section still more preferably 0.3 to 10 weight section preferably to raw material talc 100 weight section. When there is too much amount of the silane coupling agent used, there is a possibility that the heat resistance after the lamination application of pressure of an epoxy resin composition can fall. On the other hand, when there is too little amount of the silane coupling agent used, there is a possibility that a resin streak can arise at the time of the lamination application of pressure of an epoxy resin composition.

The curable composition can include rubbers. Exemplary rubbers include carboxyl-terminated butadiene acrylonitrile liquid polymers (CTBN), phenol-terminated butadiene acrylonitrile liquid polymers (PTBN), secondary amine-terminated butadiene acrylonitrile liquid polymers (ATBN), hydroxyl-terminated butadiene acrylonitrile liquid polymers (HTBN), carboxyl-terminated butadiene liquid polymers (CTB), and also following KRATON type polymers i.e., block copolymers, SBS rubbers (styrene-butadiene-styrene block copolymers), SEP rubbers (styrene-ethylene/propylene block copolymers), SEBS rubbers (styrene ethylene/butylene-styrene block copolymers), and liquid polyolefin hydrocarbons. Butadiene acrylonitrile copolymerization rubber ("N220" by Japan Synthetic Rubber Co., Ltd.: 41% of the weight of the amounts of combined acrylonitrile); polyvinyl-acetal resin ("6000AS" by DENKI KAGAKU KOGYO K.K.: 91% of the amount of acetalization); Elastomer SBS [Asahi Chemical Co., Ltd. make and trade name tough PUREN A] or NBR [Ube Industries, Ltd. make and trade name CTBN; Styrene butadiene copolymer (SBS) [Asahi Chemical Industry Co., Ltd. make and trade name ASAPUREN] can also be used.

The curable composition can include solvents. Suitable solvents can include, for example, a C3-C8 ketone, a C4-C8 N,N-dialkylamide, a C4-C16 dialkyl ether, a C6-C12 aromatic hydrocarbon, a C1-C3 chlorinated hydrocarbon, a C3-C6 alkyl alkanoate, a C2-C6 alkyl cyanide, or a combination thereof. The carbon number ranges refer to the total number of carbon atoms in the solvent molecule. For example, a C4-C16 dialkyl ether has 4 to 16 total carbon atoms, and the two alkyl groups can be the same or different. As another example, the 2 to 6 carbons in the "C2-C6 alkyl cyanides" include the carbon atom in the cyanide group. Specific ketone solvents include, for example, acetone, methyl ethyl ketone, methyl isobutyl ketone, and a combination thereof. Specific C4-C8 N,N-dialkylamide solvents include, for example, dimethylformamide, dimethylacetamide, N-methyl-2-pyrrolidone (Chemical Abstracts Service Registry No. 872-50-4), and the like, and a combination thereof. Specific dialkyl ether solvents include, for example, tetrahydrofuran, ethylene glycol monomethylether, dioxane, and the like, and a combination thereof. In some embodiments, the C4-C16 dialkyl ethers include cyclic ethers such as tetrahydrofuran and dioxane. In some embodiments, the C4-C16 dialkyl ethers are noncyclic. The dialkyl ether can, optionally, further include one or more ether oxygen atoms within the alkyl groups and one or more hydroxy group substituents on the alkyl groups. The aromatic hydrocarbon solvent can optionally comprise an ethylenically unsaturated solvent. Specific aromatic hydrocarbon solvents include, for example, benzene, toluene, xylenes, and the like, and a combination thereof. The aromatic hydrocarbon solvent is preferably unhalogenated. That is, it does not include any fluorine, chlorine, bromine, or iodine atoms. Specific C3-C6 alkyl alkanoates include, for example, methyl acetate, ethyl acetate, methyl propionate, ethyl propionate, and the like, and a combination thereof. Specific C2-C6 alkyl cyanides include, for example, acetonitrile, propionitrile, butyronitrile, and a combination thereof. In some examples, the solvent is acetone. In certain embodiments, the solvent is methyl ethyl ketone. In certain embodiments, the solvent is methyl isobutyl ketone. In certain embodiments, the solvent is N-methyl-2-pyrrolidone. In certain embodiments, the solvent is ethylene glycol monomethyl ether. Examples include, for example, methyl ethyl ketone (MEK), toluene, MEK and DMF.

When a solvent is utilized, the curable composition can comprise 2 to 100 pbw of the solvent, based on 100 pbw total of the disclosed high heat, high purity compound, the curing promoter, and the auxiliary co-monomer. Specifically, the solvent amount can be 5 to 80 pbw, more specifically 10 to 60 pbw, and even more specifically 20 to 40 pbw, based on 100 pbw total of the disclosed compound, the curing promoter, and the auxiliary co-monomer. The solvent can be chosen, in part, to adjust the viscosity of the curable composition. Thus, the solvent amount can depend on variables including the type and amount of the disclosed compound, the type and amount of curing promoter, the type and amount of auxiliary co-monomer, and the processing temperature used for impregnation of the reinforcing structure with the curable composition.

The curable composition can include one or more additional additives. Suitable additional additives include, for example, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and a combination thereof. Exemplary additional additives include, for example, tetrafluoroethylene resin, natural carnauba; 6,6'-(sulfonyl)bis(3,4-dihydro-3-phenyl-2H-1,3-benzoxazine); and polyhedral oligomeric silsesquioxane (POSS) based components; and the like.

The curable compositions can be subjected to various treatments to cure the composition (e.g., initiate reaction of a disclosed compound and/or auxiliary co-monomer with a curing promoter, such as an organic peroxide). There is no particular limitation on the method by which the composition can be cured. The composition can, for example, be cured thermally or by using irradiation techniques, including UV irradiation and electron beam irradiation. When heat curing is used, the temperature selected can be 80° C. to 300° C., and preferably 120° C. to 240° C. The heating period can be 1 minute to 10 hours, though such heating period can advantageously be 1 minute to 6 hours, more preferably 3 hours to 5 hours. Such curing can be staged to produce a partially cured and often tack-free resin, which then is fully cured by heating for longer periods or temperatures within the aforementioned ranges.

The disclosed compounds and compositions (e.g., curable compositions, thermosets, thermoplastics) can be used in a variety of applications and articles, including any applications where conventional high heat compositions and compounds are currently used. Exemplary uses and applications include coatings such as protective coatings, sealants, weather resistant coatings, scratch resistant coatings, and electrical insulative coatings; adhesives; binders; glues; composite materials such as those using carbon fiber and fiberglass reinforcements. When utilized as a coating, the disclosed compounds and compositions can be deposited on a surface of a variety of underlying substrates. For example, the compositions can be deposited on a surface of metals, plastics, glass, fiber sizings, ceramics, stone, wood, or any combination thereof. The disclosed compositions can be used as a coating on a surface of a metal container, such as those commonly used for packaging and containment in the paint and surface covering industries. In some instances the coated metal is aluminum or steel.

Articles that can be prepared using the disclosed curable compositions include, for example, electrical components and computer components. Articles that can be prepared using the disclosed curable compositions include, for example, automotive, aircraft, and watercraft exterior and interior components. In certain embodiments, the disclosed curable compositions are used for the production of composite materials for use in the aerospace industry.

In certain embodiments, an article comprises the cured composition obtained by curing a curable composition comprising a disclosed compound, a curing promoter, optionally, an auxiliary vinyl co-monomer, and optionally one or more additional additives. The curable composition can be used in forming composites used for printed circuit boards. Methods of forming composites for use in printed circuit boards are known in the art and are described in, for example, U.S. Pat. No. 5,622,588 to Weber, U.S. Pat. No. 5,582,872 to Prinz, and U.S. Pat. No. 7,655,278 to Braidwood.

Additional applications for the curable compositions include, for example, acid bath containers; neutralization tanks; aircraft components; bridge beams; bridge deckings; electrolytic cells; exhaust stacks; scrubbers; sporting equipment; stair cases; walkways; automobile exterior panels such as hoods and trunk lids; floor pans; air scoops; pipes and ducts, including heater ducts; industrial fans, fan housings, and blowers; industrial mixers; boat hulls and decks; marine terminal fenders; tiles and coatings; building panels; business machine housings; trays, including cable trays; concrete modifiers; dishwasher and refrigerator parts; electrical encapsulants; electrical panels; tanks, including electrorefining tanks, water softener tanks, fuel tanks, and various filament-wound tanks and tank linings; furniture; garage doors; gratings; protective body gear; luggage; outdoor motor vehicles; pressure tanks; printed circuit boards; optical waveguides; radomes; railings; railroad parts such as tank cars; hopper car covers; car doors; truck bed liners; satellite dishes; signs; solar energy panels; telephone switchgear housings; tractor parts; transformer covers; truck parts such as fenders, hoods, bodies, cabs, and beds; insulation for rotating machines including ground insulation, turn insulation, and phase separation insulation; commutators; core insulation and cords and lacing tape; drive shaft couplings; propeller blades; missile components; rocket motor cases; wing sections; sucker rods; fuselage sections; wing skins and flairings; engine narcelles; cargo doors; tennis racquets; golf club shafts; fishing rods; skis and ski poles; bicycle parts; transverse leaf springs; pumps, such as automotive smog pumps; electrical components, embedding, and tooling, such as electrical cable joints; wire windings and densely packed multi-element assemblies; sealing of electromechanical devices; battery cases; resistors; fuses and thermal cut-off devices; coatings for printed wiring boards; casting items such as capacitors, transformers, crankcase heaters; small molded electronic parts including coils, capacitors, resistors, and semiconductors; as a replacement for steel in chemical processing, pulp and paper, power generation, and wastewater treatment; scrubbing towers; pultruded parts for structural applications, including structural members, gratings, and safety rails; swimming pools, swimming pool slides, hot-tubs, and saunas; drive shafts for under the hood applications; dry toner resins for copying machines; marine tooling and composites; heat shields; submarine hulls; prototype generation; development of experimental models; laminated trim; drilling fixtures;

bonding jigs; inspection fixtures; industrial metal forming dies; aircraft stretch block and hammer forms; vacuum molding tools; flooring, including flooring for production and assembly areas, clean rooms, machine shops, control rooms, laboratories, parking garages, freezers, coolers, and outdoor loading docks; electrically conductive compositions for antistatic applications; for decorative flooring; expansion joints for bridges; injectable mortars for patch and repair of cracks in structural concrete; grouting for tile; machinery rails; metal dowels; bolts and posts; repair of oil and fuel storage tanks, and numerous other applications.

Methods of forming a composite can include impregnating a reinforcing structure with a curable composition; partially curing the curable composition to form a prepreg; and laminating a plurality of prepregs; wherein the curable composition comprises a disclosed compound, a curing promoter, optionally, an auxiliary co-monomer, and optionally, one or more additional additives.

Reinforcing structures suitable for prepreg formation are known in the art. Suitable reinforcing structures include reinforcing fabrics. Reinforcing fabrics include those having complex architectures, including two or three-dimensional braided, knitted, woven, and filament wound. The curable composition is capable of permeating such complex reinforcing structures. The reinforcing structure can comprise fibers of materials known for the reinforcement of plastics material, for example fibers of carbon, glass, metal, and aromatic polyamides. Suitable reinforcing structures are described, for example, in Anonymous (Hexcel Corporation), "Prepreg Technology", March 2005, Publication No. FGU 017b; Anonymous (Hexcel Corporation), "Advanced Fibre Reinforced Matrix Products for Direct Processes", June 2005, Publication No. ITA 272; and Bob Griffiths, "Farnborough Airshow Report 2006", CompositesWorld.com, September 2006. The weight and thickness of the reinforcing structure are chosen according to the intended use of the composite using criteria well known to those skilled in the production of fiber reinforced resin composites. The reinforced structure can contain various finishes suitable for the disclosed matrix.

The method of forming the composite comprises partially curing the curable composition after the reinforcing structure has been impregnated with it. Partial curing is curing sufficient to reduce or eliminate the wetness and tackiness of the curable composition but not so great as to fully cure the composition. The resin in a prepreg is customarily in the partially cured state, and those skilled in the thermoset arts, and particularly the reinforced composite arts, understand the concept of partial curing and how to determine conditions to partially cure a resin without undue experimentation. References herein to properties of the "cured composition" refer to a composition that is substantially fully cured. For example, the resin in a laminate formed from prepregs is typically substantially fully cured. One skilled in the thermoset arts can determine whether a sample is partially cured or substantially fully cured without undue experimentation. For example, one can analyze a sample by differential scanning calorimetry to look for an exotherm indicative of additional curing occurring during the analysis. A sample that is partially cured will exhibit an exotherm. A sample that is substantially fully cured will exhibit little or no exotherm. Partial curing can be effected by subjecting the curable-composition-impregnated reinforcing structure to a temperature of 133 to 140° C. for 4 to 10 minutes.

Commercial-scale methods of forming composites are known in the art, and the curable compositions described herein are readily adaptable to existing processes and equipment. For example, prepregs are often produced on treaters. The main components of a treater include feeder rollers, a resin impregnation tank, a treater oven, and receiver rollers. The reinforcing structure (E-glass, for example) is usually rolled into a large spool. The spool is then put on the feeder rollers that turn and slowly roll out the reinforcing structure. The reinforcing structure then moves through the resin impregnation tank, which contains the curable composition. The varnish impregnates the reinforcing structure. After emerging from the tank, the coated reinforcing structure moves upward through the vertical treater oven, which is typically at a temperature of 175 to 200° C., and the solvent of the varnish is boiled away. The resin begins to polymerize at this time. When the composite comes out of the tower it is sufficiently cured so that the web is not wet or tacky. The cure process, however, is stopped short of completion so that additional curing can occur when laminate is made. The web then rolls the prepreg onto a receiver roll.

While the above-described curing methods rely on thermal curing, it is also possible to effect curing with radiation, including ultraviolet light and electron beams. Combinations of thermal curing and radiation curing can also be used.

In certain embodiments, a composite is formed by a method comprising impregnating a reinforcing structure with a curable composition; partially curing the curable composition to form a prepreg; and laminating a plurality of prepregs; wherein the curable composition comprises a disclosed compound, a curing promoter, optionally, an auxiliary co-monomer, and optionally, one or more additional additives.

In certain embodiments, a printed circuit board comprises a composite formed by a method comprising impregnating a reinforcing structure with a curable composition; partially curing the curable composition to form a prepreg; and laminating a plurality of prepregs; wherein the curable composition comprises a disclosed compound, a curing promoter, optionally, an auxiliary co-monomer, and optionally, one or more additional additives.

Processes useful for preparing the articles and materials include those generally known to the art for the processing of thermosetting resins. Such processes have been described in the literature as in, for example, Engineered Materials Handbook, Volume 1, Composites, ASM International Metals Park, Ohio, copyright 1987 Cyril A. Dostal Senior Ed, pp. 105-168 and 497-533, and "Polyesters and Their Applications" by Bjorksten Research Laboratories, Johan Bjorksten (pres.) Henry Tovey (Ch. Lit. Ass.), Betty Harker (Ad. Ass.), James Henning (Ad. Ass.), Reinhold Publishing Corporation, New York, 1956. Processing techniques include resin transfer molding; sheet molding; bulk molding; pultrusion; injection molding, including reaction injection molding (RIM); atmospheric pressure molding (APM); casting, including centrifugal and static casting open mold casting; lamination including wet or dry lay up and spray lay up; also included are contact molding, including cylindrical contact molding; compression molding; including vacuum assisted resin transfer molding and chemically assisted resin transfer molding; matched tool molding; autoclave curing; thermal curing in air; vacuum bagging; pultrusion; Seeman's Composite Resin Infusion Manufacturing Processing (SCRIMP); open molding, continuous combination of resin and glass; and filament winding, including cylindrical filament winding. In certain embodiments, an article can be prepared from the disclosed curable compositions via a resin transfer molding process.

EXAMPLES

Samples for Scanning Electronic Microscopy (SEM) can be cut to size, microtomed to obtain a fresh, flat surface for analysis, and etched in toluene at 23° C. for 15 seconds. Then the samples can be coated with gold. The samples can be examined using a Carl Zeiss AG-EVO® 40 Series scanning electron microscope. The conditions can be SEM mode, a probe current of 40 picoamps, HV (high vacuum), and an acceleration voltage of 20 kilovolts.

Dielectric constants and dissipation factors can be measured at 23° C. according to IPC-TM-650 2.5.5.9. The samples were conditioned at 23° C. and 50% relative humidity for a minimum of 24 hours before testing. The measuring cell can be a Hewlett-Packard Impedance Material Analyzer Model 4291B and have a width of 27.5 centimeters, a height of 9.5 centimeters, and a depth of 20.5 centimeters. The electrodes can be Hewlett-Packard Model 16453A and have a diameter of 7 millimeters. Measurements can be conducted using a capacitance method, sweeping a range of frequencies when DC voltage is applied to the dielectric materials. The applied voltage can be 0.2 millivolt to 1 volt at the frequency range of 1 megahertz to 1 gigahertz. Values for dielectric constants (Dk, relative permittivity) and loss tangent (Df, dissipation factor) at frequencies of 100 megahertz, 500 megahertz, and 1000 megahertz (1 gigahertz) can be recorded.

Unnotched Izod impact strength, expressed in joules per meter (J/m), can be measured at 23° C. with a hammer energy of 2 foot-pounds in accordance with ASTM D 4812-2006, "Standard Test Method for Unnotched Cantilever Beam Impact Strength of Plastics". Reported values can reflect an average of 5 specimens per composition.

NMR Method A: Chemical structures of the synthetic products were determined by proton nuclear magnetic resonance ($^1$H-NMR) spectroscopy using an Agilent DD2 600 Megahertz $^1$H-NMR spectrometer.

DSC Method A: Melting points and Tgs were measured on a TA Instruments 2920 M-DS. The thermal scans can range from 30 to 250° C. under a nitrogen atmosphere with a heating rate of 20° C./min.

NMR Method B: The chemical structures were determined by proton nuclear magnetic resonance ($^1$H-NMR) spectroscopy using a Mercury Plus 400 Megahertz $^1$H-NMR spectrometer.

DSC Method B: Melting points and Tgs were measured on a Discovery DSC analyzer from TA Instruments with Robotic, RC unit, Data Station and Software. The thermal scans range from 40 to 300° C. under a nitrogen atmosphere at a heating rate of 20° C./min. The sample was cooled to 40° C. and a second thermal scan up to 300° C. at 20° C./min was used to detect any transitions.

DSC Method C: A sample of the monomer was placed in a DSC pan and the temperature was increased from 40 to 350° C. at 20° C./min. The sample was cooled to 40° C. and a second thermal scan up to 350° C. at 20° C./min was used to detect any transitions.

TABLE 1

Reagents Used in Synthetic Examples

| Reagent | Description | CAS Reg. No. | Supplier |
|---|---|---|---|
| PPPBP | 3,3-bis(4-hydroxyphenyl)-N-phenylphthalimidine | 6607-41-6 | |
| SBI-BP | 6,6'-dihydroxy-3,3,3',3'-tetramethyl-1,1'-spirobiindane | 32507-25-8 | |
| TMBPA | 2,2'-bis(2,3,5-dimethyl-phenyl)propane | 5613-46-7 | |
| BPI | 1,1'-Bis(4-hydroxyphenyl)-3,3,5-trimethyl-cyclohexane | 129188-99-4 | |
| TMBP | 2,2',6,6'-tetramethyl-4,4'-biphenol | 4/1/2147 | |

TABLE 1-continued

Reagents Used in Synthetic Examples

| Reagent | Description | CAS Reg. No. | Supplier |
|---|---|---|---|
| 4-VBC | 4-vinylbenzyl chloride | 1592-20-7 | Sigma-Aldrich |
| 3/4-VBC | Vinylbenzyl chloride; Combination of 3- and 4-isomers, 97%, contains 700-1100 ppm nitromethane as inhibitor, 50-100 ppm tert-butyl-catechol as inhibitor | 30030-25-2 | Sigma-Aldrich |
| Allyl Bromide | 3-Bromopropene, 99%, contains 300 ppm of propylene oxide as inhibitor | 106-95-6 | Fisher Scientific |
| PC | Propylene carbonate; anhydrous, 99.7% | 108-32-7 | Sigma-Aldrich |
| EC | Ethylene carbonate, anhydrous, 99% | 96-49-1 | Sigma-Aldrich |
| DMI | 1,3-dimethyl-2-imidazolidinone | 80-73-9 | Sigma-Aldrich |
| NaOH | Aq. Sodium Hydroxide solution, 50% | 1310-73-2 | |
| ACl | Acryloyl chloride; 97.0%, contains <210 ppm MEHQ as stabilizer | 814-68-6 | Fisher Scientific |
| MACl | Methacryloyl chloride; ≥97.0% (GC), contains ~0.02% 2,6-di-tert-butyl-4-methylphenol as stabilizer | 920-46-7 | Fisher Scientific |
| TEA | Triethylamine; >99% | 121-44-8 | Sigma-Aldrich |
| $K_2CO_3$ | Reagent grade, ≥98%, powder, –325 mesh | 584-08-7 | Sigma-Aldrich |
| NaOH | Aq. Sodium Hydroxide solution, 50% | 1310-73-2 | |
| ADOGEN 464 | Methyl trialkyl(C8-C10) ammonium chloride | 72749-59-8 | Sigma-Aldrich |
| TBS | 4-tert-butylstyrene | 1746-23-2 | Sigma-Aldrich |
| Trigonox 101 | 2,5-dimethyl-2,5-di(tert-butyl-peroxy)hexane | 78-63-7 | Fisher Scientific |
| HEGCl | Hexaethylguanidinium Chloride | 69082-76-4 | |

The procedure employed to prepare vinyl benzyl functional compounds (examples 1 and 2) is a modification of the procedure in V. Percec and J. H. Wang "ω-(Vinyl Benzyl Ether) Macromonomer of Poly(2,6-Dimethyl-1,4-Phenylene Oxide)" *Macromolecular Synthesis*, 1992, 11, 105-111.

Example 1. Synthesis of Bis(4-vinylbenzyl) SBIBP (SBIBP-4VB)

To a 4 necked 3-liter round bottom flask, equipped with mechanical stirrer, condenser, nitrogen inlet, and thermocouple probe, purged with nitrogen, was added 1.5 liters of toluene, 225 grams SBIBP (0.7305 moles), 275 grams of 4-VBC (1.8019 moles), and 4 mL ADOGEN 464. 135 grams of 50% aq. NaOH (1.6875 moles) was added and the mixture was heated to 80° C. Samples taken after 3 hours indicated that the reaction was over 98% complete. The mixture was stirred for an additional 2 hours, then cooled to room temperature. Material started to precipitate upon cooling. The mixture was concentrated using a roto-evaporator. Upon cooling, material precipitated from the concentrated toluene solution. The solid was isolated by filtration. The air dried precipitate was slurried in 2 liters of hot water (70-85° C.). The solid was isolated by filtration and dissolved in chloroform. The chloroform solution was washed with deionized water, 5% aqueous hydrochloric acid, and twice more with deionized water. The chloroform was evaporated and the solid crystallized from toluene to give 332 grams of the title compound (81.7% yield). NMR spectrum was consistent with replacing the terminal phenolic groups with vinyl benzyl. There were no detectable levels of unreacted phenolic groups. The melting point as determined by DSC (DSC Method A) was 205° C.

Example 2. Synthesis of Bis(3/4-vinylbenzyl) SBIBP (SBIBP-3/4VB)

Following the procedure in Example 1, 1.5 liters of toluene, 225 grams SBIBP (0.7305 moles), 275 grams of 3/4-VBC (1.8019 moles), 4 ml ADOGEN 464 and 135 grams of 50% aq. NaOH (1.6875 moles) yielded 345 grams of the title compound (yield 87.5%). The melting point as determined by DSC (DSC Method A) was 136° C.

Alkoxylated monomers were made in Examples 3-6. The procedure is a modification of the procedure of Jeol and coworkers for ethoxylating polyphenylene ether: S. Jeol, et al. *Journal of Polymer Science: Part A: Polymer Chemistry*, 2008, 46, 3985-3991.

Example 3. Synthesis of Ethoxylated SBIBP (SBIBP-EC)

To a 4 necked 3-liter round bottom flask, equipped with mechanical stirrer, condenser, nitrogen inlet, and thermocouple probe, purged with nitrogen was added 1000 grams of DMI, 300 grams ethylene carbonate (3.407 moles), and 400 grams of SBIBP (1.299 moles). The mixture was heated to 140° C. When the mixture became homogeneous, 425 grams (3.075 moles) of powdered anhydrous potassium carbonate was added. (NMR analysis of a sample after 6 hours showed the reaction was complete, 90% of the product was 2-hydroxyethyl functionalized SBIPB in which the phenolic groups were converted to phenoxy ethanol groups, 10% of the product had one phenolic group, one phenoxy ethanol group, and one phenoxy ethoxy ethanol group.) The reaction was cooled down with agitation. Below 100° C. the agitation was stopped and the salts allowed to settle to the bottom of the flask. After 15-20 hours the solution was decanted from the salts into ~4 L deionized water with agitation. The water was decanted. The organic layer was slurried with 1 liter of hot water (80-90° C.) for 2 hours. The organic layer was isolated and dried in air overnight and then under vacuum at 100° C. overnight. The weight of the dried title compound was 440 grams (85.6% yield). The melting point as determined by DSC (DSC Method A) was 141° C.

Example 4. Synthesis of Ethoxylated SBIBP (SBIBP-PC)

Following the procedure in Example 3, but substituting propylene carbonate for ethylene carbonate, 1000 grams of DMI, 350 grams propylene carbonate (3.428 moles), 400 grams of SBIBP (1.299 moles), and 425 grams (3.075 moles) of powdered anhydrous potassium carbonate yielded 483 grams of the title compound (yield 87.7%). The melting point as determined by DSC (DSC Method A) was 188° C. NMR analysis showed complete reaction and that two isomers were formed (91:5% 1-phenoxypropan-2-ol isomer; 8.5% 2-phenoxypropan-1-ol isomer).

Example 5. Synthesis of Ethoxylated PPPBP (PPPBP-EC) [Compound of Formula 5-a]

Following the procedure in Example 3, but substituting PPPBP for SBIBP, 750 grams of DMI, 120 grams ethylene carbonate (1.363 moles), 250 grams of PPPBP (0.636 moles), and 180 grams (1.302 moles) of powdered anhydrous potassium carbonate yielded 270 grams of the title compound (yield 88.2%). The melting point as determined by DSC (DSC Method A) was 138° C. NMR analysis showed complete reaction and a structure consistent with replacing the terminal phenolic groups with ethoxy ethanol groups.

Example 6. Synthesis of Propoxylated PPPBP (PPPBP-PC) [Compound of Formula 6-a]

Following the procedure in Example D, but substituting PPPBP for SBIBP, 750 grams of DMI, 145 grams propylene carbonate (1.420 moles), 250 grams of PPPBP (0.636 moles), and 180 grams (1.302 moles) of powdered anhydrous potassium carbonate yielded 283 grams of the title compound (yield 87.4%). The melting point as determined by DSC (DSC Method A) was 149° C. NMR analysis showed complete reaction and the formation of two isomers (91.1% 1-phenoxypropan-2-ol isomer; 8.9% 2-phenoxypropan-1-ol isomer).

Example 7. Synthesis of the Diacrylate of Ethoxylated SBIBP (SBIBP-EC-Ac)

Into a 500 mL three necked flask equipped with a magnetic stir bar, reflux condenser, and $N_2$ inlet was added 200 mL chloroform, 75 grams (0.189 moles) SBIBP-EC, and 43.5 grams (0.430 moles) TEA. The SBIBP-EC was not soluble in chloroform at ambient temperatures. The slurry was cooled below 10° C. Acryloyl chloride (44.9 grams, 0.496 moles) was added dropwise such that the reaction mixture was kept below 25° C. The temperature was increased to 50° C. for 1 hour. After cooling to ambient temperature, the reaction mixture was added to 300 mL chloroform and poured into 300 mL deionized water. Using a separatory funnel, the organic layer was washed with deionized water, 5% hydrochloric acid, and then deionized water until the pH was neutral. The chloroform was evaporated to give 88 grams of the title compound (88.8% yield), NMR analysis showed complete reaction and the structure was consistent with the desired product (replacement of alcohol with acrylate).

Example 8. Synthesis of Dimethacrylate of Ethoxylated SBIBP (SBIBP-EC-MAc)

Following the procedure in Example 7, but substituting methacryloyl chloride for acryloyl chloride, 200 mL chloroform, 75 grams (0.189 moles) SBIBP-EC, 45.4 grams (0.449 moles) TEA, and methacryloyl chloride (47 grams, 0.450 moles) gave 87 grams of the title compound (86.3% yield). NMR analysis showed complete reaction and the structure was consistent with the desired product (replacement of alcohol with methacrylate).

Example 9. Synthesis of the Diacrylate of Propoxylated SBIBP (SBIBP-PC-Ac)

Following the procedure in Example 7, but substituting SBIBP-PC for SBIBP-EC, 200 mL chloroform, 75 grams (0.177 moles) SBIBP-PC, 41.2 grams (0.407 moles) TEA, and acryloyl chloride (38 grams, 0.420 moles) gave 81 grams of the title compound (86.1% yield). NMR analysis showed complete reaction and the structure was consistent with the desired product (replacement of alcohol with acrylate).

Example 10. Synthesis of Dimethacrylate of Propoxylated SBIBP (SBIBP-PC-MAc)

Following the procedure in Example 8, but substituting SBIBP-PC for SBIBP-EC, 200 mL chloroform, 75 grams (0.1769 moles) SBIBP-PC, 41.2 grams (0.407 moles) TEA, and methacryloyl chloride (38 grams, 0.4198 moles) gave 81 grams of the title compound (86.1% yield). NMR analysis showed complete reaction and the structure was consistent with the desired product (replacement of alcohol with methacrylate).

Example 11. Synthesis of the Diacrylate of Ethoxylated PPPBP (PPPBP-EC-Ac)

Following the procedure in Example 9, but substituting PPPBP-EC for SBIBP-PC, 200 mL chloroform, 75 grams (0.1559 moles) PPPBP-EC, 37 grams (0.366 moles) TEA, and acryloyl chloride (35 grams, 0.387 moles) gave 74 grams of the title compound (80.6% yield). NMR analysis showed complete reaction and the structure was consistent with the desired product (replacement of alcohol with acrylate).

Example 12. Synthesis of Dimethacrylate of Ethoxylated PPPBP (PPPBP-EC-MAc)

Following the procedure in Example 8, but substituting PPPBP-EC for SBIBP-EC, 200 mL chloroform, 75 grams (0.1559 moles) PPPBP-EC, 36.3 grams (0.359 moles) TEA, and methacryloyl chloride (39.5 grams, 0.378 moles) gave 80 grams of material (83.2% yield). The melting point as determined by DSC (DSC Method A) was 108° C. NMR analysis showed complete reaction and the structure was consistent with the desired product (replacement of alcohol with methacrylate).

Example 13. Synthesis of the Diacrylate of Propoxylated PPPBP (PPPBP-PC-Ac) [Compound of Formula 7-a]

Following the procedure in Example 11, but substituting PPPBP-PC for PPPBP-EC, 200 mL chloroform, 75 grams (0.147 moles) PPPBP-PC, 34.3 grams (0.339 moles) TEA, and acryloyl chloride (31.6 grams, 0.349 moles) gave 77 grams of the title compound (84.6% yield). The melting point as determined by DSC (DSC Method A) was 101° C. NMR analysis showed complete reaction and the structure was consistent with the desired product (replacement of alcohol with acrylate).

Example 14. Synthesis of Dimethacrylate of Propoxylated PPPBP (PPPBP-PC-MAc) [Compound of Formula 8-a]

Following the procedure in Example 12, but substituting PPPBP-PC for PPPBP-EC, 200 mL chloroform, 75 grams (0.147 moles) PPPBP-PC, 343 grams (0.339 moles) TEA, and methacryloyl chloride (37.3 grams, 0.357 moles) gave 69 grams of the title compound (72.6% yield). The melting point as determined by DSC (DSC Method A) was 112° C. NMR analysis showed complete reaction and the structure was consistent with the desired product (replacement of alcohol with methacrylate).

Example 15. Synthesis of Bis(4-vinylbenzyl) PPPBP (PPPBP-4VB)

A 500 mL, 3 neck round bottom flask, equipped with mechanical stirrer, condenser, and a nitrogen inlet was purged with nitrogen. 25 grams of PPPBP (0.0635 moles), 0.5 mL of ADOGEN 464 and 150 mL of toluene were added to the reaction flask. The contents of the reaction mixture were heated to 75° C. When the temperature was achieved, 11.74 grams of 50% aq. NaOH (0.1467 moles) were added to the mixture. The contents were allowed to react for 15-20 mins and thereafter 24.05 g of 4-VBC (0.1576 moles) were added. The reaction was continued stirring for 18 hours. The contents of the flask were allowed to cool and the precipitate was filtered. All the toluene in the filtrate was removed by rotary evaporator to yield an oil. The oil was dissolved in Chloroform and washed with 0.1 N HCl, deionized water. Chloroform was removed by rotary evaporator and the resulted oil was added to methanol to yield a precipitate. The precipitate was filtered to obtain 15 grams of the title compound (37.75% yield). $^1$H NMR (Method B) spectrum of the product displayed replacement of phenolic proton with vinylbenzyl group. There were no detectable levels of unreacted phenolic groups. The melting point as determined by DSC (DSC Method B) was 169° C.

Example 16. Synthesis of Bis(3/4-vinylbenzyl) PPPBP (PPPBP-3/4VB)

Following the procedure in Example 15, 150 mL of toluene, 25 grams of PPPBP (0.0635 moles), 24.05 grams of 3/4-VBC (0.1576 moles), 0.5 mL ADOGEN 464 and 11.74 grams of 50% aq. NaOH (0.1467 moles) yielded 30 grams of the title compound (yield 75.51%). The melting point as determined by DSC (DSC Method B) was 133° C.

Example 17. Synthesis of Diallyl PPPBP (PPPBP-Al)

Following the procedure in Example 15, 150 mL of toluene, 25 grams of PPPBP (0.0635 moles), 19.07 grams of allyl bromide (0.1576 moles), 0.5 mL ADOGEN 464 and 11.74 grams of 50% aq. NaOH (0.1467 moles) yielded 26 grams of the title compound (yield 86.67%). The melting point as determined by DSC (DSC Method B) was 127° C.

Example 18. Synthesis of Bis(4-vinylbenzyl) TMBPA (TMBPA-4VB)

A 500 mL, 3 neck round bottom flask, equipped with mechanical stirrer, condenser, and a nitrogen inlet was purged with nitrogen. 18 grams of TMBPA (0.0635 moles), 0.5 mL of ADOGEN 464 and 150 mL of Toluene were added to the reaction flask. The contents of the reaction mixture were heated to 75° C. When the temperature was achieved, 11.74 grams of 50% aq. NaOH (0.1467 moles) were added to the mixture. The contents were allowed to react for 15-20 mins and thereafter 24.05 g of 4-VBC (0.1576 moles) were added. The reaction was continued stirring for 18 hours. The contents of the flask were allowed to cool and the precipitate was filtered. The filtrate was concentrated to a viscous solution by rotary evaporation at room temperature. The viscous solution was dissolved in chloroform and washed once with 0.1M HCl solution and three times with water. The organic phase was dried over anhydrous MgSO$_4$ and concentrated to yield a viscous solution. The product was precipitated (13.8 grams, 42.61%) by dissolving the solution in THF and precipitating in a methanol:water mixture (1:1). $^1$H NMR (Method B) spectrum of the product displayed replacement of phenolic protons with vinylbenzyl group. There were no detectable levels of unreacted phenolic groups. The melting point was determined by DSC (DSC Method B) as 127° C.

Example 19. Synthesis of Bis(3/4-vinylbenzyl) TMBPA (TMBPA-3/4VB)

Following the procedure in Example 18, 150 mL of toluene, 18 grams of TMBPA (0.0635 moles), 24.05 grams of 3/4-VBC (0.1576 moles), 0.5 mL ADOGEN 464 and 11.74 grams of 50% aq. NaOH (0.1467 moles) yielded 9 grams of the title compound (yield 86.67%). The melting point as determined by DSC (DSC Method B) was 111° C.

Example 20. Synthesis of Diallyl TMBPA (TMBPA-Al)

A 500 mL, 3 neck round bottom flask, equipped with mechanical stirrer, condenser, and a nitrogen inlet was purged with nitrogen. 18 grams of TMBPA (0.0635 moles), 0.5 mL of ADOGEN 464 and 150 mL of Toluene were added to the reaction flask. The contents of the reaction mixture were heated to 75° C. When the temperature was achieved, 11.74 grams of 50% aq. NaOH (0.1467 moles) was added to the mixture. The contents were allowed to react for 15-20 mins and thereafter 19.07 g of allyl bromide (0.1576 moles) was added. The reaction was continued for 18 hours. The contents of the flask were allowed to cool and the precipitate was filtered. The filtrate was concentrated to a viscous solution by rotary evaporation at room temperature. The viscous solution was dissolved in chloroform and washed once with 0.1M HCl solution and three times with water. The organic phase was dried over anhydrous $MgSO_4$ and concentrated to yield a viscous solution. The crude product was purified by preparative chromatography to yield 18.1 g of a clear liquid (78.3% yield). $^1H$ NMR (Method B) spectrum displayed replacement of phenolic proton with allyl group. There were no detectable levels of unreacted phenolic groups.

Example 21. Synthesis of Bis(4-vinylbenzyl) BPA (BPA-4VB)

A 500 mL, 3 neck round bottom flask, equipped with mechanical stirrer, condenser, and a nitrogen inlet was purged with nitrogen. 14.5 grams of BPA (0.0635 moles), 0.5 mL of ADOGEN 464 and 150 mL of toluene were added to the reaction flask. The contents of the reaction mixture were heated to 75° C. When the temperature was achieved, 11.74 grams of 50% aq. NaOH (0.1467 moles) were added to the mixture. The contents were allowed to react for 15-20 mins and thereafter 24.05 g of 4-VBC (0.1576 moles) were added. The reaction was continued stirring for 18 hours. The contents of the flask were allowed to cool and the precipitate was filtered. The precipitate was washed in 0.1 N HCl and with deionized water to yield 22.35 grams of the title compound (yield 76.44%). $^1H$ NMR (Method B) spectrum of the product displayed replacement of phenolic proton with vinylbenzyl group. There were no detectable levels of unreacted phenolic groups. The melting point as determined by DSC (DSC Method B) was 114° C.

Example 22. Synthesis of Bis(3/4-vinylbenzyl) BPA (BPA-3/4VB)

Following the procedure in Example 21, 150 mL of toluene, 14.5 grams of BPA (0.0635 moles), 24.05 grams of 3/4-VBC (0.1576 moles), 0.5 mL ADOGEN 464 and 11.74 grams of 50% aq. NaOH (0.1467 moles) yielded 27.20 grams of the title compound (yield 93.02%).

Example 23. Synthesis of Diallyl BPA (BPA-Al)

Following the procedure in Example 20, but substituting BPA for TMBPA, 150 mL of toluene, 14.5 grams of BPA (0.0635 moles), 19.07 grams of allyl bromide (0.1576 moles), 0.5 mL ADOGEN 464 and 11.74 grams of 50% aq. NaOH (0.1467 moles) yielded 10.2 grams of a colorless liquid. (yield 52.15%).

Example 24. Synthesis of Bis(4-vinylbenzyl) BPI (BPI-4VB)

A 500 mL, 3 neck round bottom flask, equipped with mechanical stirrer, condenser, and a nitrogen inlet was purged with nitrogen. 39.42 grams of BPI (0.127 moles), 0.4 grams of HEGCl, 200 mL of toluene and 48.10 grams of 4-VBCl (0.3152 moles) were added to the reaction flask. The contents of the reaction mixture were heated to 75° C. When the temperature was achieved, 23.48 grams of 50% aq. NaOH (0.2934 moles) was added to the mixture and the reaction was continued for 18 hours. The contents of the flask were allowed to cool and the precipitate was filtered. The filtrate was concentrated to a viscous solution by rotary evaporation at room temperature. The viscous solution was dissolved in chloroform and washed once with 0.1M HCl solution and three times with water. The organic phase was dried over anhydrous $MgSO_4$ and concentrated to yield a viscous solution. The crude product was washed with methanol to yield 27 g of a liquid (yield 39.22%). $^1H$ NMR (Method B) spectrum displayed replacement of phenolic proton with vinyl benzyl group. There was no detectable levels of unreacted phenolic groups.

Example 25. Synthesis of Bis(3/4-vinylbenzyl) BPI (BPI-3/4VB)

Following the procedure in Example 24, 39.42 grams of BPI (0.127 moles), 0.4 grams of HEGCl, 200 mL of toluene, 48.10 grams of 3/4-VBCl (0.3152 moles) and 23.48 grams of 50% aq. NaOH (0.2934 moles) yielded 24.05 g of a liquid (yield 34.94%). $^1H$ NMR (Method B) spectrum displayed replacement of phenolic proton with vinyl benzyl group. There were no detectable levels of unreacted phenolic groups.

Example 26. Synthesis of Diallyl BPI (BPI-Al)

Following the procedure in Example 20, but substituting BPI for TMBPA, 150 mL of toluene, 19.71 grams of BPI (0.0635 moles), 19.07 grams of allyl bromide (0.1576 moles), 0.5 mL ADOGEN 464 and 11.74 grams of 50% aq. NaOH (0.1467 moles) yielded 11 grams of the title compound (yield 44.42%).

Example 27. Synthesis of Bis(4-vinylbenzyl) TMBP (TMBP-4VB)

A 500 mL, 3 neck round bottom flask, equipped with mechanical stirrer, condenser, and a nitrogen inlet was purged with nitrogen. 5.13 grams of TMBPA (0.0212 moles), 0.5 mL of ADOGEN 464 and 150 mL of Toluene were added to the reaction flask. The contents of the reaction mixture were heated to 75° C. When the temperature was achieved, 3.91 grams of 50% aq. NaOH (0.0489 moles) were added to the mixture. The contents were allowed to react for 15-20 mins and thereafter 8.01 g of 4-VBC (0.0525 moles) was added. The reaction was continued stirring for 18 hours. The contents of the flask were allowed to cool and then poured into excess methanol. The product was filtered (6.96 grams, 69.2%) and washed with methanol. 1H NMR (Method B) spectrum of the product displayed replacement of phenolic proton with vinylbenzyl group. There were no detectable levels of unreacted phenolic groups. The melting point as determined by DSC (DSC Method B) was 126° C.

Example 28. Synthesis of Bis(3/4-vinylbenzyl) TMBP (TMBP-3/4VB)

Following the procedure in Example 20, but substituting TMBP for TMBPA, 70 mL toluene, 5.13 grams of TMBP (0.0212 moles), 8.01 g of 3/4VBCl (0.0525 moles) 0.5 mL of ADOGEN 464 and 3.91 g of aq NaOH (0.0489 moles) yielded 1 g of the title compound as a colorless liquid (yield 11.28%).

Example 29. Synthesis of Diallyl TMBP (TMBP-Al)

Following the procedure in Example 20, but substituting TMBP for TMBPA, 70 mL toluene, 5.13 grams of TMBP (0.0212 moles), 6.35 g of allyl bromide (0.0525 moles) 0.5 mL of ADOGEN 464 and 3.91 g of aq NaOH (0.0489 moles) yielded 1.97 g of the title compound (yield 28.86%). The melting point as determined by DSC (DSC method B) was 53° C.

Example 30. Synthesis of Dimethacrylate PPPBP (PPPBP-MAc)

A 500 mL, 3 neck round bottom flask, equipped with a magnetic stirrer, condenser, addition funnel and a nitrogen inlet was purged with nitrogen. 25 grams of PPPBP (0.0635 moles), 70 mL of chloroform and 15.26 grams of TEA (0.1507 moles) were added to the reaction flask. The contents of the reaction mixture were cooled in an ice bath. 15.83 grams of methacryloyl chloride (0.1591 moles) was added to the addition funnel and transferred to the reaction flask drop wise. After the completion of addition of methacryloyl chloride, the ice bath was removed and the reaction mixture was heated to 50° C. for one hour. At the end of the reaction, 200 mL of chloroform was added to the reaction mixture and it was poured into deionized water. The organic layer was washed multiple times with DI water and dried over anhydrous $MgSO_4$. Chloroform was removed by rotary evaporator and the resulting oil was dissolved in minimum amount of chloroform and precipitated into methanol to yield 20 grams of the title compound (yield 62.86%). NMR (Method B) spectrum displayed replacement of phenolic proton with methacrylate group. There were no detectable levels of unreacted phenolic groups.

Example 31. Synthesis of Dimethacrylate BPI (BPI-MAc)

Following the procedure in Example 31, but substituting BPI for PPPBP, 70 mL chloroform, 25 grams (0.0805 moles) BPI, 19.31 grams (0.191 moles) TEA, and 20.03 grams of methacryloyl chloride (0.192 moles) gave 28.8 grams of the title compound (80.21% yield). $^1$H-NMR analysis showed complete reaction and the structure was consistent with the desired product (replacement of alcohol with methacrylate).

Example 32. Synthesis of Bis(4-vinylbenzyl) PPPBP (PPPBP-4VB)

A 500 mL, 3 neck round bottom flask, equipped with mechanical stirrer, condenser, and a nitrogen inlet was purged with nitrogen. 25 grams of PPPBP (0.0635 moles), 0.25 g of HEGCl, 24.05 g of 4-VBC (0.1576 moles) and 150 mL of Toluene were added to the reaction flask. The contents of the reaction mixture were heated to 80° C. When the temperature was achieved, 11.74 grams of 50% aq. NaOH (0.1467 moles) was added to the mixture. The reaction was continued for 18 hours. The contents of the flask were allowed to cool and the precipitate was filtered. The filtrate was concentrated in a rotary evaporator to yield an oil. This oil was mixed with chloroform and washed with 0.1N hydrochloric acid and twice with deionized water to give 23.9 grams of material (60.15% yield). $^1$H NMR (Method B) spectrum displayed replacement of phenolic proton with vinylbenzyl group. There was no detectable levels of unreacted phenolic groups. The melting point as determined by DSC (DSC Method B) was 170° C.

Examples 33-60: Curing Studies

Unsaturated or vinyl monomers can be cured by free radical initiated or thermal polymerization. Various organic peroxides can be used as initiators for radical polymerization. In addition, styrenic and acrylic monomers can undergo self-initiated thermal polymerization. Self-initiated thermal polymerization of these monomers was followed by the DSC technique. The onset of heat release and the peak temperatures were recorded. A second DSC thermal scan was used to detect the Tg of the cure material.

A sample of the monomer was placed in a DSC pan and the temperature was increased from 30° C. to 280° C. at 20° C./min. The sample was cooled to 30° C. and a second thermal scan to 280° C. at 20° C./min was used to detect any transitions. The results for examples 33-38 appear in Table 2.

TABLE 2

| Example | Monomer | Tg, ° C. |
|---|---|---|
| 33 | SBI-BP-EC-Ac | 159 |
| 34 | SBI-BP-PC-MAc | 197 |
| 35 | SBI-BP-EC-MAc | 205 |
| 36 | PPP-BP-EC-MAc | 205 |
| 37 | PPP-BP-PC-MAc | 197 |
| 38 | PPP-BP-PC-Ac | 263 |

These monomers were cured with a co-monomer, 4-tert-butylstyrene (TBS). The TBS was heated and the monomers were added with stirring. Heating and stirring were continued until the solution was homogeneous. The solutions were placed in an oven set at 125° C. and thermally cured programing the temperature up to 220° C. using the following protocol: 1) Increased temperature to 150° C. and held for 30 minutes; 2) Increased temperature to 175° C. and held for 30 minutes; 3) Increased temperature to 200° C. and held for 30 minutes; 3) Increased temperature to 220° C. and held for 60 minutes; 4) Turned off oven and let cool overnight. The Tgs were determined by DSC (DSC Method A). The results for Examples 39-42 are summarized in Table 3.

TABLE 3

| Example | TBS | SBI-34VB | SBI-4VB | PPP-BP-EC-MAc | PPP-BP-PC-MAc | Tg, °C. |
|---|---|---|---|---|---|---|
| 39 | 50 | 50 | — | — | — | 196 |
| 40 | 75 | 25 | — | — | — | 165 |
| 41 | 75 | — | 25 | — | — | 191 |
| 42 | 75 | — | — | 25 | — | 148 |

Monomers (wt %) span the middle columns.

The monomers were cured in the presence of co-monomer 4-tert-butylstyrene (TBS). Three different cured samples were prepared from each material.
Cure 1: Self-curing
Cure 2: Curing in the presence of co-monomer 4-tert-butylstyrene (TBS)
Cure 3: Curing in the presence of co-monomer 4-tert-butylstyrene (TBS) and peroxide initiator Trigonox 101.

A known amount of sample of the monomer was added to a round bottomed flask placed under $N_2$ atmosphere. The sample was dissolved in a fixed amount of low boiling solvent such as chloroform or THF. TBS (1 molar equivalent) and/or Trigonox 101 (0.5 wt %) were added to the flask according to the curing protocol used. When the solutions turned homogeneous, they were placed in an oven at 50° C. and thermally cured by programming the temperature following the profiles in Table 4. At the end of the heating cycle, the oven was turned off and the samples were allowed to cool overnight.

TABLE 4

| Protocol | Temperature profile (° C.) | Equilibration time at each temperature |
|---|---|---|
| 1 | 80-130-180-225 | 30 min |
| 2 | 140-170-195-240 | 30 min |
| 3 | 120-160-200-240 | 30 min |
| 4 | 170-180-190-225 | 30 min |
| 5 | 120-160-195-240 | 30 min |
| 6 | 130-165-175-220 | 30 min |

The cured samples were analyzed for water absorption, dielectric constant measurements, Tg by DSC (Method B) and thermal stability by TGA (Table 5).

Water absorption Measurements: The samples were cut to at least 2 cm×2 cm size and weighed (M1). The samples were dried in a vacuum oven at 120° C. for 24 hours. The oven was turned off and allowed to cool to room temperature under vacuum. The samples were quickly weighed (M2) and immersed in DI water for 24 hours. The samples were then taken out of water and quickly wiped dry with paper towels and weighed again (M3). The water absorption was calculated using the formula: Water absorption (%)=(M3−M2)*100/M2.

TGA Method: A sample of the monomer was placed in a TGA pan and the temperature was increased from 40° C. to 800° C. at 20° C./min. These measurements were performed in the presence of $N_2$ gas.

TABLE 5

| Example | Monomer | Protocol # | Cure # | Thermal stability (5% dissociation) | Water absorption (%) |
|---|---|---|---|---|---|
| 43 | BPA-3/4VB | 1 | 1 | 380 | 0.36 |
| 44 | BPA-3/4VB | 1 | 2 | 385 | 0.25 |
| 45 | BPA-3/4VB | 1 | 3 | 385 | 0.43 |
| 46 | TMBPA-4VB | 2 | 1 | 335 | 1.25 |
| 47 | TMBPA-4VB | 2 | 2 | 339 | 0.05 |
| 48 | TMBPA-4VB | 2 | 3 | 335 | 0.34 |
| 49 | TMBPA-3/4VB | 3 | 1 | 339 | 0.39 |
| 50 | TMBPA-3/4VB | 3 | 2 | 328 | 0.08 |
| 51 | TMBPA-3/4VB | 3 | 3 | 339 | 0.1 |
| 52 | PPPBP-4VB | 4 | 1 | 394 | 2.03 |
| 53 | PPPBP-4VB | 4 | 2 | 395 | 1.50 |
| 54 | PPPBP-4VB | 4 | 3 | 392 | 1.38 |
| 55 | BPA-4VB | 5 | 1 | 397 | 0.45 |
| 56 | BPA-4VB | 5 | 2 | 386 | 0.25 |
| 57 | BPA-4VB | 5 | 3 | 384 | 0.37 |
| 58 | TMBP-4VB | 6 | 1 | 330 | 0.10 |
| 59 | TMBP-4VB | 6 | 2 | 315 | 0 |
| 60 | TMBP-4VB | 6 | 3 | 317 | 0.34 |

A set of the cured samples (examples 43-51) were analyzed to determine their dielectric constants.

Dielectric constant measurement: Dielectric constants and dissipation factors were measured at 23° C. according to IPC-TM-650-2.5.5.9. Test samples were in the shape of thin castings. The samples were conditioned at 23° C. and 50% relative humidity for a minimum of 24 hours before testing. The measuring cell was a Hewlett-Packard Impedance Material Analyzer Model 4291B. The electrodes were Hewlett-Packard Model 16453A and had a diameter of 7 millimeters. Measurements were conducted using a capacitance method sweeping a range of frequency when DC voltage was applied to the dielectric materials. The applied voltage was 0.2 millivolt to 1 volt at the frequency range of 100 megahertz to 1 gigahertz. Values for dielectric constants ($D_k$, relative permittivity) and loss tangent ($D_f$, dissipation factor) at frequencies of 100 megahertz, 500 megahertz, and 1000 megahertz (1 gigahertz) were recorded and are summarized in Table 6.

TABLE 6

| Ex. | Monomer | Protocol | Cure | Dk (100 MHz) | Dk (500 MHz) | Dk (1 GHz) | Df (100 MHz) | Df (500 MHz) | Df (1 GHz) |
|---|---|---|---|---|---|---|---|---|---|
| 43 | BPA-3/4VB | 1 | 1 | 3.075 | 3.057 | 3.052 | 0.00725 | 0.00738 | 0.00522 |
| 44 | BPA-3/4VB | 1 | 2 | 2.845 | 2.827 | 2.814 | 0.00721 | 0.0071 | 0.00462 |
| 45 | BPA-3/4VB | 1 | 3 | 2.945 | 2.924 | 2.921 | 0.00709 | 0.00716 | 0.00491 |
| 46 | TMBPA-4VB | 2 | 1 | 3.279 | 3.253 | 3.255 | 0.00971 | 0.00787 | 0.00362 |
| 47 | TMBPA-4VB | 2 | 2 | 2.819 | 2.793 | 2.791 | 0.00834 | 0.00715 | 0.00373 |
| 48 | TMBPA-4VB | 2 | 3 | 2.82 | 2.801 | 2.797 | 0.00866 | 0.00748 | 0.00406 |
| 49 | TMBPA-3/4VB | 3 | 1 | 2.812 | 2.788 | 2.78 | 0.00915 | 0.00772 | 0.00418 |

TABLE 6-continued

| Ex. | Monomer | Protocol | Cure | Dk (100 MHz) | Dk (500 MHz) | Dk (1 GHz) | Df (100 MHz) | Df (500 MHz) | Df (1 GHz) |
|---|---|---|---|---|---|---|---|---|---|
| 50 | TMBPA-3/4VB | 3 | 2 | 2.732 | 2.707 | 2.699 | 0.00789 | 0.00714 | 0.00425 |
| 51 | TMBPA-3/4VB | 3 | 3 | 2.641 | 2.622 | 2.614 | 0.00807 | 0.00718 | 0.00411 |

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention can be made without departing from the novel aspects of the invention as defined in the claims. The appended claims should be construed broadly and in a manner consistent with the spirit and the scope of the invention herein.

For reasons of completeness, various aspects of the present disclosure are set out in the following numbered clauses:

Clause 1. A compound having formula:

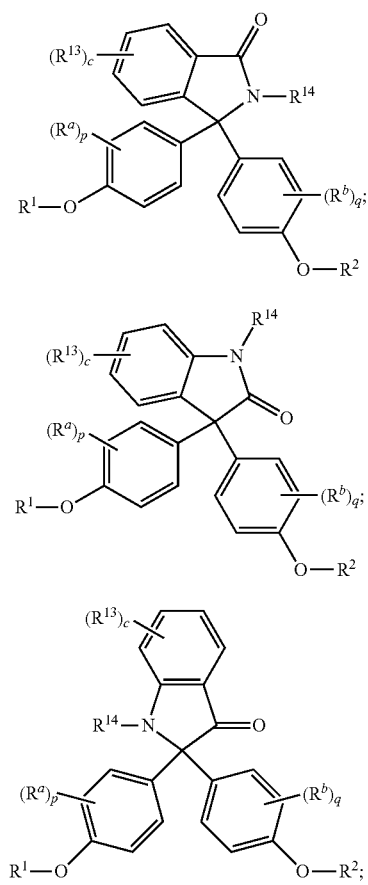

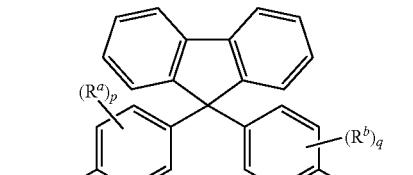

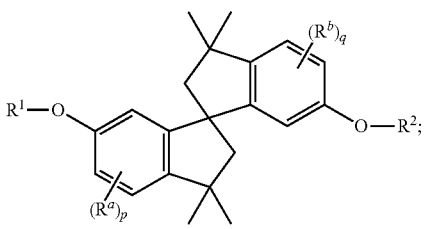

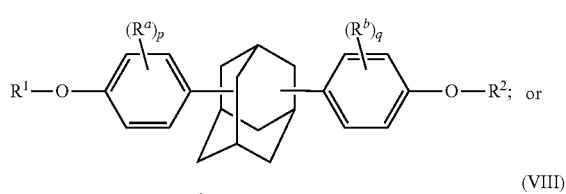

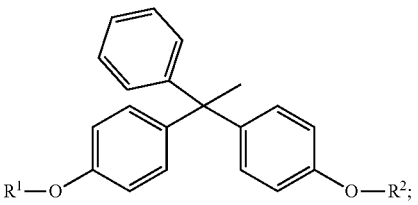

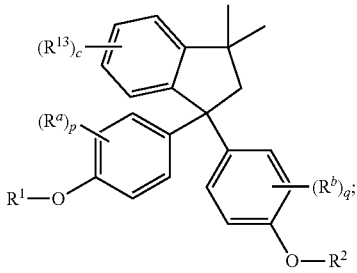

wherein $R^1$ and $R^2$ at each occurrence are each independently selected from cyano; haloalkyl; alkenyl; alkenylalkyl; alkynylalkyl; hydroxyalkyl; acrylatealkyl;

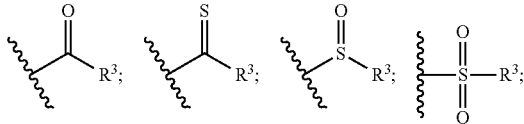

-continued

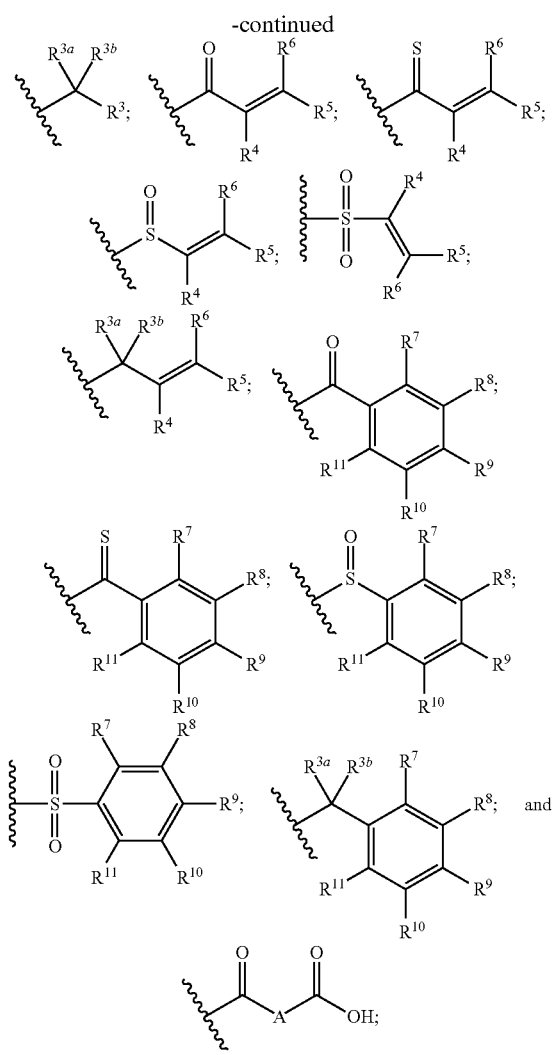

R³, at each occurrence, is independently selected from $C_1$-$C_{12}$ alkyl, heteroaryl, alkoxy, amino, and alkylamino;

R⁴-R⁶ are each independently selected from hydrogen, $C_1$-$C_{12}$ alkyl, $C_2$-$C_{12}$ alkenyl, $C_6$-$C_{18}$ aryl, $C_7$-$C_{18}$ alkyl-substituted aryl, $C_7$-$C_{18}$ aryl-substituted alkyl, $C_2$-$C_{12}$ alkoxycarbonyl, $C_7$-$C_{18}$ aryloxycarbonyl, $C_8$-$C_{18}$ alkyl-substituted aryloxycarbonyl, $C_8$-$C_{18}$ aryl-substituted alkoxycarbonyl, nitrile, formyl, carboxylate, imidate, and thiocarboxylate;

R⁷-R¹¹ are each independently selected from hydrogen, halogen, $C_1$-$C_{12}$ alkyl, $C_2$-$C_{12}$ alkenyl, hydroxy, and amino;

$R^{3a}$ and $R^{3b}$ are each independently selected from hydrogen and $C_1$-$C_{12}$ alkyl;

A at each occurrence is independently selected from a saturated or unsaturated $C_2$-$C_{12}$ divalent hydrocarbon group;

$R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4;

R¹³ at each occurrence is independently a halogen or a $C_1$-$C_6$ alkyl group; c at each occurrence is independently 0 to 4;

R¹⁴ at each occurrence is independently a $C_1$-$C_6$ alkyl, phenyl, or phenyl substituted with up to five halogens or $C_1$-$C_6$ alkyl groups;

$R^g$ at each occurrence is independently $C_1$-$C_{12}$ alkyl or halogen, or two $R^g$ groups together with the carbon atoms to which they are attached form a four-, five-, or six-membered cycloalkyl group; and t is 0 to 10.

Clause 2. The compound of clause 1, wherein R¹ and R² are each independently selected from:

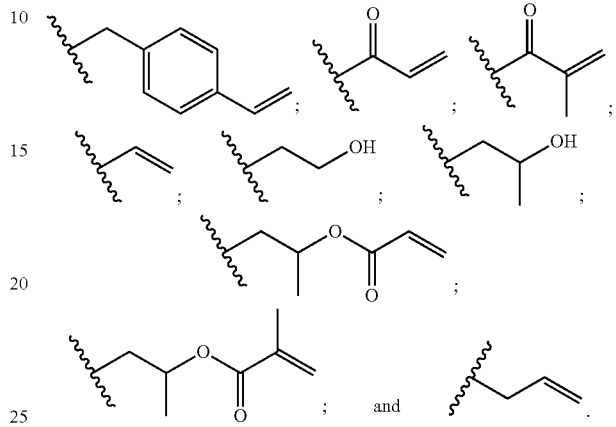

Clause 3. The compound of clause 1 or clause 2, selected from a compound having formula:

(1)

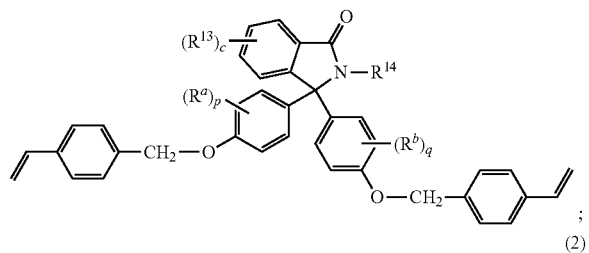

(2)

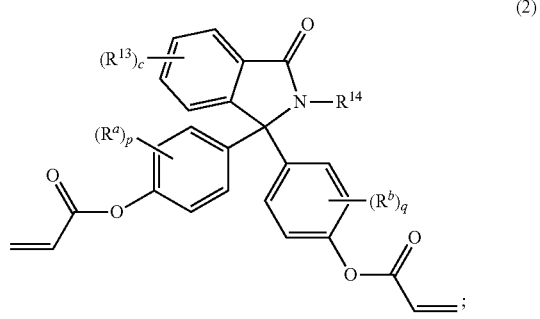

(3)

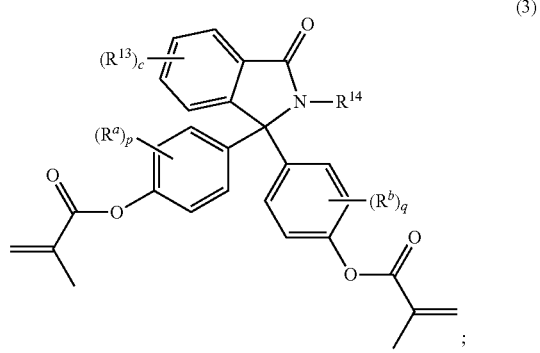

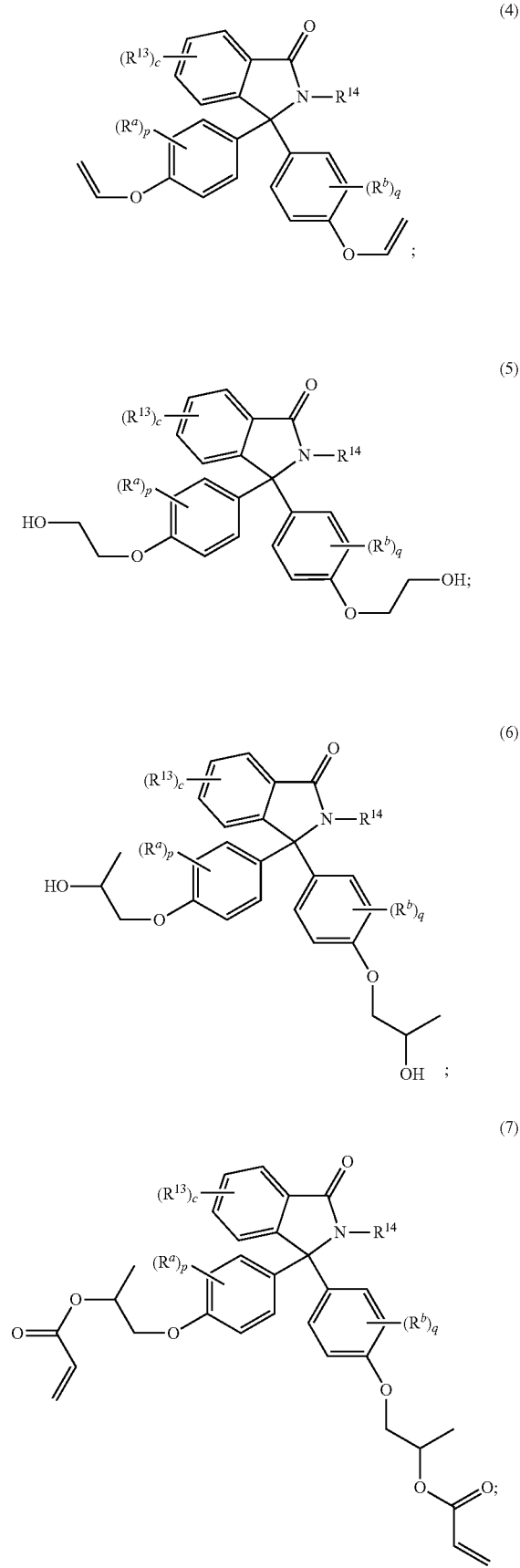

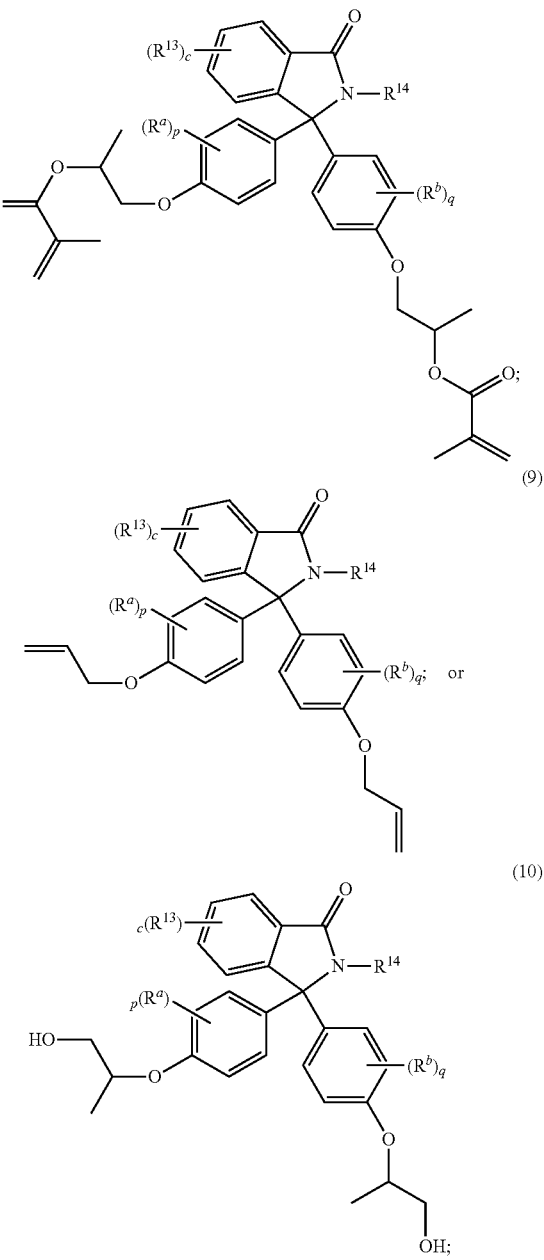

wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; and $R^{14}$ at each occurrence is independently a $C_1$-$C_6$ alkyl, phenyl, or phenyl substituted with up to five halogens or $C_1$-$C_6$ alkyl groups.

Clause 4. The compound of any one of clauses 1-3, wherein the compound has a purity of 80% or greater, as determined by high performance liquid chromatography (HPLC).

Clause 5. The compound of any one of clauses 1-4, wherein the compound has a purity of 90% or greater, as determined by high performance liquid chromatography (HPLC).

Clause 6. The compound of any one of clauses 1-5, wherein the compound has a purity of 95% or greater, as determined by high performance liquid chromatography (HPLC).

Clause 7. The compound of any one of clauses 1-6, wherein the compound has a purity of 97% or greater, as determined by high performance liquid chromatography (HPLC).

Clause 8. The compound of any one of clauses 1-7, wherein the compound has a purity of 98% or greater, as determined by high performance liquid chromatography (HPLC).

Clause 9. The compound of any one of clauses 1-8, wherein the compound has a purity of 99% or greater, as determined by high performance liquid chromatography (HPLC).

Clause 10. The compound of any one of clauses 1-9, having formula (1-a), (2-a), (3-a), (4-a), (5-a), (6-a), (7-a), (8-a), or (9-a) as described above.

Clause 11. The compound of any one of clauses 1-10, wherein the compound is derived from a compound of formula (1') as described above.

Clause 12. The compound of any one of clauses 1-11, wherein the compound is derived from a compound of formula (1'-a) as described above.

Clause 13. The compound of clause 12, wherein the compound of formula (1'-a) comprises less than 50 ppm of amino phenol impurities, less than 500 ppm of phenolphthalein, or 3 ppm or less of metal impurities.

Clause 14. A curable composition comprising (i) a compound according to any one of clauses 1-13; (ii) optionally a curing promoter; and (iii) optionally an auxiliary co-monomer.

Clause 15. The curable composition of clause 14, wherein the auxiliary co-monomer is selected from maleimide resins, benzoxazine resins, vinylbenzyl ether resins, alkene- or alkyne-containing monomers, arylcyclobutene resins, perfluorovinyl ether resins, a combination thereof.

Clause 16. The curable composition of clause 14, wherein the curing promoter is an organic peroxide.

Clause 17. The curable composition of clause 16, wherein the organic peroxide is selected from cumene hydroperoxide, 2,5-dimethylhexane-2,5-dihydroperoxide, 2,5-dimethylhexane-2,5-dihydroperoxide, α,α-bis(t-butylperoxy-m-isopropyl)benzene, dicumyl peroxide, di(trimethylsilyl) peroxide, trimethylsilyl triphenylsilyl peroxide, 2,5-dimethyl-2,5-di(t-butylperoxy)hexane (DHBP, also refers to Perhexa 25B), 2,5-dimethyl-2,5-di(t-butylperoxy)-hex-3-yne (DYBP, also refers to Perhexyne 25B, made by a Japanese firm Nippon Yushi K. K.), di-t-butylperoxide (DTBP), t-butylcumyl peroxide, dicumyl peroxide (DCP), di(t-butylperoxy isophthalate, t-butylperoxybenzoate, 2,2-bis(t-butylperoxy)butane, 2,2-bis(t-butylperoxy) octane, 2,5-dimethyl-2,5-di(benzoylperoxy)hexane, di(trimethylsilyl) peroxide, trimethylsilylphenyltriphenylsilyl peroxide, α,α'-bis(t-butylperoxy-m-isopropyl)benzene, 1,3-di(2-tert-butylperoxy isopropyl)benzene (DIPP), benzoyl peroxide (BPO), 3,3',5,5'-tetramethyl-1,4-diphenoxyquinone, chloranil, 2,4,6-tri-t-butylphenoxyl, t-butylperoxyisopropyl monocarbonate, azobisisobutyronitrile, a combination thereof.

Clause 18. A cured composition comprising the product obtained by curing the curable composition of any one of clauses 14-17.

Clause 19. The cured composition of clause 18, exhibiting a single Tg.

Clause 20. The cured composition of clause 18, exhibiting a single Tg of greater than or equal to 175° C.

Clause 21. The cured composition of clause 18, exhibiting a single Tg of greater than or equal to 200° C.

Clause 22. The cured composition of clause 18, exhibiting a single Tg of greater than or equal to 225° C.

Clause 23. The cured composition of clause 18, exhibiting a single Tg of greater than or equal to 250° C.

Clause 24. An article comprising the cured composition of any one of clauses 18-23.

Clause 25. The article of clause 24, wherein the article is selected from acid bath containers; neutralization tanks; aircraft components; bridge beams; bridge deckings; electrolytic cells; exhaust stacks; scrubbers; sporting equipment; stair cases; walkways; automobile exterior panels; floor pans; air scoops; pipes; natural gas pipes; ducts; industrial fans; fan housings; blowers; industrial mixers; boat hulls; boat decks; marine terminal fenders; tiles; building panels; business machine housings; trays; concrete modifiers; dishwasher parts; refrigerator parts; electrical encapsulants; electrical panels; tanks; electrorefining tanks; water softener tanks; fuel tanks; filament-wound tanks; filamount-wound tank linings; furniture; garage doors; gratings; protective body gear; luggage; outdoor motor vehicles; pressure tanks; printed circuit boards; optical waveguides; radomes; railings; railroad parts; hopper car covers; car doors; truck bed liners; satellite dishes; signs; solar energy panels; telephone switchgear housings; tractor parts; transformer covers; truck parts; insulation for rotating machines; commutators; core insulation and cords and lacing tape; drive shaft couplings; propeller blades; missile components; rocket motor cases; wing sections; sucker rods; fuselage sections; wing skins; wing flairings; engine narcelles; cargo doors; tennis racquets; golf club shafts; fishing rods; skis; ski poles; bicycle parts; transverse leaf springs; pumps; automotive smog pumps; electrical components; embedding; tooling; electrical cable joints; wire windings; densely packed multi-element assemblies; sealing of electromechanical devices; battery cases; resistors; fuses; thermal cut-off devices; coatings for printed wiring boards; casting items; capacitors; transformers; crankcase heaters; small molded electronic parts; coils; semiconductors; chemical processing parts; pulp and paper machine parts; power generation parts; wastewater treatment parts; scrubbing towers; pultruded parts for structural applications; structural members; gratings; safety rails; swimming pools; swimming pool slides; hot-tubs; saunas; drive shafts for under the hood applications; dry toner resins for copying machines; marine tooling; marine composites; heat shields; submarine hulls; prototype generation parts; laminated trim; drilling fixtures; bonding jigs; inspection fixtures; industrial metal forming dies; aircraft stretch block and hammer forms; vacuum molding tools; flooring; flooring for production and assembly areas; flooring for clean rooms; flooring for machine shops; flooring for control rooms; flooring for laboratories; flooring for parking garages; flooring for freezers; flooring for coolers; flooring for outdoor loading docks; electrically conductive compositions for antistatic applications; decorative flooring; expansion joints for bridges; injectable mortars for patch and repair of cracks in structural concrete; grouting for tile; machinery rails; metal dowels; bolts and posts; repair material for oil and fuel storage tanks; sport equipment; media equipment; grinding wheels; sanding wheels; mechanical rollers; conveyor belts; military equipment; space equipment; aerospace components; automotive components; mass transportation components; printed circuit boards; electrical components; optical components; optoelectrical components; computer components; watercraft exterior components; watercraft interior components; gas storage tanks; and wind turbines.

Clause 26. The article of clause 24, wherein the article is selected from aerospace components, automotive components, mass transportation components, printed circuit boards, electrical components, optical components, optoelectrical components, computer components, watercraft exterior components, and watercraft interior components.

Clause 27. The article of any one of clauses 24-26, wherein the article is produced by resin transfer molding; sheet molding; bulk molding; pultrusion; injection molding; reaction injection molding (RIM); atmospheric pressure molding (APM); casting; centrifugal casting; static casting; open mold casting; lamination; contact molding; cylindrical contact molding; compression molding; vacuum assisted resin transfer molding; chemically assisted resin transfer molding; matched tool molding; autoclave curing; thermal curing in air; vacuum bagging; Seeman's Composite Resin Infusion Manufacturing Processing (SCRIMP); open molding; filament winding; cylindrical filament winding; or a combination thereof.

Clause 28. A material comprising the cured composition of any one of clauses 18-23, wherein the material is a composite, a coating, an adhesive, an encapsulant, or a sealant.

Clause 29. The material of clause 28, wherein the material comprises one or more additional components, each independently selected from flame retardants, fillers, reinforcing fibers, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and a combination thereof.

Clause 30. The material of clause 29, wherein the filler is selected from: alumina, silica, boron nitride aluminum nitride, silicon nitride, magnesia, magnesium silicate, glass fibers, glass mat, silica powder, fumed silica, spherical silica, thiourea, $Al_2O_3$, talc, kaolin, clay, antimony trioxide, glass bubbles, hollow glass microsphere, aramid fibers, and quartz.

Clause 31. The material of any one of clauses 28-30, wherein the composite is a glass fiber based composite, a carbon fiber based composite, or a combination thereof.

Clause 32. The material of any one of clauses 28-31, wherein the material is produced by a resin transfer molding process.

The invention claimed is:
1. A compound having formula:

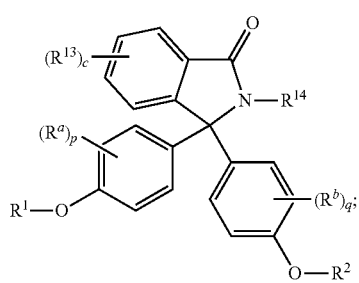

(I)

wherein $R^1$ and $R^2$ at each occurrence are each independently selected from haloalkyl; alkenyl; alkenylalkyl; alkynylalkyl; acrylatealkyl;

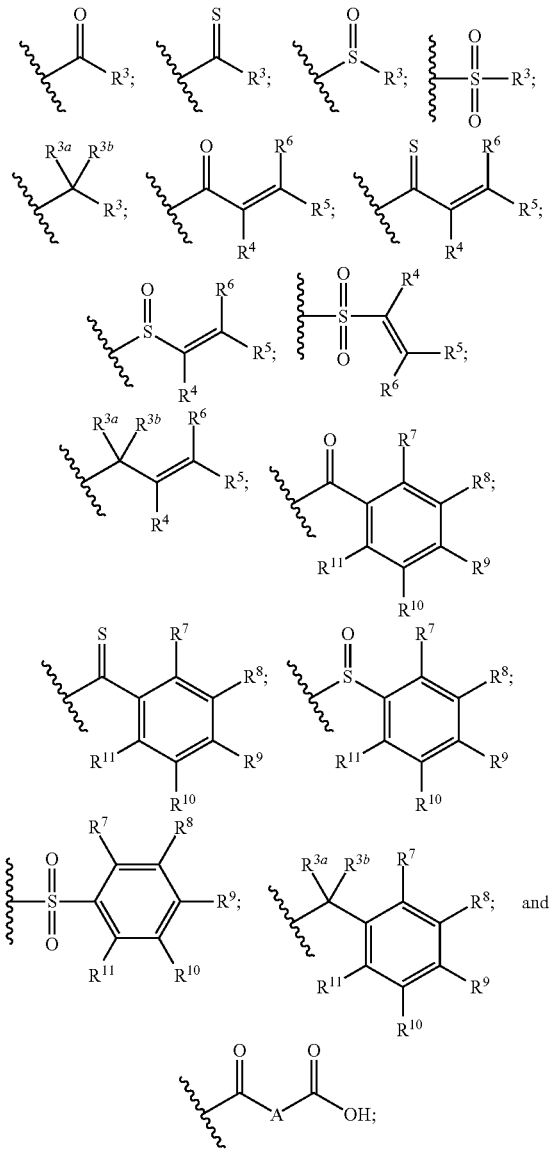

$R^3$, at each occurrence, is independently selected from $C_1$-$C_{12}$ alkyl, heteroaryl, alkoxy, amino, and alkylamino;

$R^4$-$R^6$ are each independently selected from hydrogen, $C_1$-$C_{12}$ alkyl, $C_2$-$C_1$ alkenyl, $C_6$-$C_{18}$ aryl, $C_7$-$C_{18}$ alkyl-substituted aryl, $C_7$-$C_{18}$ aryl-substituted alkyl, $C_2$-$C_{12}$ alkoxycarbonyl, $C_7$-$C_{18}$ aryloxycarbonyl, $C_8$-$C_{18}$ alkyl-substituted aryloxycarbonyl, $C_8$-$C_{18}$ aryl-substituted alkoxycarbonyl, nitrile, formyl, carboxylate, imidate, and thiocarboxylate;

$R^7$-$R^{11}$ are each independently selected from hydrogen, halogen, $C_1$-$C_{12}$ alkyl, $C_2$-$C_{12}$ alkenyl, hydroxy, and amino;

$R^{3a}$ and $R^{3b}$ are each independently selected from hydrogen and $C_1$-$C_{12}$ alkyl;

A at each occurrence is independently selected from a saturated or unsaturated $C_2$-$C_{12}$ divalent hydrocarbon group;

$R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4;

$R^{13}$ at each occurrence is independently a halogen or a $C_1$-$C_6$ alkyl group; c at each occurrence is independently 0 to 4;

$R^{14}$ at each occurrence is independently a $C_1$-$C_6$ alkyl, phenyl, or phenyl substituted with up to five halogens or $C_1$-$C_6$ alkyl groups; and t is 0 to 10, with the proviso that, when IV and/or $R^2$ is

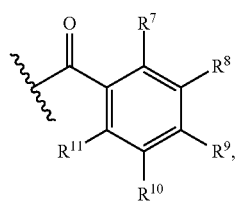

$R^7$ to $R^{11}$ are not all hydrogen.

2. The compound of claim 1, wherein $R^1$ and $R^2$ are each independently selected from:

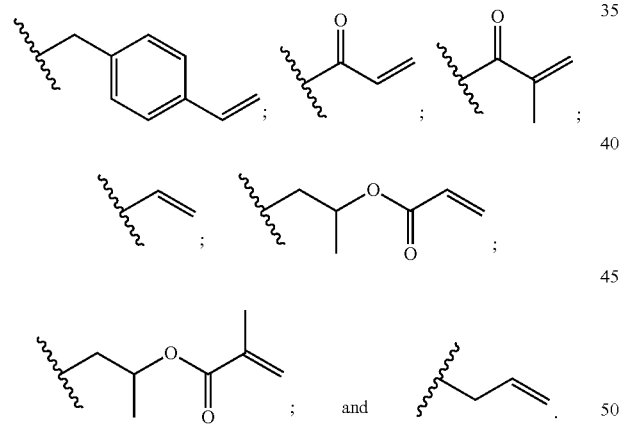

3. The compound of claim 1, selected from a compound having formula:

(1)

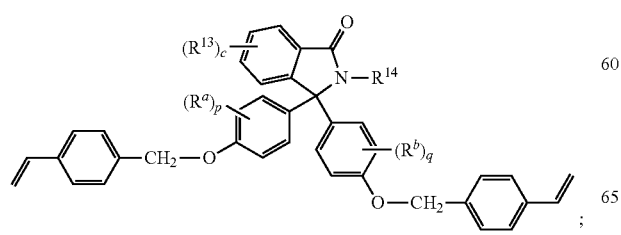

(2)

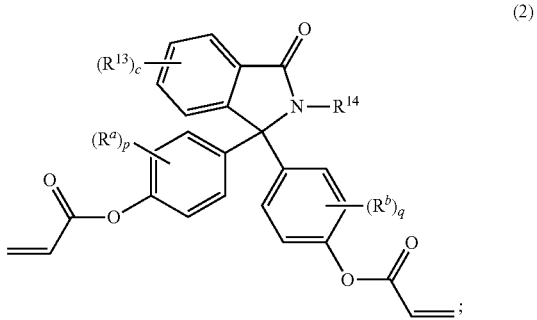

(3)

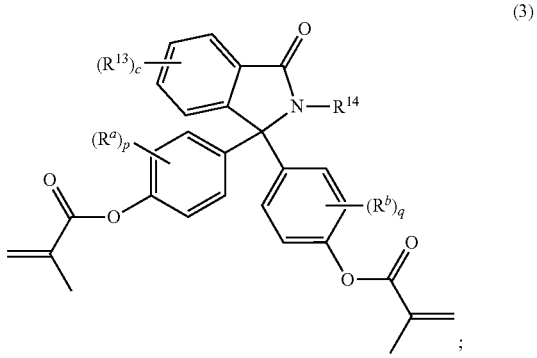

(4)

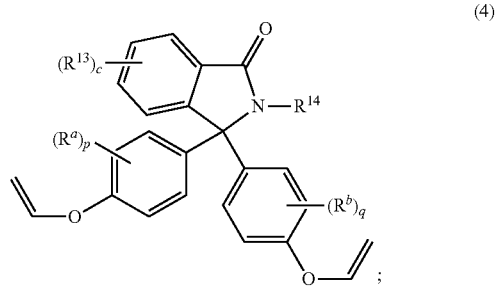

(7)

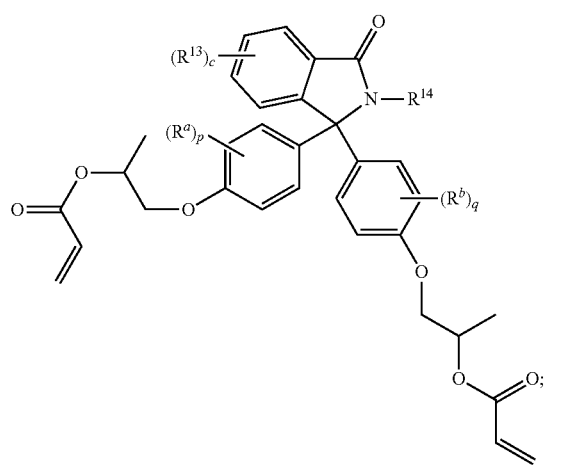

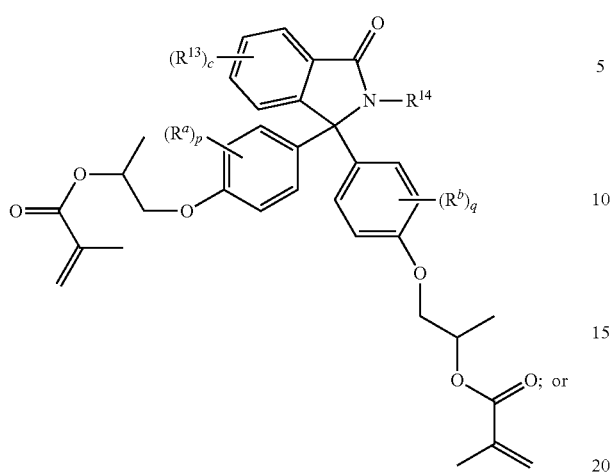

(8)

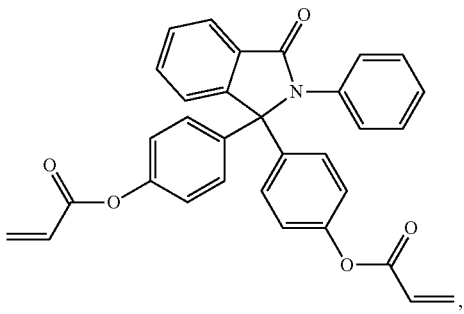

(2-a)

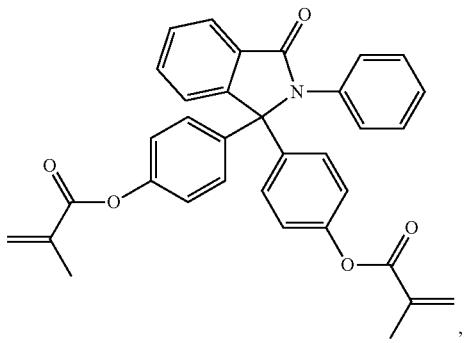

(3-a)

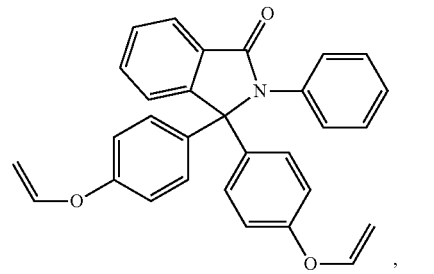

(4-a)

(9)

wherein $R^a$ and $R^b$ at each occurrence are each independently halogen, $C_1$-$C_{12}$ alkyl, $C_2$-$C_{12}$ alkenyl, $C_3$-$C_8$ cycloalkyl, or $C_1$-$C_{12}$ alkoxy; p and q at each occurrence are each independently 0 to 4; $R^{13}$ at each occurrence is independently a halogen or a $C_1$-$C_6$ alkyl group; c at each occurrence is independently 0 to 4; and $R^{14}$ at each occurrence is independently a $C_1$-$C_6$ alkyl, phenyl, or phenyl substituted with up to five halogens or $C_1$-$C_6$ alkyl groups.

4. The compound of claim 1, wherein the compound has a purity of 97% or greater, as determined by high performance liquid chromatography.

5. The compound of claim 1, having formula (1-a), (2-a), (3-a), (4-a), (7-a), (8-a), or (9-a),

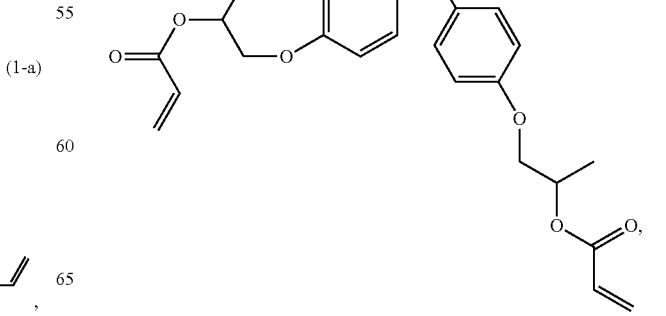

(1-a)

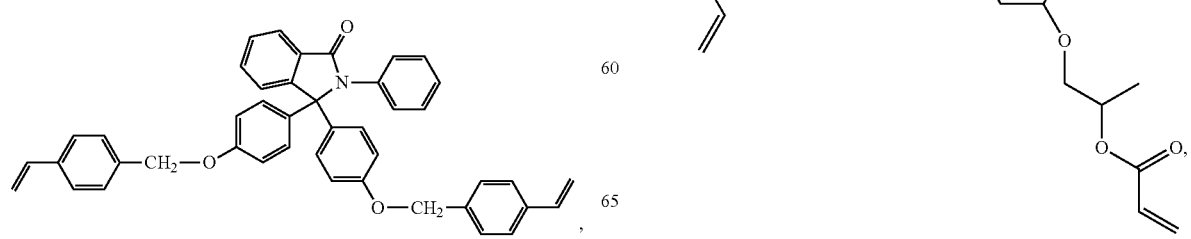

(8-a)

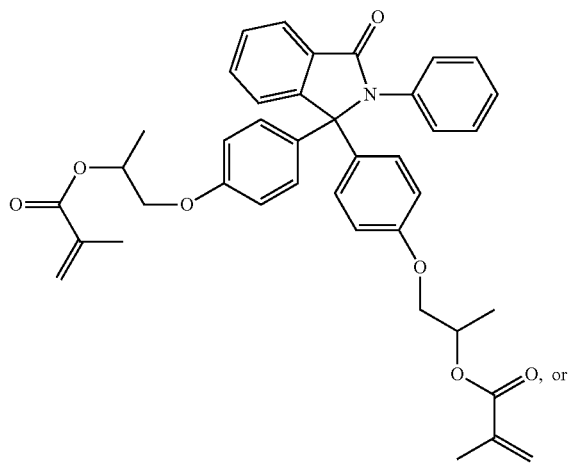

(9-a)

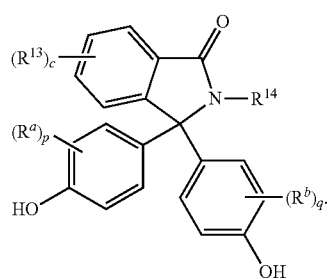

6. The compound of claim 1, wherein the compound is derived from a compound of formula:

(1')

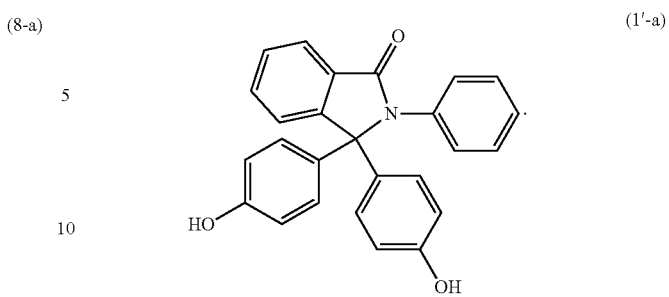

7. The compound of claim 1, wherein the compound is derived from a compound of formula:

(1'-a)

8. The compound of claim 7, wherein the compound of formula (1'-a) comprises less than 50 ppm of amino phenol impurities, less than 500 ppm of phenolphthalein, or 3 ppm or less of metal impurities.

9. A curable composition comprising
(i) a compound according to claim 1;
(ii) optionally a curing promoter; and
(iii) optionally an auxiliary co-monomer.

10. The curable composition of claim 9, wherein the auxiliary co-monomer is selected from maleimide resins, benzoxazine resins, vinylbenzyl ether resins, alkene-containing monomers, alkyne-containing monomers, arylcyclobutene resins, perfluorovinyl ether resins, or a combination thereof.

11. The curable composition of claim 9, wherein the curing promoter is an organic peroxide.

12. The curable composition of claim 11, wherein the organic peroxide is selected from cumene hydroperoxide, 2,5-dimethylhexane-2,5-dihydroperoxide, 2,5-dimethylhexane-2,5-dihydroperoxide, α,α-bis(t-butylperoxy-m-isopropyl)benzene, dicumyl peroxide, di(trimethylsilyl)peroxide, trimethylsilyl triphenylsilyl peroxide, 2,5-dimethyl-2,5-di(t-butylperoxy)hexane, 2,5-dimethyl-2,5-di(t-butylperoxy)-hex-3-yne, di-t-butylperoxide, t-butylcumyl peroxide, dicumyl peroxide, di(t-butylperoxyisophthalate, t-butylperoxybenzoate, 2,2-bis(t-butylperoxy)butane, 2,2-bis(t-butylperoxy)octane, 2,5-dimethyl-2,5-di(benzoylperoxy) hexane, di(trimethylsilyl) peroxide, trimethylsilylphenyltriphenylsilyl peroxide, α,α'-bis(t-butylperoxy-m-isopropyl)benzene, 1,3-di(2-tert-butylperoxy isopropyl) benzene, benzoyl peroxide, 3,3',5,5'-tetramethyl-1,4-diphenoxyquinone, chloranil, 2,4,6-tri-t-butylphenoxyl, t-butylperoxyisopropyl monocarbonate, azobisisobutyronitrile, a combination thereof.

13. A cured composition comprising the product obtained by curing the curable composition of claim 1.

14. The cured composition of claim 13, exhibiting a single glass transition temperature of greater than or equal to 175° C.

15. An article comprising the cured composition of claim 13, wherein the article is selected from acid bath containers; neutralization tanks; aircraft components; bridge beams; bridge deckings; electrolytic cells; exhaust stacks; scrubbers; sporting equipment; stair cases; walkways; automobile exterior panels; floor pans; air scoops; pipes; natural gas pipes; ducts; industrial fans; fan housings; blowers; industrial mixers; boat hulls; boat decks; marine terminal fenders; tiles; building panels; business machine housings; trays; concrete modifiers; dishwasher parts; refrigerator parts; electrical encapsulants; electrical panels; tanks; electrorefining tanks; water softener tanks; fuel tanks; filament-wound tanks; filamount-wound tank linings; furniture; garage doors; gratings; protective body gear; luggage; outdoor motor vehicles; pressure tanks; printed circuit boards; optical waveguides; radomes; railings; railroad parts; hopper car covers; car doors; truck bed liners; satellite dishes; signs; solar energy panels; telephone switchgear housings; tractor parts; transformer covers; truck parts; insulation for rotating machines; commutators; core insulation and cords and lacing tape; drive shaft couplings; propeller blades; missile components; rocket motor cases; wing sections; sucker rods; fuselage sections; wing skins; wing flarings; engine narcelles; cargo doors; tennis racquets; golf club shafts; fishing rods; skis; ski poles; bicycle parts; transverse leaf springs; pumps; automotive smog pumps; electrical components; embedding; tooling; electrical cable joints; wire windings; densely packed multi-element assemblies; sealing of electromechanical devices; battery cases; resistors; fuses; thermal cut-off devices; coatings for printed wiring boards; casting items; capacitors; transformers; crankcase heaters; small molded electronic parts; coils; semiconductors; chemical processing parts; pulp and paper machine parts; power generation parts; wastewater treatment parts; scrubbing towers; pultruded parts for structural applications; structural members; gratings; safety rails; swimming pools; swimming pool slides; hot-tubs; saunas; drive shafts for under the hood applications; dry toner resins for copying machines; marine tooling; marine composites; heat shields; submarine hulls; prototype generation parts; laminated trim; drilling fixtures; bonding jigs; inspection fixtures; industrial metal forming dies; aircraft stretch block and hammer forms; vacuum molding tools; flooring; flooring for production and assembly areas; flooring for clean rooms; flooring for machine shops; flooring for control rooms; flooring for laboratories; flooring for parking garages; flooring for freezers; flooring for coolers; flooring for outdoor loading docks; electrically conductive compositions for antistatic applications; decorative flooring; expansion joints for bridges; injectable mortars for patch and repair of cracks in structural concrete; grouting for tile; machinery rails; metal dowels; bolts and posts; repair material for oil and fuel storage tanks; sport equipment; media equipment; grinding wheels; sanding wheels; mechanical rollers; conveyor belts; military equipment; space equipment; aerospace components; automotive components; mass transportation components; printed circuit boards; electrical components; optical components; optoelectrical components; computer components; watercraft exterior components; watercraft interior components; gas storage tanks; and wind turbines.

16. The article of claim 15, wherein the article is produced by resin transfer molding; sheet molding; bulk molding; pultrusion; injection molding; reaction injection molding; atmospheric pressure molding; casting; centrifugal casting; static casting; open mold casting; lamination; contact molding; cylindrical contact molding; compression molding; vacuum assisted resin transfer molding; chemically assisted resin transfer molding; matched tool molding; autoclave curing; thermal curing in air; vacuum bagging; Seeman's Composite Resin Infusion Manufacturing Processing; open molding; filament winding; cylindrical filament winding; or a combination thereof.

17. A material comprising the cured composition of claim 13, wherein the material is a composite, a coating, an adhesive, an encapsulant, or a sealant.

18. The material of claim 17, wherein the material comprises one or more additional components, each independently selected from flame retardants, fillers, reinforcing fibers, dyes, pigments, colorants, antioxidants, heat stabilizers, light stabilizers, plasticizers, lubricants, flow modifiers, drip retardants, antiblocking agents, antistatic agents, flow-promoting agents, processing aids, substrate adhesion agents, mold release agents, toughening agents, low-profile additives, stress-relief additives, and combinations thereof.

19. The material of claim 17, wherein the composite is a glass fiber composite, a carbon fiber composite, or a combination thereof.

20. The material of claim 17, wherein the material is produced by resin transfer molding.

* * * * *